(12) United States Patent
Magagnoli et al.

(10) Patent No.: US 7,883,709 B2
(45) Date of Patent: Feb. 8, 2011

(54) STABILISED COMPOSITIONS

(75) Inventors: Claudia Magagnoli, Siena (IT); Maurizio Morandi, Siena (IT)

(73) Assignee: Novartis AG, Basel (CH)

( * ) Notice: Subject to any disclaimer, the term of this patent is extended or adjusted under 35 U.S.C. 154(b) by 716 days.

(21) Appl. No.: 10/576,732

(22) PCT Filed: Oct. 22, 2004

(86) PCT No.: PCT/US2004/035039

§ 371 (c)(1), (2), (4) Date: Dec. 26, 2006

(87) PCT Pub. No.: WO2005/042016

PCT Pub. Date: May 12, 2005

(65) Prior Publication Data

US 2007/0110809 A1    May 17, 2007

Related U.S. Application Data

(60) Provisional application No. 60/514,307, filed on Oct. 23, 2003, provisional application No. 60/561,999, filed on Apr. 13, 2004.

(51) Int. Cl.
*A61K 39/02* (2006.01)
(52) U.S. Cl. ............... 424/236.1; 424/241.1; 424/261.1; 424/197.11
(58) Field of Classification Search .................. None
See application file for complete search history.

(56) References Cited

U.S. PATENT DOCUMENTS 4,816,440 A    3/1989 Thomson

2002/0044939 A1    4/2002 Pizza et al.

FOREIGN PATENT DOCUMENTS

WO        WO 01/41800 A2    6/2001
WO        WO 02/101412 A2   12/2002

OTHER PUBLICATIONS

Pronk et al. (1985) J. Biol. Chem. 260:13580-13584.
Manning et al. (1989) Pharm. Res. 6: 903-918.
Wang et al. (1988) J. Parenteral Sci. Tech. 42: S3-S26.
Wang (1999) Int. J. Pharm. 185: 129-188.
Wang et al. (1980) J. Parenteral Drug Assoc. 34: 452-462.
Glenn, G.M. et al. "Transcutaneous immunization with bacterial ADP-ribosylating exotoxins as antigens and adjuvants," Infection and Immunity, vol. 67, No. 3, 1999, pp. 1100-1106.
Krueger, K.M. et al. "The family of bacterial ADP-ribosylating exotoxins," Clinical Microbiology Review, vol. 8, No. 1, 1995, pp. 34-47.
Aktories, K. et al. "Adenylate cyclase inhibition and GTPase stimulation by somatostatin in S49 lymphoma cyc[31] variants are prevented by islet-activating protein," Federation of European Biochemical Societies, vol. 158, No. 1, 1983, pp. 169-173.
Guillén, A. et al. "Differential effects of fluoride and a non-hydrolysable GTP analogue on adenylate cyclase and G-proteins in ceratitis capitala neutral tissue," Cellular Signalling, vol. 5, No. 1, 1993, pp. 81-88.
Sohma, H. et al. "Different functional forms of G-protein beta-gamma-subunits, beta-gamma-I and beta-gamma-II, in bovine brain," Biochemica et Biophysica Acta., vol. 1178, 1993, pp. 111-116.

*Primary Examiner*—Jennifer E Graser
(74) *Attorney, Agent, or Firm*—Helen Lee; Otis Littlefield; Dahna S. Pasternak

(57) ABSTRACT

This invention relates to the stabilization of a bacterial ADP-ribosylating exotoxin class protein (bARE), a method for analysing a bARE class protein, a method for the stabilization of the bARE class bacterial protein, compositions comprising a stabilized bARE protein, compositions comprising a substantially integral bARE class protein and immunogenic composition formulations incorporating same.

13 Claims, 26 Drawing Sheets

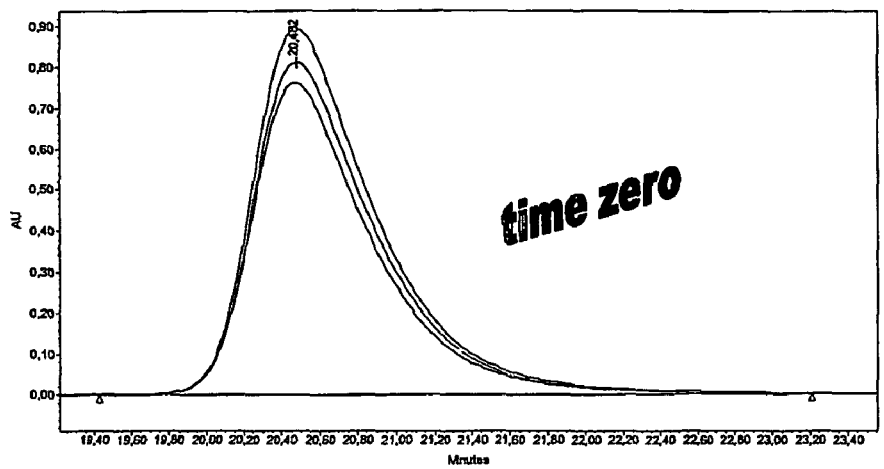
Figure 1A
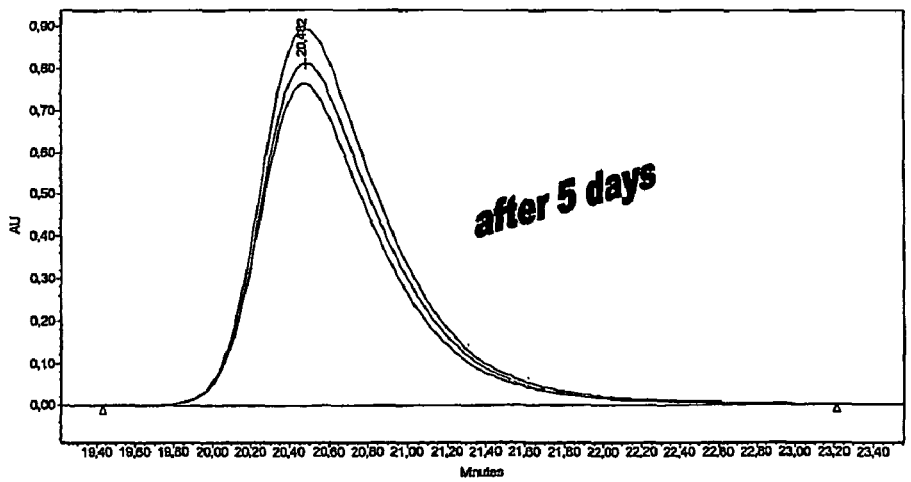
Figure 1B

Superimposition of standard proteins, CRM$_{197}$ reference (bold blue), K63 (bold red) an calibration curve used for apparent MW determination.

Figure 6: SDS-PAGE analysis of LTK 63 shaken samples
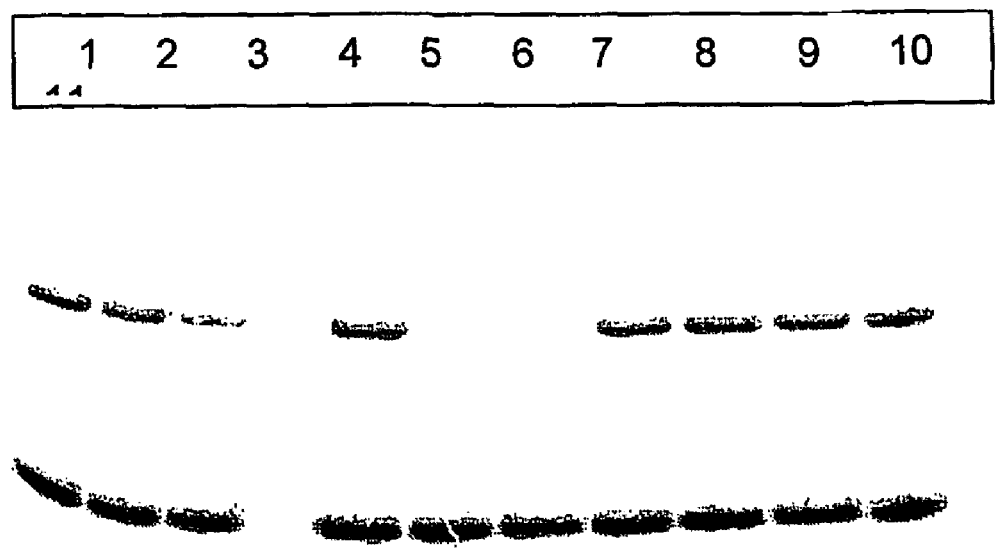

Figure 7: SDS-PAGE analysis of LTK 63 samples treated with CHAPS
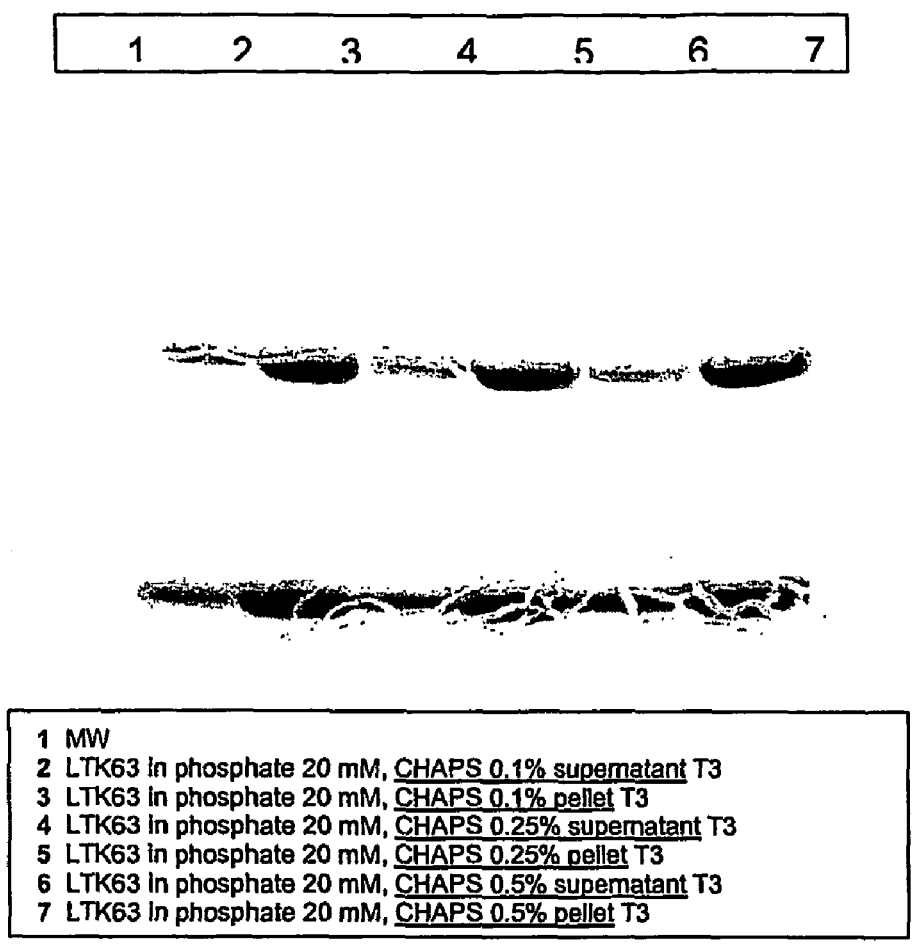

Figure 8: SDS-PAGE of LTK63 samples treated with L-Arginine
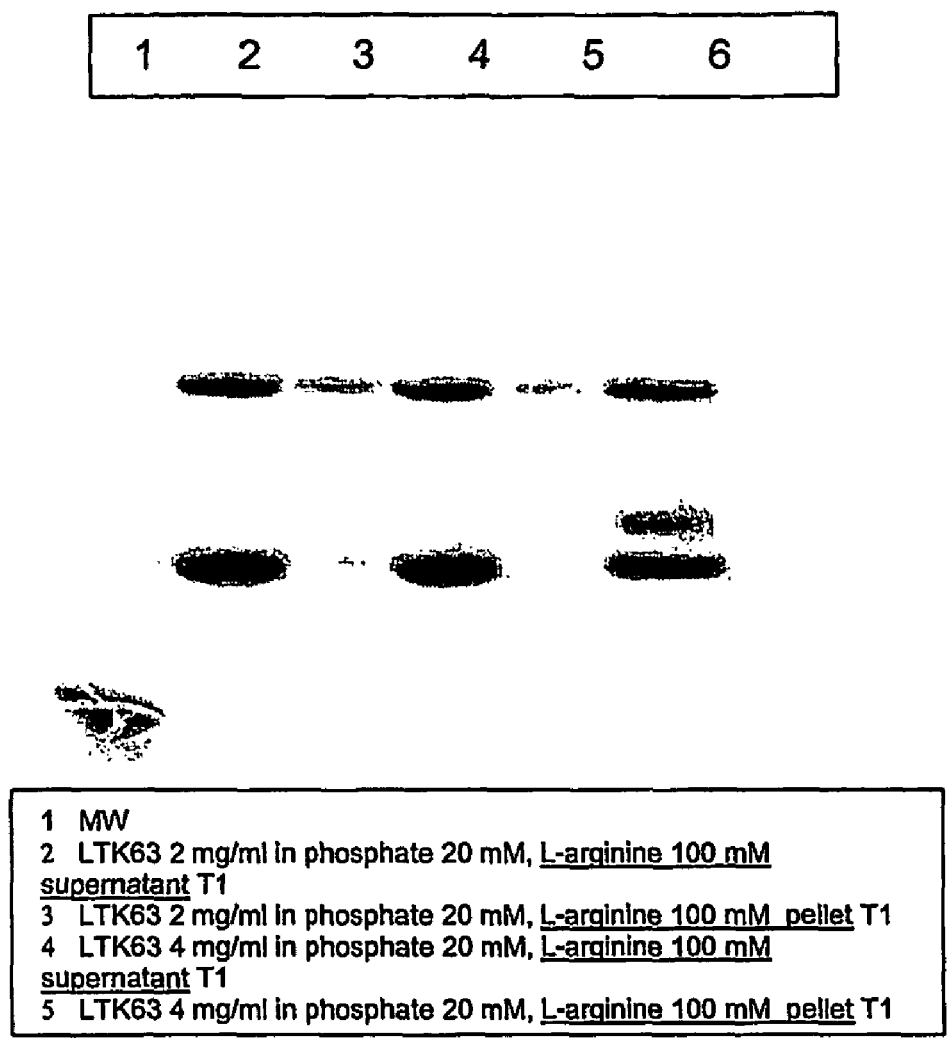

Figure 9(a): Old HPLC Method for analysing L-Arginine treated samples
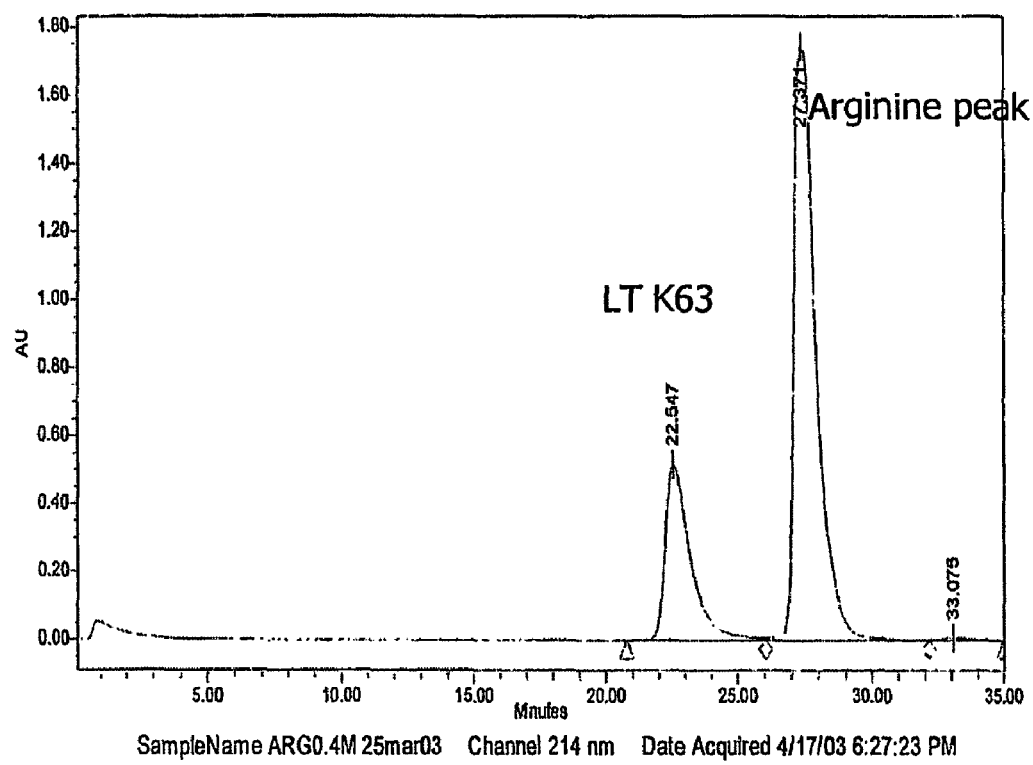

Figure 9(b): New HPLC Method for analysing L-Arginine treated samples
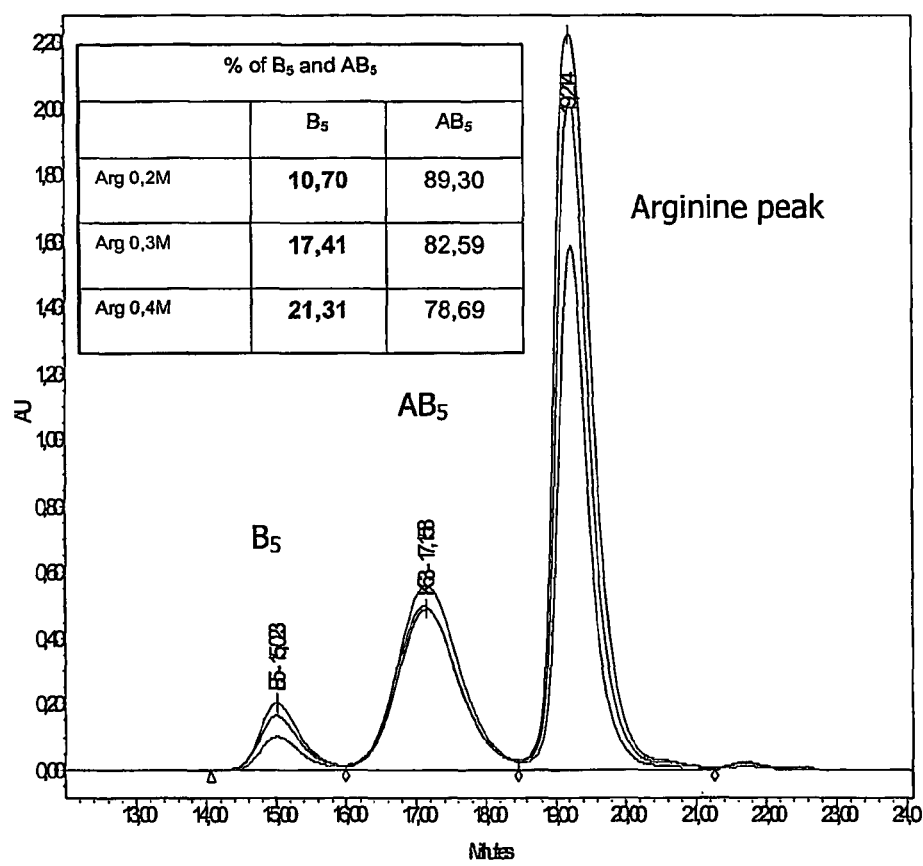

Figure 10(a): Determination of AB5 dissociation in L-Arginine treated samples and the %B5 in LTK63 at 1.3mg/ml
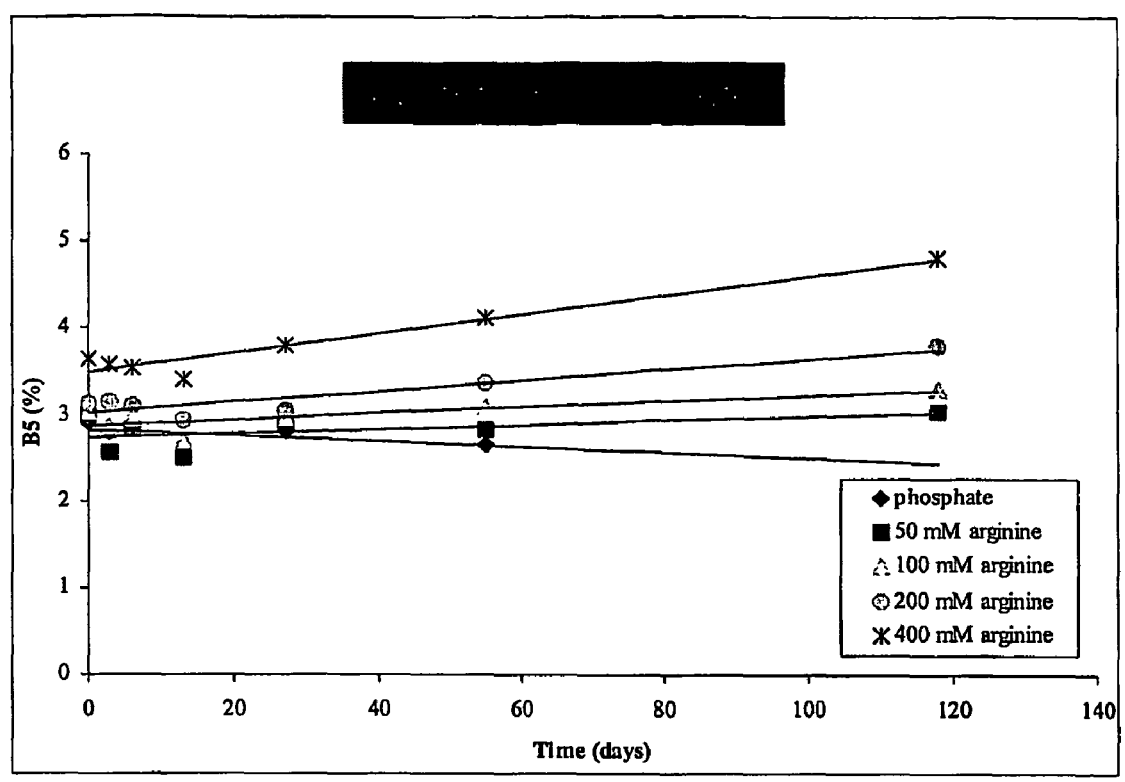

Figure 10(b): Determination of AB5 dissociation in L-Arginine treated samples and the %B5 in LTK63 at 4.0mg/ml
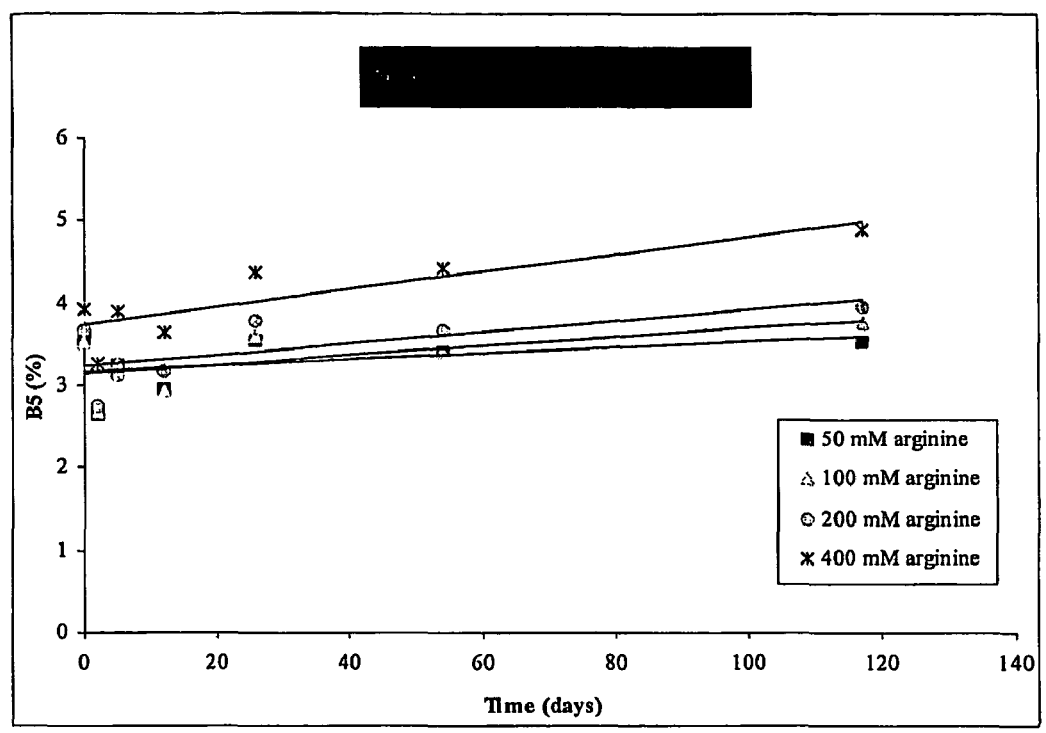

Figure 11(a): CHAPS effect on LTK63 dissociation
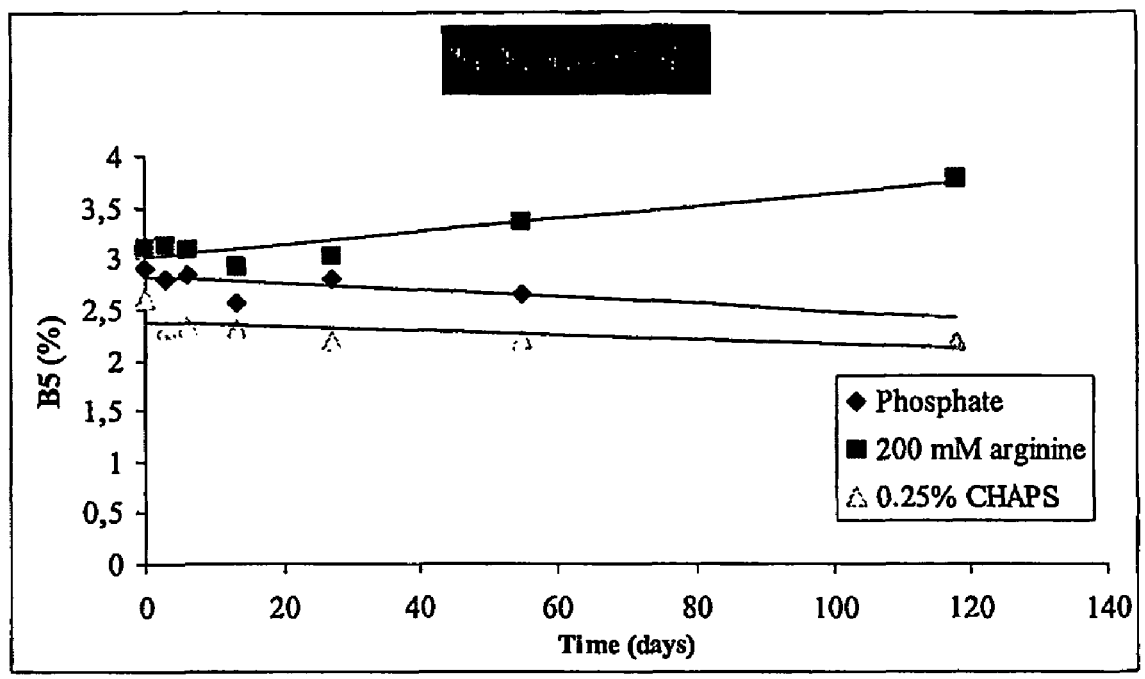

Figure 11(b): CHAPS effect on LT K63 dissociation in combination with L-Arginine
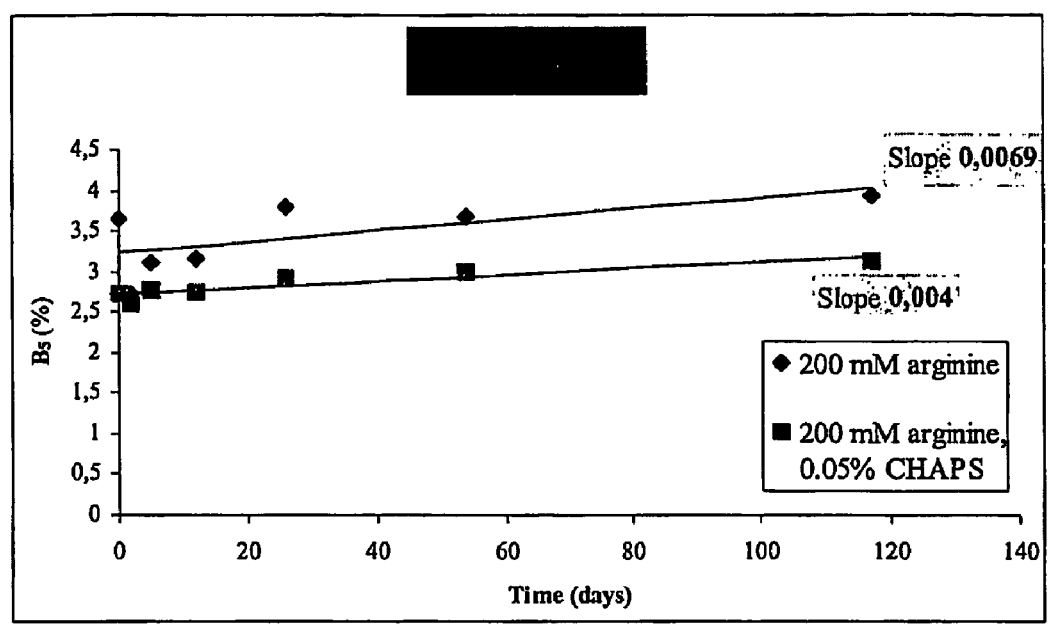

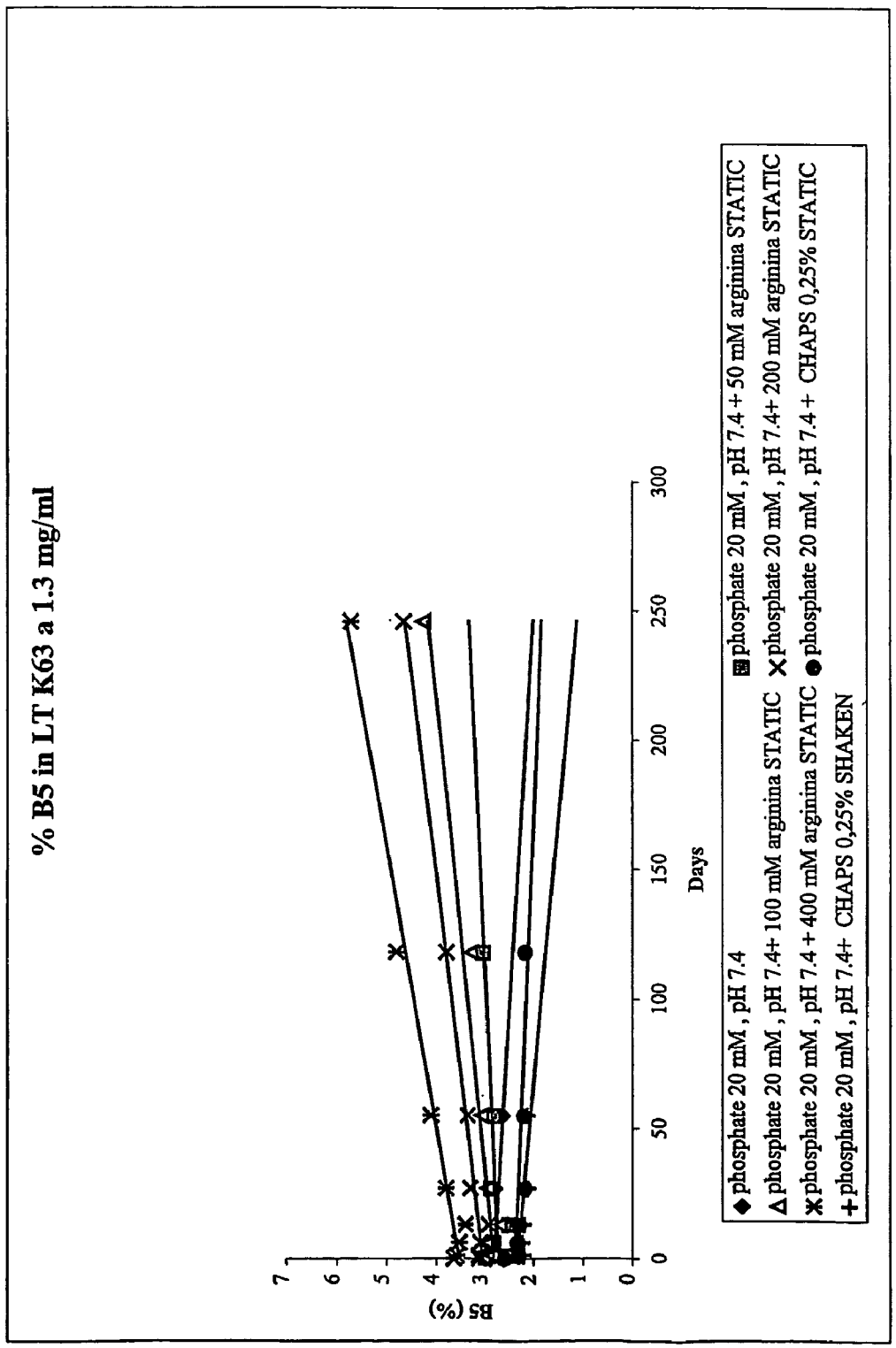
Figure 12: Effect of L-Arginine and CHAPS on LTK 63 stability at a protein concentration of 1,3 mg/ml

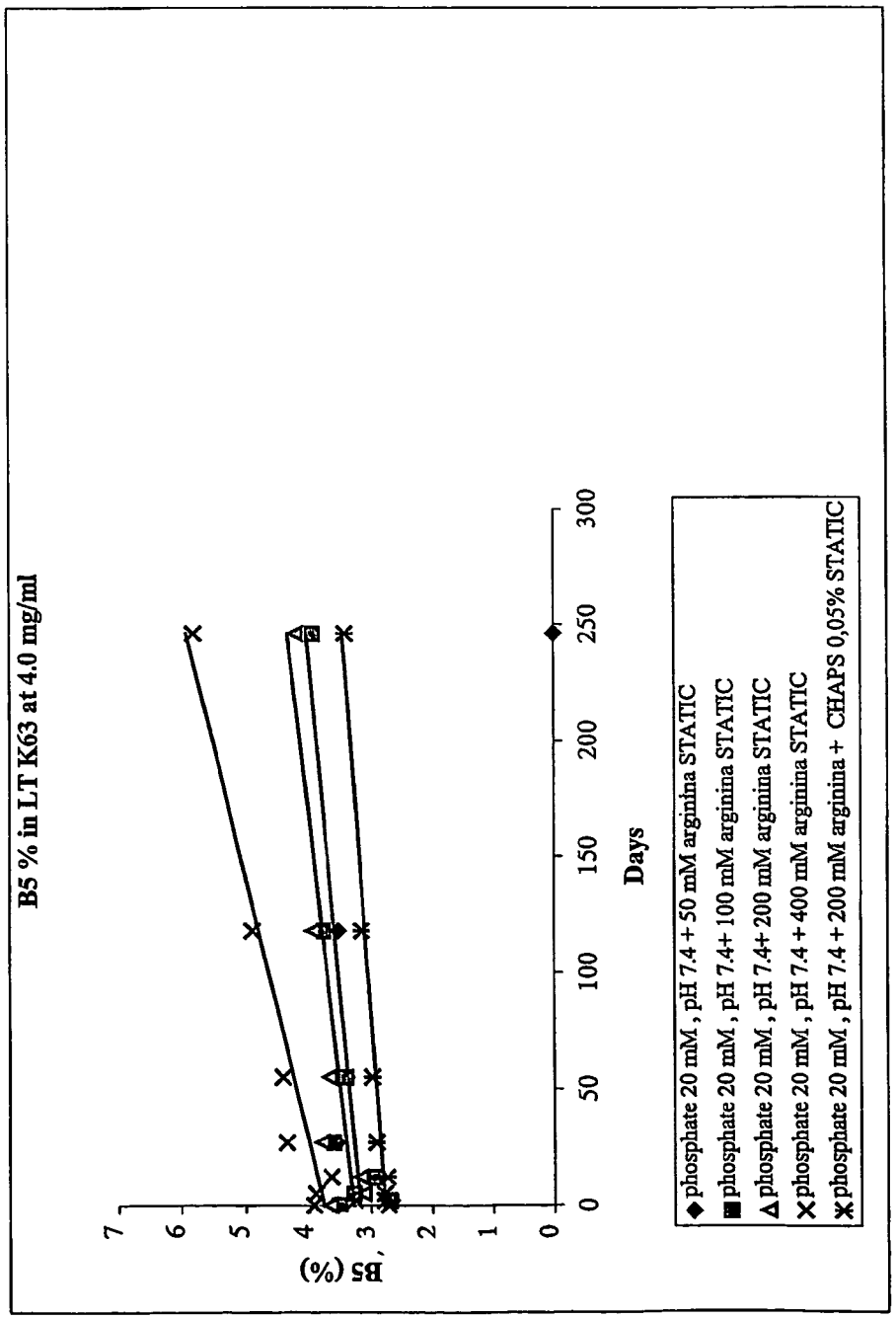
Figure 13: The effect of L-Arginine and the combination L-Arginine/CHAPS on LTK 63 stability at a protein concentration of 4,0 mg/ml Figure 14 shows the effect of storage conditions on LTK 63 stability in L-Arginine + CHAPS containing buffers
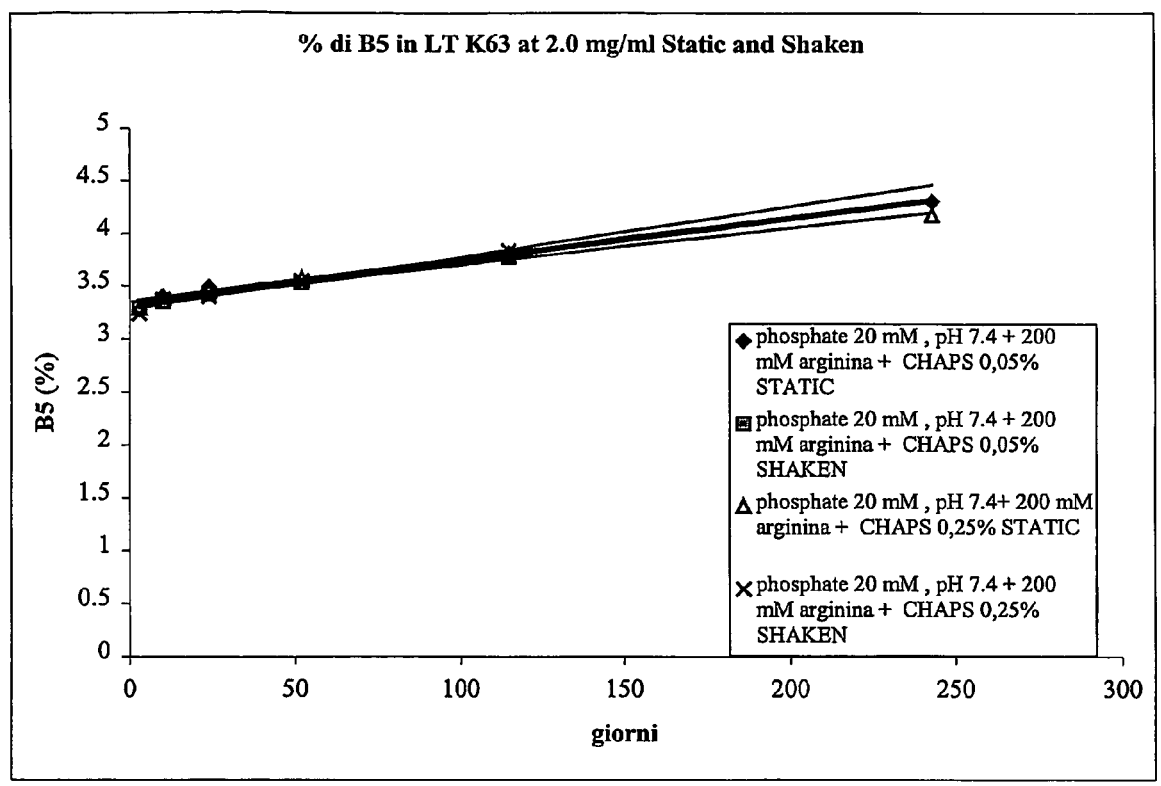

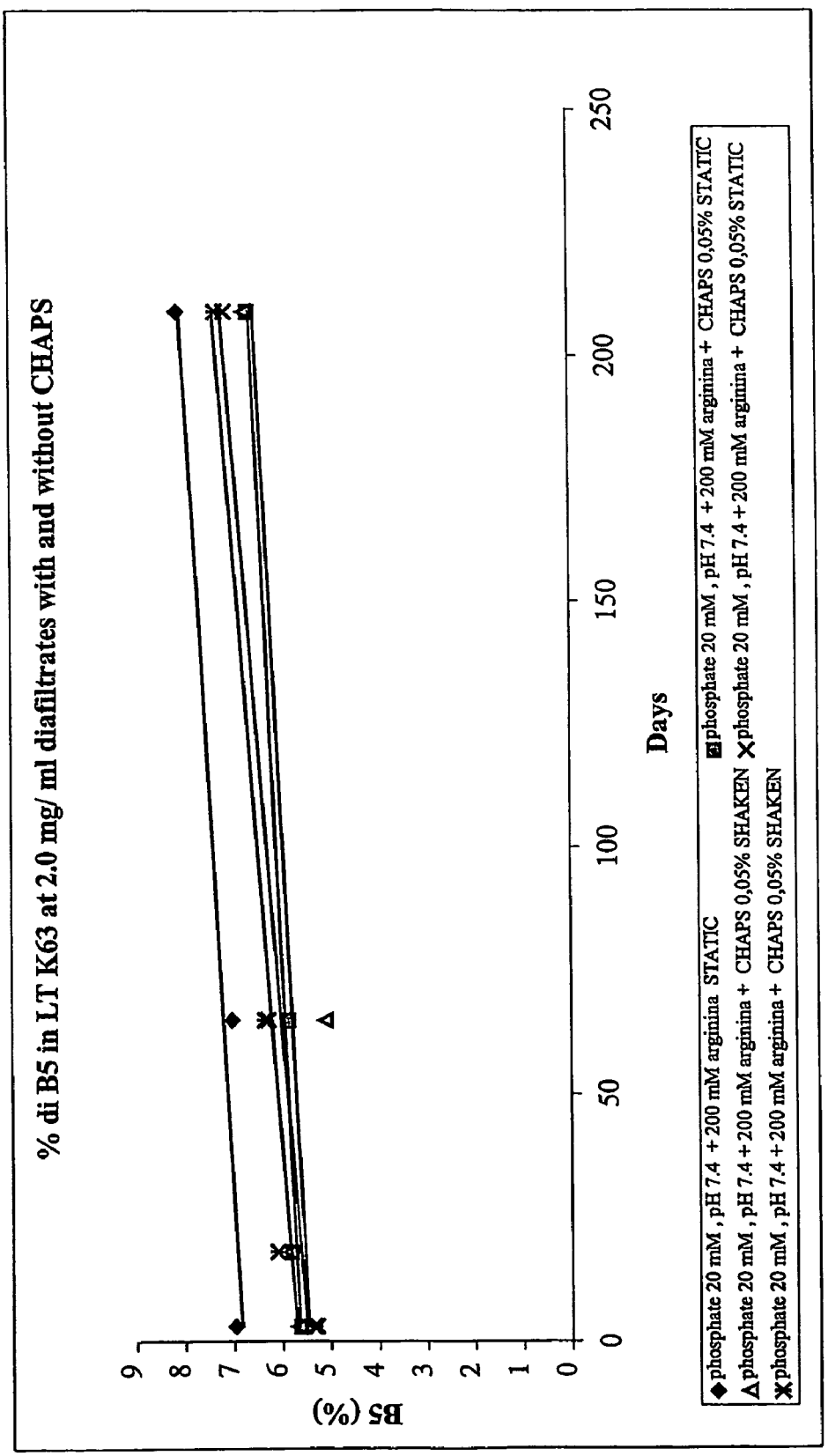
Figure 15: Comparison of LTK 63 stability on L-Arginine and L-Arginine + CHAPS storage buffers

Figure 17

Zwitterionic Detergents

| Product | Cat. No. | M.W. (anhydrous) | CMC[b] (mM) | Aggregation No. | Average Micellar Weight | size |
|---|---|---|---|---|---|---|
| ASB-14 | 182750 | 434.7 | — | — | — | 5g, 25 g |
| ASB-16 | 182755 | 462.7 | — | — | — | 5g, 25 g |
| CHAPS | 220201 | 614.9 | 6-10 | 4-14 | 6000 | 1 g / 5 g / 10 g / 25 g |
| CHAPSO | 220202 | 630.9 | 8 | — | 7000 | 5 g |
| DDMAB | 252080 | 299.5 | 4.3 | — | — | 5 g |
| DDMAU | 252005 | 397.7 | 0.113 | — | — | 5 g |
| EMPIGEN BB® Detergent 30% Solution | 324690 | 272.0 | 1.6-2.1 | — | — | 100 ml |
| Lauryldimethylamine Oxide (LDAO) 30% Solution | 428011 | 229.4 | 1-2 | 76 | 17,000 | 100 ml |
| ZWITTERGENT® 3-08 Detergent | 693019 | 279.5 | 330 | — | — | 5 g |
| ZWITTERGENT® 3-10 Detergent | 693021 | 307.6 | 25-40 | 41 | 12,500 | 5 g |
| ZWITTERGENT® 3-12 Detergent | 693015 | 335.6 | 2-4 | 55 | 18,500 | 5 g, 25 g |
| ZWITTERGENT® 3-14 Detergent | 693017 | 363.6 | 0.1-0.4 | 83 | 30,000 | 5 g, 25 g |
| ZWITTERGENT® 3-16 Detergent | 693023 | 391.6 | 0.01-0.05 | 155 | 60,000 | 5 g, 25 g | a. Average molecular weights are given for detergents composed of mixtures of chain lengths; b. Temperature: 20 - 25°C

TRADEMARKS

BRIJ® and TWEEN® are registered trademarks of ICI Americas, Inc.
EMPIGEN BB® is a registered trademark of Albright & Wilson.
GENAPOL® is a registered trademark of Hoechst AG;
ULTROL®, PROTEIN GRADE® and ZWITTERGENT® are registered trademarks of Calbiochem-Novabiochem Corporation.
CALBIOSORB™ Adsorbent and ELUGENT™ Detergent are trademarks of Calbiochem-Novabiochem Corporation LUBROL® is a registered trademark of Imperial Chemical Inc.
PLURONIC® is a registered trademark of Wyandotte Chemicals Corporation.
TRITON X® is a registered trademark of Rohm and Hass.

STABILISED COMPOSITIONS

CROSS-REFERENCE TO RELATED APPLICATIONS

This application is a 35 U.S.C. §371 filing of PCT/US2004/035039, filed Oct. 22, 2004. PCT/US2004/035039 claims the benefit of U.S. Provisional Application No. 60/514,307, filed Oct. 23, 2003 and U.S. Provisional Application No. 60/561,999, filed Apr. 13, 2004. The disclosures of all of the aforementioned applications are incorporated by reference in their entireties for all purposes.

STATEMENT OF RIGHTS TO INVENTIONS MADE UNDER FEDERALLY SPONSORED RESEARCH

Not applicable.

TECHNICAL FIELD

This invention relates to the stabilization of a bacterial ADP-ribosylating exotoxin class protein (bARE), a method for analysing a bARE class protein, a method for the stabilization of the bARE class bacterial protein, compositions comprising a stabilized bARE protein, compositions comprising a substantially integral bARE class protein and immunogenic formulations incorporating same.

BACKGROUND

An important part of the development of a protein therapeutic is the preparation of the protein in a stabilised form that can be stored over extended periods without loss of activity so that the dose and activity of the protein therapeutic can be carefully controlled.

Polypeptides can lose biological activity as a result of physical instabilities, including denaturation and formation of soluble and insoluble aggregates, and a variety of chemical instabilities, such as hydrolysis, oxidation, and deamidation. Stability of polypeptides in liquid pharmaceutical formulations can be affected, for example, by factors such as pH, ionic strength, temperature, repeated cycles of freeze-thaw, and exposure to mechanical shear forces such as occur during processing. Aggregate formation and loss of biological activity can also occur as a result of physical agitation and interactions of polypeptide molecules in solution and at the liquid-air interfaces within storage vials. Further conformational changes may occur in polypeptides adsorbed to air-liquid and solid-liquid interfaces during compression-extension of the interfaces resulting from agitation during transportation or otherwise. Such agitation can cause the protein to entangle, aggregate, form particles, and ultimately precipitate with other adsorbed proteins. For a general review of stability of protein pharmaceuticals, see, for example, Manning et al. (1989) Pharm. Res. 6: 903-918, and Wang and Hanson (1988) J. Parenteral Sci. Tech. 42: S14.

The development of multimer protein therapeutics presents additional challenges especially if the integrity of the multimer protein is essential for the efficacy of the therapeutic end product. In such cases, not only is it necessary to ensure that the protein is maintained without loss of activity and without protein precipitation or aggregation but it is also important to check if the integrity of the multimer protein has been maintained in the therapeutic end product.

To date, workers in the field of stabilisation of multimer proteins, such as a bacterial ADP-ribosylating exotoxin class proteins (bAREs) which are organised as A:B multimers have been faced with at least two different types of problems when working with such proteins. In particular, the bARE proteins may lose their biological activity: (i) as a result of physical instabilities including denaturation and formation of soluble and insoluble aggregates; and/or (ii) by the partial or complete dissociation of the bARE protein into its A and B subunit forms.

Sometimes it may be easy to see when a protein, such as a multimeric protein precipitates out of solution because aggregate or crystalline particles may form. On the other hand, it is not so easy to determine if a multimeric protein has dissociated either partially or completely into its subunit forms because, for example, a protein assay, will not differentiate over intact and dissociated forms of the multimeric protein.

To date, no information has been available on how to measure the integrity of bARE proteins multimers without loss of the integral multimer structure. Current analytical methods used to characterize multimeric bARE class proteins, including electrophoresis, immunoblotting, mass spectrometry and amino acid analysis, are unable to distinguish between the integral multimeric structure and the separate dissociated subunit forms. This failure to differentiate between integral and dissociated bARE proteins is due to the fact that the current analytical techniques require the dissociation of the A and B subunit forms and so do not maintain the structural organisation of the integral multimeric bARE molecule. Neither do these techniques permit the quantitation of the integral bARE molecule relative to the dissociated subunit molecule. Therefore, current analytical methods are neither useful for studying the dissociation (or loss of integrity) of the multimeric bARE protein over time nor for looking for ways to stabilise the multimeric bARE protein. In addition, even when traditional separation methods, such as gel filtration methods are used, which do not require the dissociation into monomeric subunit forms, these methods are not very effective as they do not permit a good resolution of the different subunit forms because of extremely close retention times.

As a result, up until now, a reliable method of determining whether or not a particular sample of a bARE molecule is present in an intact or dissociated form has not been available to workers in the field of bARE molecules. Such a method would be useful not only for: (i) distinguishing between the integral multimeric bARE structure and separate, dissociated A and B subunits but would also be useful for (ii) investigating and determining the conditions required for stability of a bARE class protein including the identification of effective stabilizing agents. Methods of evaluating, achieving and quantifying the stability of bARE class proteins would be very useful for (iii) the development of appropriate formulations for bARE class proteins for stable storage and delivery of the bARE protein, either alone or, for example, as part of a composition, such as an immunogenic (e.g., vaccine) composition.

As mentioned above, another major obstacle that must be overcome in the use of protein-based pharmaceuticals, such as those including a bARE protein as a therapeutic agent is the loss of pharmaceutical utility that may result from its instability in pharmaceutical formulations. The stabilization of polypeptides in pharmaceutical compositions remains an area in which trial and error plays a major role (reviewed by Wang (1999) Int. J. Pharm. 185:129-188; Wang and Hanson (1988) J. Parenteral Sci. Tech. 42:S3-S26). Excipients that are added to polypeptide pharmaceutical formulations to increase their stability include buffers, sugars, surfactants, amino acids, polyethylene glycols, and polymers, but the stabilizing effects of these chemical additives may vary depending on the protein. Physical instabilities that threaten polypeptide activity and efficacy in pharmaceutical formulations include denaturation and formation of soluble and insoluble aggregates. Some of these changes are known to lead to the loss or reduction of the pharmaceutical activity of the bARE protein of interest. In other cases, the precise effects of these changes are unknown, but the resulting degradative products are still considered to be pharmaceutically unacceptable due to the potential for undesirable side effects.

Aggregate formation by a polypeptide such as a bARE molecule during storage of a pharmaceutical composition can adversely affect biological activity of that polypeptide, resulting in loss or reduction of the pharmaceutical activity or therapeutic efficacy of the pharmaceutical composition. Furthermore, aggregate formation may cause other problems such as blockage of tubing, membranes, or pumps when the functional stability of a bARE protein is determined using an analytical system, such as a chromatographic method or when the bARE protein based pharmaceutical composition is administered using an infusion system. In addition, injection of a pharmaceutical composition comprising the aggregated form of a protein has the potential for generating an immunogenic reaction to the aggregated protein.

Consequently, there is also a need to: (i) find ways of determining the stability of a bARE protein over time; (ii) identify stabilisers that can improve the stability of a bARE protein over time; and (iii) provide bARE compositions which are stable on storage and which have a prolonged activity over time.

SUMMARY

The present invention provides: (i) a method for analysing a bARE protein under non-dissociating conditions; (ii) a method for determining the degree of integrity of the bARE protein; (iii) stabilisers capable of stabilising a bARE protein; (iv) a method for stabilising a bARE protein; (v) compositions comprising a stabilised bARE protein; and (vi) compositions comprising a substantially intergral bARE class protein.

The present invention makes an important contribution to the art because this is the first time that: (i) the functional stability/integrity of a bARE protein may be evaluated without loss of its integral multimer structure; (ii) the functional stability of a bARE protein may be determined in terms of non-dissociated and dissociated forms of the bARE protein; and (iii) the impact of candidate stabilising agents on the functional stability of a bARE protein may be determined in accordance with points (i) and (ii).

The present invention also satisfies a long felt need for stabilised bARE compositions and methods for preparing stabilised bARE compositions which reduce protein aggregation and enhance the physical stabilisation and/or functional stabilisation of a bARE protein. The analytical method of the present invention also permits, again for the first time, the evaluation of the effect of a physical stabilising agent on the functional stability of a bARE protein and/or the evaluation of the effect of a functional stabilising agent on the physical stability of a bARE protein. In this way, bARE protein stabilising agents can be identified which may have selective effects on either the physical stability or the functional stability of a bARE protein or which may have a synergistic effect on both the physical stability and the functional stability of a bARE protein. Thus, by using certain stabilisation agents either alone and/or in combination a reduction of aggregation and thus an increase in physical stabilisation of a bARE protein and/or a reduction in dissociation and thus an increase in the functional stability of a bARE protein may be achieved and/or maintained over time.

According to a first aspect of the present invention, there is provided a composition comprising a substantially integral bARE class protein.

As no analytical method was previously available for evaluating the integrity of a bARE protein without loss of its integral structure, this is the first time that the existence of a substantially integral bARE protein has been determined.

According to a second aspect of the present invention, there is provided a method of stabilising a bARE protein wherein the method comprises providing a bARE class protein and combining the bARE class protein with a stabilising agent. An advantage of this aspect of the invention is that a bARE protein can be stabilised over time.

According to a third aspect of the present invention, there is provided a method of analysing a bARE class protein under non-dissociating conditions that differentiate between integral and dissociated bARE class proteins.

As explained above, this method is advantageous because, up until now, no method was available to date for evaluating the integrity of a bARE protein without loss of its integral structure.

According to a fourth aspect of the present invention, there is provided a method of analysing a bARE class protein wherein the method comprises: applying a bARE class protein to a charged polymeric separation material in an apparatus configured to resolve an integral bARE class protein from a dissociated bARE class protein, treating the separation material comprising the applied bARE class protein with an ionic buffer; and detecting one or more integral or dissociated bARE class proteins.

In another aspect of the present invention, there is provided a method for identifying a bARE class protein stabilisation agent wherein the method comprises: combining a bARE class protein with a candidate stabilising agent to form a bARE protein sample; applying the bARE protein sample to a charged polymeric separation material in an apparatus configured to resolve an integral bARE class protein from a dissociated bARE class protein; treating the separation material comprising the applied bARE class protein with an ionic buffer; detecting one or more integral or dissociated bARE class proteins; and determining whether the candidate stabilising agent is a bARE protein stabilising agent.

In a further aspect of the present invention, there is provided an immunogenic composition (e.g., vaccine), the composition comprising the stabilised bARE compostions as defined herein.

Other aspects of the present invention are presented in the accompanying claims and in the following description and drawings. These aspects are presented under separate section headings. However, it is to be understood that the teachings under each section are not necessarily limited to that particular section heading.

BRIEF DESCRIPTION OF THE DRAWINGS

The following invention will now be further described only by way of example in which reference is made to the following Figures. The following examples are presented only to illustrate the present invention and to assist one of ordinary skill in making and using the same. The examples are not intended in any way to otherwise limit the scope of the invention. Efforts have been made to ensure accuracy with respect to numbers used (e.g., amounts, temperatures, etc.), but some experimental error and deviation should, of course, be allowed for.

FIGS. 1A-B depict the chromatograms of samples of LTK63 ($AB_5$ protein) run on a conventional GF-HPLC system immediately after sample preparation and five days after sample preparation.

FIG. 4 presents a 214 nm chromatogram of a single fractionating run.

FIG. 5C shows a superimposition of standard proteins, CRM197 reference, LTK63 and calibration curve used for apparent MW determination.

FIG. 6 shows SDS-PAGE analysis of shaken LTK63 samples. The samples applied to each lane are as follows: 1 LTK63 in PBS T0; 2 LTK63 in PBS Supernatant T1; 3 LTK63 in PBS Supernatant T6; 4 MW; 5 LTK63 in NaCl 0.5 M Supernatant T0; 6 LTK63 in NaCl 0.5 M Supernatant T1; 7 LTK63 in NaCl 0.5 M Supernatant T6; 8 LTK63 in phosphate 20 mM, CHAPS 0.25% T0; 9 LTK63 in phosphate 20 mM, CHAPS 0.25% Supernatant T1; 10 LTK63 in phosphate 20 mM, CHAPS 0.25% Supernatant T6; and 11 LTK 63 std.

FIG. 7 shows SDS-PAGE analysis of LTK63 samples treated with CHAPS at various concentrations. The samples applied to each lane are as follows: 1 MW Calibration marker; 2 LTK63 in phosphate 20 mM, CHAPS 0.1% supernatant T3; 3 LTK63 in phosphate 20 mM, CHAPS 0.1% pellet T3; 4 LTK63 in phosphate 20 mM, CHAPS 0.25% supernatant T3; 5 LTK63 in phosphate 20 mM, CHAPS 0.25% pellet T3; 6 LTK63 in phosphate 20 mM, CHAPS 0.5% supernatant T3; 7 LTK63 in phosphate 20 mM, CHAPS 0.5% pellet T3.

FIG. 8 shows an SDS-PAGE analysis of LTK63 samples treated with 100 mM L-Arginine. The samples applied to each lane are as follows: 1 MW; 2 LTK63 2 mg/ml in phosphate 20 mM, L-Arginine 100 mM supernatant T1; 3 LTK63 2 mg/ml in phosphate 20 mM, L-Arginine 100 mM pellet T1; 4 LTK63 4 mg/ml in phosphate 20 mM, L-Arginine 100 mM supernatant T1LTK63 4 mg/ml in phosphate 20 mM, L-Arginine 100 mM pellet T1.

FIG. 9(a) shows an analysis of L-Arginine shaken LTK63 samples using an old known HPLC method.

FIG. 9(b) shows an analysis of L-Arginine shaken LTK63 samples using the new HPLC method.

FIG. 10(a) provides a determination of AB5 dissociation in L-Arginine treated samples and the % B5 in LTK63 at 1.3 mg/ml using the new HPLC Method.

FIG. 10(b) provides a determination of AB5 dissociation in L-Arginine treated samples and the % B5 in LTK63 at 4.0 mg/ml using the new HPLC Method.

FIG. 11(a) shows the effect of the inclusion of CHAPS on LTK63 dissociation.

FIG. 11(b) shows the effect of the inclusion of CHAPS in combination with L-Arginine on LTK63 dissociation.

FIG. 12 shows the effect of L-Arginine and CHAPS on LTK 63 stability at a protein concentration of 1.3 mg/ml.

FIG. 13 shows the effect of L-Arginine and the combination L-Arginine/CHAPS on LTK 63 stability at a protein concentration of 4,0 mg/ml.

FIG. 14 shows the effect of storage conditions on LTK 63 stability in L-Arginine+CHAPS containing buffers.

FIG. 15 provides a comparison of LTK 63 stability on L-Arginine and L-Arginine+CHAPS storage buffers.

FIG. 17 provides information on a number of zwitterionic detergents.

Figure 1C:
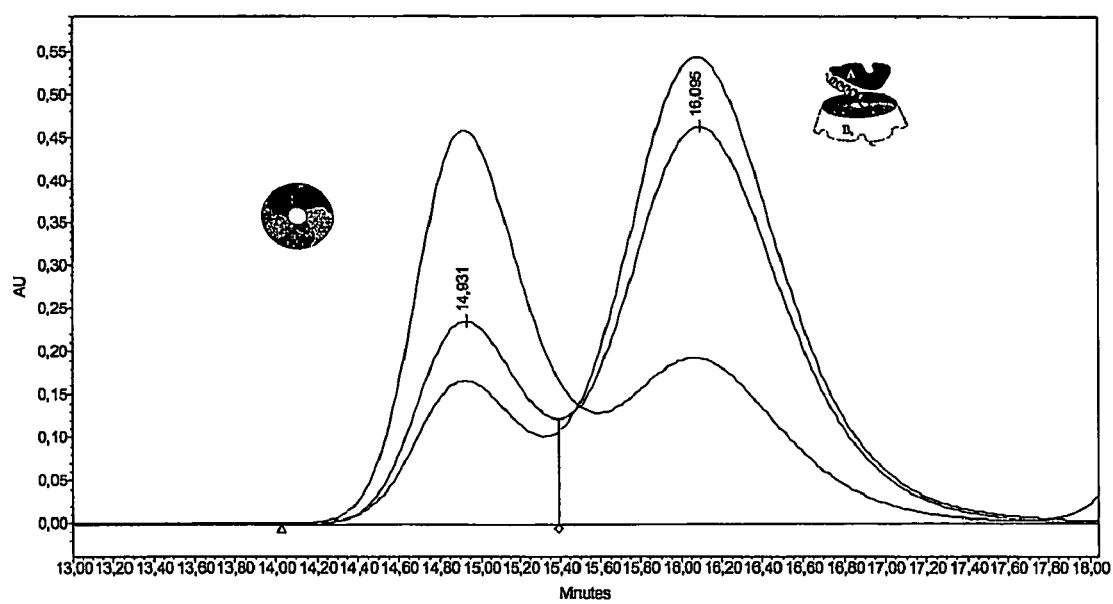
FIG. 1C depicts the chromatogram of samples of LTK63 run on a GF-HPLC system in accordance with the present invention five days after sample preparation.

The one-letter amino acid symbols recommended by the IUPAC-IUB Biochemical Nomenclature Commission are provided below together with the three-letter codes which are also provided for reference purposes.

| A | Ala | Alanine |
| C | Cys | Cysteine |
| D | Asp | Aspartic acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

DETAILED DESCRIPTION

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of virology, microbiology, molecular biology, recombinant DNA techniques and immunology all of which are within the ordinary skill of the art. Such techniques are explained fully in the literature. See, e.g., Sambrook, et al., *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *A Practical Guide to Molecular Cloning* (1984); and *Fundamental Virology*, 2nd Edition, vol. I & II (B. N. Fields and D. M. Knipe, eds.).

All publications, patents and patent applications cited herein, whether supra or infra, are hereby incorporated by reference in their entirety. It must be noted that, as used in this specification and the appended claims, the singular forms "a", "an" and "the" include plural referents unless the content clearly dictates otherwise. All scientific and technical terms used in this application have meanings commonly used in the art unless otherwise specified. As used in this application, the following words or phrases have the meanings specified.

The term "comprising" means "including" as well as "consisting" e.g. a composition "comprising" X may consist exclusively of X or may include something additional e.g. X+Y.

The term "about" in relation to a numerical value x means, for example, x±10%.

Unless otherwise noted, terminology used herein should be given its normal meaning as understood by one of skill in the art. In order to facilitate understanding of the present invention, a number of defined terms are used herein to designate particular elements of the present invention. When so used, the following meanings are intended:

Bacterial ADP-Ribosylating Exotoxins (bAREs)

As used herein, the term "bARE" refers to a class of ADP-ribosylating bacterial toxins which are a family of related bacterial exotoxins and include diphtheria toxin (DT), pertussis toxin (PT), cholera toxin (CT), the *E. Coli* heat-labile toxins (LT1 and LT2), *Pseudomonas* endotoxin A, *Pseudomonas* exotoxin S, *B. cereus* exoenzyme, *B. sphaericus* toxin, *C. botulinum* C2 and C3 toxins, *C. limosum* exoenzyme, as well as toxins from *C. perfringens*, *C. spiriforma* and *C. difficile*, *Staphylococcus aureus* EDIN, and ADP-ribosylating bacterial toxin mutants such as $CRM_{197}$, a non-toxic diphtheria toxin mutant (see, e.g., Bixler et al. (1989) *Adv. Exp. Med. Biol.* 251:175; and Constantino et al. (1992) *Vaccine*). Most ADP-ribosylating bacterial toxins are organized as an A:B multimer, wherein the A subunit contains the toxic enzymatic activity called ADP-ribosyltransferase activity, and the B subunit acts as the binding moiety. The toxins catalyse the transfer of an ADP-ribose unit from NAD+ to a target protein.

As used herein, the term "stabilised" refers to the physical stabilisation and/or the functional stabilisation of the bARE protein. The term "stabilized" also refers to storage stability over time, that is the maintenance of physical stability and/or the functional stability over time.

As used herein, the term "physical stabilizing" or "physical stabilisation" is used synonymously with inhibiting, reducing, suppressing, decreasing, diminishing, minimising or lowering precipitation or crystallisation or aggregation or aggregate formation and possible breakdown of the bARE protein. The terms precipitation or crystallisation or aggregation or aggregate formation are used inter-changeable throughout the specification. The present invention includes methods of stabilising a bARE protein using stabilising agents that substantially minimise aggregation or aggregate formation of bARE biological molecules. Substantial minimisation of aggregation or aggregate formation refers to a reduction of aggregation or aggregate formation from about 25% to about 100% compared to controls which do not include the stabilising agents. Preferably, aggregation or breakdown is inhibited by about 50%, more preferably by about 75%, and even more preferably by about 100%.

By "aggregated" or "aggregate formation" is intended a physical interaction between the polypeptide molecules that may result in the formation of oligomers or other higher ordered forms which may remain soluble or which may precipitate or crystallise out of solution. As used herein, the term "oligomer" means a molecule which comprises a plurality of multimer bARE units, such as from about two to about five multimer bARE units.

Methods for monitoring the physical stability of the bARE compositions of the present invention are available in the art, including those methods described in the examples disclosed herein. Thus, bARE aggregate formation, such as AB5 aggregate formation during storage of a liquid pharmaceutical composition of the invention can be readily determined by measuring the change in soluble bARE protein in solution over time. The amount of precipitated polypeptide in solution can be determined qualitatively by visual inspection or determined quantitatively by a number of analytical assays adapted to detection of a precipitated bARE protein. Such assays for quantitative measurement include, for example, reverse phase (RP)-HPLC and UV absorption spectroscopy. While solubility experiments can determine how much of a bARE protein is in solution, other techniques may be required to determine the aggregation state of the protein. It may be important to determine whether a protein is in its native structure in a given formulation and to determine how much of the protein (if any) exists in higher ordered forms such as aggregated forms. Analytical ultracentrifugation is one of the most powerful techniques for elucidating the aggregation state of proteins (see Liu and Shire (1999) *J. Pharm. Sci.* 88:1237-1241). Determination of both soluble and insoluble aggregates during storage in liquid formulations can be achieved, for example, using analytical ultracentrifugation to distinguish between that portion of the soluble polypeptide that is present as soluble aggregates and that portion that is present in the nonaggregate, biologically active molecular form.

The term "functional stabilization" refers to the existence and/or maintenance of a substantially integral form of a bARE protein which is important for the functionality of the bARE protein. As used herein, the term "functional stabilizing" or "functional stabilisation" is used synonymously with the terms inhibiting, reducing, suppressing, decreasing, diminishing, lowering or minimising the dissociation of the bARE protein molecules. The present invention relates to methods of stabilising a bARE protein using agents that substantially minimise dissociation of bARE biological molecules. Substantial minimisation of dissociation refers to a reduction of dissociation from about 25% to about 100% compared to controls which do not include the stabilising agent. Preferably, dissociation is inhibited by about 50%, more preferably by about 75%, and even more preferably by about 100%.

As used herein, the term "substantially integral" refers to an intact, native, non-dissociated structure or conformation of a bARE class protein.

The functional stability of a bARE protein sample may be determined by analysing the bARE sample using the analytical method of the present invention and calculating the degree of integrity of the bARE protein using an Integrity Ratio for the bARE sample According to well-known principles, the relative areas of the peaks representing the $AB_5$ protein and $B_5$ protein subunit in the chromatogram represent the relative proportions of the $AB_5$ and $B_5$ forms in the sample. The relative proportions of the $AB_5$ and $B_5$ forms in the sample can be used to determine the functional stability of the sample.

The term "Integrity Ratio" is used herein to refer to a ratio of integral bARE protein to its dissociated A and B subunit forms in a sample as determined by the percent area under the peaks obtained for the undissociated and dissociated forms of the bARE protein using the analytical method of the present invention. That is, the ratio of intact fully associated bARE protein versus partly dissociated A and B5 pentameric subunit forms and fully dissocated monomeric B forms. The term "Integrity Ratio" is used in connection with a determination of the functional stability of a bARE class protein in accordance with an analytical method of the present invention. A bARE class protein, such as an AB5 protein, is deemed functionally stable or functionally stabilized if it has an Integrity Ratio of from about 10:1 to about 2:1 or from about 8:1 to about 3.5:1 or from about 6:1 to about 4.5:1. It should be understood that in an instance where the amount of $B_5$ dissociated subunit in the sample is so small (for example, less than about 3%), as to be undetectable using the analytical method of the present invention, the Integrity Ratio may not be a meaningful measure, but the bARE protein may still be deemed functionally stable.

In one preferred embodiment, the bARE protein is an AB5 protein.

AB5 Proteins

Preferred bacterial ADP-ribosylating exotoxins (bAREs) for use in the compositions of the present invention include cholera toxin (CT) and the *E. Coli* heat labile toxin (LT). The CT and LT exotoxins are hexamers, composed of a single molecule of an A subunit surrounded by a doughnut-shaped ring composed of 5 molecules of the B subunit. The heat-labile toxin (LT) of enterotoxigenic *E. Coli* (ETEC) is structurally, functionally and immunologically similar to CT and the two toxins cross-react immunologically. Conventionally, CT and LT proteins are termed AB5 proteins. The entire native protein is indicated as AB5, the partly dissociated subunits as A and B5 pentameric form consisting of five identical subunits and the single monomer of the B subunit designated as Bm.

CT is the prototype bacterial enterotoxin. It is a protein built from two types of subunits: a single A subunit of molecular weight 28,000 and five B subunits, each with a molecular weight of 11,600 giving a holotoxin with approx 84, 000 molecular weight. The B subunits are aggregated in a ring by tight noncovalent bonds; the A subunit is linked to and probably partially inserted in the B pentamer ring through weaker noncovalent interactions. The two types of subunits have different roles in the intoxication process: the B subunits are responsible for cell binding and the A subunit for the direct toxic activity. The A subunit contains two domains. The A1 domain possesses ADP-ribosylating activity, which is responsible for the toxicity of the A subunit. The A2 domain interacts with the B oligomer. The enzymatic activity requires the proteolytic cleavage of the loop between the two domains and the reduction of the disulfide bridge between A1-cys187 and A2-cys199. The toxic A subunit induces the enzymatic changes (due to its ADP-ribosylating activity) which lead to fluid secretion and diarrhoea while the non-toxic B subunit is the immunogenic moiety that binds to the GM-1 ganglioside receptor for the toxin on intestinal epithelial cells (Holmgren J Nature (1981) 292; 413).

LT is a type I *Escherichia coli* heat-labile enterotoxin. It consists of (i) an A subunit composed of a single polypeptide chain of 240 amino acids with a molecular weight of around 27 kDa) which contains the toxic ADP-ribosylating activity and (ii) a pentameric ring-shape $B_5$ complex formed by five identical monomers of 103 amino acids each with a molecular weight of around 58.5 Da which contains the ganglioside binding sites. The internal side of the $B_5$ pore is composed of charged aminoacids that interact with the A2 domain of the A subunit, corresponding to the aminoacids 193-240. The rest of the A subunit, A1 domain, retains the catalytic activity. Both the A and B subunits contain a high percentage of positively charged amino acids (subunit A, IP=6.3, Subunit B, IP=8.87 and AB5, IP=8.5).

In certain preferred embodiments, the bacterial ADP-ribosylating exotoxin (bARE) is a cholera toxin (CT) or an *E coli* heat labile enterotoxin (LT) AB5 protein.

In particularly preferred embodiments, the ADP-ribosylating exotoxin peptide subunit coding sequences are obtained or derived from a cholera toxin (CT). In other particularly preferred embodiments, the ADP-ribosylating exotoxin subunit peptide coding sequences are obtained or derived from an *E. Coli* heat labile enterotoxin (LT), for example LT1 or LT2 AB5 proteins.

Separation of $AB_5$ and $B_5$ Forms of an $AB_5$ Class Protein

It has now been unexpectedly found that bARE class proteins, such as the native intact $AB_5$ molecule and partly dissociated $B_5$ forms of the $AB_5$ class protein can be separated under non-dissociating conditions which differentiate between integral and dissociated bARE class proteins. Generally, a suitable material for separating a native, intact bARE molecule, such as an AB5 molecule and its dissociated subunit forms, is a charged polymer separation material whereby the different forms of the bARE molecule applied to the separation material may be separated with an ionic buffer. Preferably, the charged polymer column separation material is a hydrogel separation material.

Hydrogel compositions are well-known in the biomedical arts, and are commonly used as substrates for cell and tissue culture, impression materials for prosthetics, wound-packing materials, or as solid phase materials in size exclusion or affinity chromatography applications. For example, nonporous, deformed and/or derivatized agarose hydrogel compositions have been used in high-performance liquid chromatography and affinity chromatography methods (Li et al (1990) Preparative Biochem. 20:107-121), and superporous agarose hydrogel beads have been used as a support in hydrophobic interaction chromatography (Gustavsson et al (1999) J. Chromatography 830:275-284).

The hydrogels useful in this invention may be naturally-occurring (e.g., agarose and alginate) or may be synthetically prepared or modified. A hydrogel is a material comprising a macromolecular three-dimensional network that allows it to swell when in the presence of water, to shrink in the absence of (or by reduction of the amount of) water but not dissolve in water. The swelling, i.e., the absorption of water, is a consequence of the presence of hydrophilic functional groups attached to or dispersed within the macromolecular network. Cross-links between adjacent macromolecules result in the aqueous insolubility of these hydrogels. The cross-links may be due to chemical (i.e., covalent) or physical (i.e., Van Der Waal forces, hydrogen-bonding, ionic forces, etc.) bonds. A characteristic of a hydrogel that is of particular value is that the material retains the general shape, whether dehydrated or hydrated. Thus, if the hydrogel has an approximately spherical shape in the dehydrated condition, it will be spherical in the hydrated condition.

Synthetically prepared hydrogels generally are prepared by polymerizing a monomeric material to form a backbone and cross-linking the backbone with a cross-linking agent. Common hydrogel monomers include but are not limited to the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide.

Some synthetic hydrogels are made by free radical polymerization of hydrophilic vinyl monomers. The initiation step is the formation of a free radical, usually by the addition of azo-type initiators such as 2,2'-azobis(2-methylpropanenitrile) or peroxide initiators such as benzoyl peroxide. Ultraviolet light or gamma radiation can also initiate the reaction. Propagation takes place by free radical reaction with the vinyl monomer groups. Normally a portion of the reaction mixture consists of difunctional vinyl compounds that provide a degree of cross-linking. The hydrophilicity of the gel is usually controlled by copolymerizing a hydrophilic and hydrophobic vinyl monomer into the gel. The permeability of a hydrogel is determined, inter-alia, by the extent of cross-linking, the degree of hydration of the gel, and the nature of the permeant.

Preferably the separation material is a hydroxylated polymethacrylate (HEMA) material.

The quantity and type of solvent used in the polymerization mix can substantially affect the quality of the gel produced. For example, poly(hydroxyethyl methacrylate), or poly(HEMA), only absorbs 35-40 wt % of water, and therefore poly(HEMA) prepared from polymerization reaction mixtures containing a greater amount of water contain water-filled voids and are translucent or opaque in appearance. Cross-linking usually reduces the water sorption of the polymer.

Further discussion of synthetic hydrogels may be found at "Controlled Release of Biologically Active Agents" by Richard Baker, A Wiley-Interscience Publication, John Wiley & Sons, pp. 101-104 and 178-183 and in U.S. Published patent application No. 20020061336. These references are incorporated herein by reference. The polymer separation material can have a particle size of from about four to about ten microns and porosity of from about 250 Å. Preferably the particle size is about 6 microns. The pore size may be dependent on the size of the bARE molecule which is being analysed. The buffer is of suitable ionic strength and the buffer system is capable of maintaining the pH of the eluting buffer within the range of from about 7.0 to about 8.0. Preferably, the pH of the eluting buffer is in the range of from about 7.0 to about 7.5. More preferably, the pH of the eluting buffer is in the range of from about 7.0 to about 7.2.

In a specific preferred embodiment, the gel filtration-high performance liquid chromatography column comprises hydroxylated polymethacrylate separation material having residual carboxyl groups, for example, a Waters Ultrahydrogel 250 size exclusion column, available from Waters, Milford, Mass. The Ultrahydrogel 250 has a particle size of about 6 microns and a porosity of about 250 Å. The ionic buffer is of suitable ionic strength, composition and pH, for example, from about 100-400 mM of a substantially neutral phosphate/sulfate buffer. For example, in a preferred embodiment, the buffer may be, for example, potassium phosphate (KPi) and $Na_2SO_4$, in particular KPi 200 mM and $Na_2SO_4$ 100 mM, pH 7.2. In one preferred embodiment, the eluting buffer comprises stabilising agents compatible with the bARE molecule being analysed.

For the Ultrahydrogel 250/KPi 200 mM and $Na_2SO_4$ 100 mM, pH 7.2 system, the column dimensions are 7.8 mm interior diameter×300 mm length. A suitable elution flow rate is from about 0.25 to about 0.7 ml/min, preferably for example about 0.5 ml/min. Detection may be conducted with a photodiode array (PDA) detector operating at 214 and 280 nm. Chromatographic run time is generally no more than 30 minutes.

Using such a chromatographic system, it is possible to obtain good peak separation between $AB_5$ and $B_5$ forms of an $AB_5$ class protein. Good peak separation allows reliable detection of $AB_5$ and $B_5$ forms in a sample of $AB_5$ class protein, which in turn allows determination of whether or not the sample is in a substantially intact or associated, partly dissociated or in a substantially dissociated form. The detection of intact (integral) $AB_5$ protein in the column eluate, represented by a substantially single peak in the resulting chromatogram with a retention time (RT) corresponding to $AB_5$, indicates substantial functional stability of the $AB_5$ protein sample run on the column. The detection of both intact $AB_5$ protein and $B_5$ protein subunit in the column eluate, represented by a two distinct peaks in the resulting chromatogram with retention times (RTs) corresponding to $AB_5$ and 135, indicates a partial dissociation of the $AB_5$ protein sample. The detection of $B_5$ protein subunit in the column eluate, represented by a single peak in the resulting chromatogram with a retention time (RT) corresponding to $AB_5$, indicates substantial dissociation of the $AB_5$ protein sample.

Good peak separation also allows reliable quantification of the proportions of $AB_5$ and $B_5$ forms in a sample of $AB_5$ class protein, which in turn allows determination of the degree of integrity of the $AB_5$ class protein, or, from another perspective, a measure of the functional stability of the sample. According to well-known principles, the relative areas of the peaks representing the $AB_5$ protein and $B_5$ protein subunit in the chromatogram represent the relative proportions of the $AB_5$ and $B_5$ forms in the sample. The relative proportions of the $AB_5$ and $B_5$ forms in the sample can be used to determine the functional stability of the sample.

This measurement of sample stability may be presented as an Integrity Ratio. The term "Integrity Ratio" is used herein to refer to a ratio of integral $AB_5$ protein to $B_5$ subunit in a sample. In accordance with the present invention, an $AB_5$ class protein is deemed functionally stable or functionally stabilized if it has an Integrity Ratio of from about 10:1 to about 2:1 or from about 8:1 to about 3.5:1 or from about 6:1 to about 4.5:1 Preferably the Integrity Ratio for the AB5 protein is at least 5:1.

It should be understood that in an instance where the amount of $B_5$ subunit in the sample is so small as to be undetectable using the analytical method of the present invention, the Integrity Ratio may not be a meaningful measure, but the $AB_5$ protein is deemed stable. However, the sensitivity of the method is such that levels of partially dissociated B5 subunit as low as 3% are detectable using the analytical method of the present invention. In comparison, prior art methods, such as SDS-PAGE, which do not maintain the structural integrity of the intact protein, will generally not detect less than 20% of a dissociated B5 subunit form.

The ability to reliably and quantifiably separate $AB_5$ and $B_5$ forms of an $AB_5$ class protein using a non-dissociating technique, such as a liquid chromatography technique, such as a gel-filtration high-performance liquid chromatography material (GF-HPLC) configured to resolve the $AB_5$ protein from the $B_5$ protein subunit enables a variety of useful assays and other techniques useful in drug, particularly vaccine, development and general research on protein structure and stability. Although high-performance aqueous size-exclusion chromatography (HPASEC) is known in the art (see for example, Perez-Paya et al (1991) J of Chromatography 548: 93-104), the application of HPASEC for the separation of $AB_5$ and $B_5$ forms of an $AB_5$ class protein has neither been disclosed nor been suggested in the prior art. Without wishing to be bound by theory, the elution mechanism of most biopolymers on HPASEC supports deviates from a pure size-exclusion mechanism, mainly owing to a number of secondary effects, including ion exclusion and ion exchange, hydrophobic interaction and hydrogen bonding originating from specific solute-matrix interactions. The validity of the separation system can be defined by chromatogram peak attribution which can be conducted by any one of following techniques including SDS-PAGE, apparent molecule weight determination, light scattering (MALLS) and Liquid Chromatography Electrofocusing Mass Spectrometry (LC-ESI-MS). Indeed as the Examples demonstrate, evidence that the integrity of the AB5 protein has been maintained has been verified using techniques such as Dimensional Analyses, Light Scattering Analyses (MALLS) and LC-ESI-MS.S Stabilization Agent Assay and Identified Stabilization Agents The identification of agents capable of stabilizing a bARE protein stabilizing agent, such as an $AB_5$ class protein stabilizing agent, facilitates the use of, for example, $AB_5$ class proteins in compositions, such as vaccines, where the integrity of the intact bARE protein is important for the efficacy of the therapeutic end product. The separation method of the present invention may be leveraged to provide an assay for the identification of candidate stabilization agents. The screening of candidate stabilizing agents is a well known area, and high throughput implementations of screening assays may be readily developed given a particular screening methodology. The present invention provides such a methodology.

The screening assay of the present invention is a method of identifying a bARE protein, such as an $AB_5$ protein stabilization agent. When applied to an AB5 protein, the assay involves combining a candidate stabilization agent with an $AB_5$ class protein to form an $AB_5$ protein sample. A candidate stabilization agent may be a single compound or combination of compounds in a certain condition regime, e.g., pH, concentration, etc. By way of example, the candidate stabilizing agent may be selected from the group consisting of candidate stabilizing buffers operating in different pH ranges or candidate stabilizing agents selected from the group consisting of amorphous sugars, crystalline sugars, or various charged and non-charged surfactant agents such as detergents. A stabilization agent candidate that stabilizes or enhances the physical stabilization of the $AB_5$ protein sample is an $AB_5$ protein physical stabilization agent.

When the sample is applied to a gel filtration-high performance liquid chromatography column configured to resolve, for example, an AB5 protein from the $B_5$ protein subunit, the column is eluted with an ionic buffer, as described above in connection with the separation method. Also as described above, one or more of the substantially intact (non-dissociated) $AB_5$ proteins and/or partially dissociated $B_5$ protein subunits and/or substantially dissociated Bm monomer subunits in the column eluate is detected, and, based on the results of this detection, it is determined whether the candidate stabilization agent is capable of stabilising an $AB_5$ protein in terms of functionally stabilizing the AB5 protein. A stabilization agent candidate that stabilizes or enhances the functional stabilization of the $AB_5$ protein sample is an $AB_5$ protein functional stabilization agent.

The determination of whether the candidate stabilization agent stabilizes or enhances the stabilization of the $AB_5$ protein may include calculating an Integrity Ratio for the protein sample, the Integrity Ratio being a ratio of substantially integral $AB_5$ protein to partially dissociated $B_5$ subunit and/or substantially dissociated Bm momomeric subunit and comparing the Integrity Ratio of the sample to an Integrity Ratio for a control without the stabilization agent candidate. The Integrity Ratio may also be used to quantify the extent of stabilization conferred by an identified stabilization agent.

Libraries of stabilization agent candidates may be assayed according to this method in a high throughput manner in order to efficiently identify $AB_5$ protein stabilization agents. The stabilization agent candidates may be combined with a variety of a bARE proteins, such as an $AB_5$ proteins, to determine differences in the stabilizing ability and extent of a given stabilizing agent candidate among different $AB_5$ protein samples. Typically the analytical method of the present invention is used on a stabilised, preferably a physically stabilized bARE protein in order to identify agents capable of functionally stabilizing a bARE protein. Alternatively, the analytical method of the present invention may be used to determine whether identified physical stabilizing agents have an impact on the functional stability of a bARE protein.

As the Examples demonstrate, various buffers, such as Acetate, pH 5.5, Citrate, pH 6.5, Phospate and Tris buffers (pH range of about 6-8) were chosen. The NaCl concentration was varied in the range of 0-0.5M; the pH was varied in the range of 5.5-7.5. Various additives such as sugars, detergents, chelators and aminoacids were used. As the physical stabilisation of a protein may be a function of its protein concentration (that is, as the concentration of bARE protein, such as an AB5 protein increases, then the likelihood of the protein precipitation or crystallisation increases), the effect of candidate stabilizing agents was evaluated using a protein concentration range of from 0.8-1.2 mg/ml and from about 1 mg/ml to about 4 mg/ml for purified concentrated bulk of an AB5 mutant, such as LTK63 (which is discussed below) in all the storage buffers used.

Some of the candidate amino acids which were evaluated as stabilizing agents are set out in the following Table 8. As Table 8 shows, selections of amino acids as candidate stabilizing agents can be made on the basis of their polarity, charge, solubility, hydrophobicity, hydrophilicity and/or the amphipathic nature of the residues. For example, negatively charged amino acids include aspartic acid and glutamic acid. Positively charged amino acids include lysine and Arginine. Amino acids with uncharged polar head groups having similar hydrophilicy include leucine, isoleucine, valine, glycine, alanine, asparagines, glutamine, serine, threonine, phenylalanine and tyrosine.

TABLE 8

| Property | | Amino acids |
|---|---|---|
| small | | Ala, Gly |
| acidic/amide | | Asp, Glu, Asn, Gln |
| charged | negative | Asp, Glu |
| | positive | Lys, Arg |
| polar | | Ala, Gly, Ser, Thr, Pro |
| hydrophobic | | Val, Leu, Ile, Met |
| size | big | Glu, Gln, His, Ile, Lys, Leu, Met, Phe, Trp, Tyr |
| | small | Ala, Asn, Asp, Cys, Gly, Pro, Ser, Thr, Val |
| aliphatic | | Ile, Leu, Val |
| aromatic | | His, Phe, Tyr, Trp |

Some of the candidate sugars which were evaluated were selected from amorphous excipients such as dextrose, sucrose, lactose, trehalose and galactose. Some other candidate sugars which were evaluated were selected from crystalline excipients such as sugar alcohols including mannitol, sorbitol and allitol. These candidate agents were selected because it is known in the art that these sugars are capable of stabilizing proteins used as pharmaceutical agents during the spray-freeze-drying process and during long-term storage (see for example WO 02/101412). However, there are some conflicting reports on the benefits of an amorphous excipient in terms of stabilisation.

Indeed, some studies have shown that the addition of amorphous excipients to protein solutions can actually destabilise a protein through interactions between the excipient and the protein (see for example, Pike et al Biopharm 1990 3: 2629 and WO 01/41800).

As the Examples demonstrate, not all of the candidate stabilizing agents were useful in stabilizing the bARE protein of the present invention. By way of example, whilst the addition of 5% sucrose to PBS seemed to protect an AB5 mutant, such as LT K63, from dissociation in a freeze/thawing cycle, the storage of LTK63 in PBS at −20° C. plus 5% sucrose for not less than one year resulted in some recurrance of protein dissociation. However, some agents were identified which were capable of stabilizing the bARE protein as determined using the methods of the present invention.

Accordingly, in one aspect, there is provided the use of an uncharged agent or an analogue thereof to stabilize a bARE protein, such as an AB5 protein.

Preferably the use of the uncharged agent or the analogue thereof is to functionally stabilise a bARE protein, such as an AB5 protein.

As used herein, the term "uncharged agent" means an agent having a net amount of positive or negative charge. The term "uncharged agent" also includes By "analogue" is intended any variants, homologues, analogues, derivatives or fragments thereof of an uncharged agent which may have one or more substitutions, insertions, or deletions and which brings about the desired effect of minimizing dissociation of the bARE protein and thus maintaining the substantial integrity of the bARE protein, during storage over a period of time. Suitable analogues include but are not limited to derivatives of the uncharged agents described below.

The inclusion of an uncharged agent to functionally stabilize a bARE protein, such as an AB5 protein is advantageous because it enhances the stable association of the subunit forms. This is the first time that an agent has been identified which can functionally stabilize or enhance the functional stabilizing of a bARE protein. Up until now, no method was available for evaluating the functional stability of a bARE protein, such as an AB5 protein, without loss of the integral structure. As no analytical method was available, no such functional stabilizing agents could be identified.

Preferably the uncharged agent is a zwitterionic agent.

Preferably the zwitterionic agent is selected from the group consisting of a zwitterionic detergent and a zwitterionic non-detergent compound.

Preferably the zwitterionic agent is a zwitterionic detergent.

Zwitterionic detergents, also known as zwittergents are unique in that they offer the combined properties of ionic and non-ionic detergents. Like non-ionic detergents, the zwittergents, do not posess a net charge, they lack conductivity and electrophoretic mobility and do not bind to ion-exchange resins.

Preferably the zwitterionic detergent is a bile salt derivative.

As used herein, the term "bile salt derivative" refers to a derivative of cholesterol with a carboxylic acid. Examples of bile salt derivative include but are not limited to cholic acid and deoxycholic acid.

Preferably the zwitterionic detergent, also known as a zwittergent, is selected from the group consisting of ASB-14, ASB-16, CHAPS, CHAPSO, DDMAB, DDMAU, Epigen BB Detergent, Lauryldimethylamine Oxide (LDAO), Zwittergent 3-08, 3-10, 3-12, 3-14, and 3-16 which are set out in FIG. 16. The structures of CHAPS, CHAPSO and other Zwittergents outlined above is set out in FIG. 17 taken from "Detergents—A guide to the properties and uses of detergents in biological systems" by Srirama M Bhairi (2001) and available from Calbiochem (Doc no CB0068-401).

Preferably the uncharged detergent is a zwittergent such as CHAPS (3-(3-Cholamidopropyl)-dimethylammonio-1-propanesulfonate). CHAPS is a zwitterionic synthetic derivative of a bile salt. The structure of CHAPS is set out in FIG. 17. CHAPS is available from a number of commercial sources including Calbiochem, an affiliate of Merck and Sigma, Aldrich.

Without wishing to be bound by theory, zwittergents, such as CHAPS, are advantageous because they are less denaturing than the Zwittergent® 3-X series, possibly owing to their rigid steroid ring structure. Thus, zwittergents, such as CHAPS, may enhance the stable association of the A and B subunits.

Preferably the uncharged detergent is a zwittergent such as CHAPSO (3-(3-Cholamidopropyl)-dimethylammonio-2-hydroxypropanesulfonate). The CHAPSO structure is also set out in FIG. 17. CHAPSO is available from a number of commercial sources including Calbiochem, an affiliate of Merck and Sigma, Aldrich.

Preferably the zwitterionic agent is a non-detergent sulfobetaine (NDSB).

A NDSB is a zwitterionic compound. Like zwittergents, NDSBs carry the sulfobetaine hydrophilic head group. However, in contrast to zwittergents, NDSBs do not behave like detergents. Recently, NDSBs have found use in several applications including isolation of membrane proteins. They have also been used in renaturation and refolding of chemically and thermally denatured proteins. It has been hypothesized that the hydrophobic group, although short, interacts with the hydrophobic regions of a protein to prevent aggregation during renaturation.

In another embodiment of the present invention, analogues of the zwitterionic compounds may be prepared and used in the bARE composition using techniques which are known to the person skilled in the art.

Following the protocols disclosed, for example, in Examples below, the skilled person may assess a range of desired concentrations of the zwitterionic agent described herein. Preferably the amount of zwitterionic agent incorporated into the composition is within a concentration range of from about 0.05% to about 0.5% by weight per volume (w/v), preferably from about 0.1% to about 0.4%, more preferably from about 0.2% to about 0.35%, even more preferably about 0.25%. For ease of reference, 0.05% (w/v) CHAPS is equivalent to 0.81 mM CHAPS and 0.25% CHAPS is equivalent to 4.06 mM CHAPS.

According to a further aspect, there is provided the use of a charged agent to stabilize a bARE protein, preferably an AB5 protein.

Preferably the charged agent is a charged amino acid base.

As used herein, the term "charged amino acid" means an amino acid with a charged side chain such as that found in amino acids such as arginine, lysine, aspartic acid, and/or glutamic acid.

By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms.

The inclusion of a charged amino acid base to physically stabilize a bARE protein, such as an AB5 protein, is advantageous because it enhances the stabilization and/or minimises the aggregation and/or aggregate formation.

Even more preferably, the charged amino acid is a positively charged amino acid.

As used herein, the term "positively charged amino acid" means an amino acid with a positively charged side chain such as that found in amino acids such as Arginine or Lysine.

Preferably the positively charged amino acid is Arginine.

The identification of Arginine as a stabilizing agent is unexpected but its inclusion in a bARE composition is advantageous because it appears to enhance the solubility of the bARE protein, such as an AB5 protein.

Arginine is an essential amino acid which has a positively charged guanidino group. It is generally denoted by the three letter code ARG or the one letter symbol R. Its IUPAC name is 2-amino-5-guanidino pentanoic acid. The side chain guanidino group is positively charged at pH 7; hence Arginine is a "basic" amino acid and is extremely hydrophilic. The line structure for Arginine is: HN=C(NH2)—NH—(CH2)3—CH(NH2)—COOH

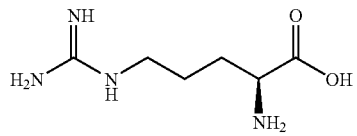

There are 6 codons in the genetic code for arginine which are: AGA, AGG, CGA, CGC, CGG, CGT.

Compositions of the invention may also be formulated with analogues of these preferred amino acids.

By "amino acid analogue" is intended a derivative of the naturally occurring amino acid or a fragment thereof which may have one or more amino acid substitutions, insertions, or deletions and which brings about the desired effect of minimising aggregate formation of the bARE protein during storage of the composition. Suitable arginine analogues include, for example, aminoguanidine and N-monoethyl L-arginine. Other analogues may include, without limitation, dipeptides and tripeptides that contain Arginine. As with the preferred amino acids, the amino acid analogues are incorporated into the compositions in either their free base form or their salt form.

The term "amino acid analogue" also includes stereoisomers of an amino acid. Any stereoisomer (i.e., L, D, or DL isomer) of an amino acid, or combinations of these stereoisomers, may be present in the bARE compositions of the present invention so long as the particular amino acid is present either in its free base form or its salt form. Preferably the L stereoisomer is used.

Following the protocols disclosed, for example, in Examples 4-12 below, the skilled artisan may assess a range of desired concentrations of the amino acid base described herein. Preferably the amount of amino acid base incorporated into the composition is within a concentration range of from about 100 mM to about 400 mM, preferably from about 130 mM to about 375 mM, more preferably from about 150 mM to about 350 mM, even more preferably from about 175 mM to about 325 mM, still more preferably from about 180 mM to about 300 mM, even more preferably from about 190 mM to about 280 mM, most preferably from about 200 mM to about 260 mM, depending upon the protein present in the composition.

In some situations, a bARE protein may be functionally stable (for example, its integrity may be maintained) but it may not be physically stable (for example, it may be precipitated out of solution). In other situations, a bARE protein may be physically stable (for example, it may be in solution) but it may not be functionally stable (ie it may be partially dissociated into AB5 and B5 forms).

Thus, as described above, in one aspect, the present invention provides for stabilising agents which can selectively stabilise a bARE protein with respect to either physical stabilisation or functional stabilization.

In addition, in another aspect, the present invention also provides for the use of a combination of charged and uncharged stabilizing agents to stabilise a bARE protein.

Preferably, the uncharged stabilizing agent is a zwitterionic agent, preferably CHAPS.

Preferably the charged stabilizing agent is a charged amino acid, preferably Arginine.

As the Examples demonstrate, it has been determined that a charged amino acid, such as L-Arginine or derivatives of L-Arginine, such as Arginine phosphate, are useful stabilization agents for LTK63, in particular at concentration of from about 100 to about 400 mM. Another useful stabilizing agent comprises a combination of a charged amino acid, such as L-Arginine or Arginine phosphate and a sulfobetaine zwitterionic detergent, such as CHAPS (3-[(3-Cholamidopropyl)dimethylammonio]-1-propanesulfonate), in particular about 0.05% CHAPS with about 200 mM arginine phosphate. In terms of functional stabilization capability, these stabilization agents can achieve an Integrity Ratio of from about 10:1 to about 2:1 or from about 8:1 to about 3.5:1 or from about 6:1 to about 4.5:1 for LTK63. Preferably the Integrity Ratio for LTK63 is about 10:1.

Without wishing to be bound by theory, the increased stability of the bARE composition by the inclusion of amino acids may be achieved through the influence of the amino acid on stability of the bARE polypeptide, more particularly its influence on bARE protein precipitation. Furthermore, incorporation of a zwitterionic agent as defined herein within the bARE polypeptide composition results in a composition comprising a bARE protein that is maintained substantially in their intact native form and whose integrity can be measured using the analytical method of the present invention.

The combination of a charged amino acid, such as amino acid arginine, lysine, aspartic acid, or glutamic acid in its free base form or in its salt form with an uncharged zwitterionic agent results in a bARE composition is advantageous because it results in increased stability relative to a bARE composition prepared without the combination of these two components. The synergistic stabilizing effect achieved from the combination of an amino acid base and a zwitterionic agent is wholly unexpected in view of the disclosures in the prior art. Moreover, this stabilized composition is advantageous because stability can be achieved in the absence of Human Serum Albumin (HAS) as either a stabilizing and/or solubilizing agent.

Having identified the advantages of preparing bARE polypeptide compositions of the invention with an amino acid base and an zwitterionic agent, it is within skill in the art to determine, without undue experimentation, preferred concentrations of each of these components to be incorporated into a bARE composition comprising a therapeutically active bARE polypeptide of interest that exhibits aggregate formation as described herein to achieve increased polypeptide stability during storage of that composition.

Following the protocols disclosed, for example, in Example 1 below, the skilled person may assess a range of desired concentrations of the amino acid base and the zwitterionic agent described herein. Preferably the amount of amino acid base incorporated into the composition is within a concentration range of from about 100 mM to about 400 mM, preferably from about 130 mM to about 375 mM, more preferably from about 150 mM to about 350 mM, even more preferably from about 175 mM to about 325 mM, still more preferably from about 180 mM to about 300 mM, even more preferably from about 190 mM to about 280 mM, most preferably from about 200 mM to about 260 mM, depending upon the protein present in the composition.

Following the protocols disclosed, for example, in Examples 4-12 below, the skilled person may assess a range of desired concentrations of the zwitterionic agent described herein. Preferably the amount of zwitterionic agent incorporated into the composition is within a concentration range of from about 0.05% to about 0.5%, preferably from about 0.1% to about 0.4%, more preferably from about 0.2% to about 0.35%, even more preferably about 0.25%.

Thus, in another embodiment of the invention, the stabilized composition comprising the bARE protein, arginine base at a concentration of about 150 mM to about 350 mM, and a zwitterionic agent at a concentration of from about 0.05% to about 0.5%. In a preferred embodiment, the arginine base is present in the bARE, composition at a concentration of about 200 mM and zwitterionic agent, such as CHAPS is present at a concentration of about 0.25%. This preferred bARE composition has a pH of about 7.2. The concentration of the bARE protein or variant thereof in these compositions is about 0.01 mg/ml to about 2.0 mg/ml, preferably about 0.02 mg/ml to about 1.0 mg/ml, more preferably about 0.03 mg/ml to about 0.8 mg/ml, most preferably about 0.03 mg/ml to about 0.5 mg/ml.

The stabilized compositions of the invention may contain other compounds that increase the effectiveness or promote the desirable qualities of the bARE polypeptide of interest that serves as a therapeutically active component so long as the stabilizing effects achieved with the amino acid base and the zwitterionic agent is not adversely affected. The composition must be safe for administration via the route that is chosen, it must it must be sterile, and must retain its desired therapeutic activity.

The bARE composition may additionally comprise a solubilizing agent or solubility enhancer that contributes to the protein's solubility beyond the enhanced solubility obtained using the low-ionic-strength formulations disclosed herein. Additional suitable solubilizing agents are discussed in U.S. Pat. Nos. 4,816,440; 4,894,330; 5,004,605; 5,183,746; 5,643,566; and in Wang et al. (1980) J. Parenteral Drug Assoc. 34:452-462; herein incorporated by reference.

The bARE composition may additionally comprise non-ionic detergents. Examples of non-ionic detergents include but are not limited to detergents containing uncharged, hydrophilic head groups that consist of either polyoxyethylene moieties such as but not limited to Brij® and Triton® (such as for example, Triton-X, NP-40, Brij, Tween) or glycosidic groups such as but not limited to octyl glucoside and dodecyl maltosides (such as, for example, Octyl-B-Thioglucopyranoside). Without wishing to be bound by theory, non-ionic detergents are advantageous because they are considered to be "mild" detergents which are considered to be non-denaturant and are widely used in the isolation of membrane proteins in their biologically active form because they seldom denature proteins while solubilising them.

Storage Stability

Increasing stability of a bARE protein or variant thereof by incorporating an amino acid base, or an amino acid base base plus one or more additional stabilizing agents described herein, in combination with the zwitterionic agent leads to an increase in stability of the bARE protein composition during storage. Thus, the invention also provides a method for increasing storage stability of a bARE composition when that composition comprises a bARE protein that forms aggregates during storage.

By "increasing storage stability" is intended that aggregate formation and/or dissociation of the bARE polypeptide during storage of the bARE composition is minimised relative to aggregate formation and/or dissociation of the bARE polypeptide during storage in the absence of one or more stabilizing agent described herein.

Minimising aggregate formation and/or dissociation of a bARE protein with addition of an amino acid base or zwitterionic agent may occur in a concentration dependent manner. That is, increasing concentrations of amino acid base and/or zwitterionic agent may lead to increased stability of the bARE polypeptide in a composition when that polypeptide normally exhibits aggregate formation and/or dissociation during storage in a composition in the absence of the amino acid base and/or zwitterionic agent. Determination of the amount of a particular amino acid base and/or zwitterionic agent to be added to a bARE composition to minimize aggregate formation and/or dissociation thereby increasing polypeptide stability, and thus increasing storage stability of the composition, can readily be determined for any particular bARE polypeptide of interest without undue experimentation using methods generally known to one of skill in the art.

It is also desirable to increase the storage stability of a bARE composition over time.

The bARE composition of the present invention demonstrates increased storage stability.

Preferably the increased storage stability is observed over a period of from about 4 months to about 8 months.

Preferably the increased storage stability is observed over a period of about 1 year.

Preferably the bARE composition has a shelf-life of at least about 18 months, more preferably at least 20 months, still more preferably at least about 22 months, most preferably at least about 24 months when stored at 2-8.

Storage stability of a bARE compositions made in accordance with the methods of the invention can be assessed using standard procedures known in the art. Typically, storage stability of such compositions is assessed using storage stability profiles. These profiles are obtained by monitoring changes in the amount of bARE protein present in its nonaggregated, non-dissociated biologically active molecular form and its potency over time in response to the variable of interest, such as pH concentration, stabilizing agent, concentration of stabilizing agent, etc., as demonstrated in the Examples below. These stability profiles may be generated at several temperatures representative of possible storage conditions, such as freezing temperature, refrigerated temperature, room temperature, or elevated temperature, such as at 40-50° C. Storage stability may then be compared between profiles by determining, for example, half-life of the nonaggregated, biologically active, non-dissociated molecular form of the bARE polypeptide of interest.

By "half-life" is intended the time needed for a 50% decrease in the nonaggregated, biologically active molecular form of the polypeptide of interest. Compositions comprising an Arginine base and a zwitterionic agent prepared in accordance with the methods of the present invention will have a half life that is at least about two-fold to about ten-fold greater, preferably at least about three-fold to at least about 10-fold greater, more preferably at least about four-fold to about ten-fold greater, most preferably at least about five-fold to about ten-fold greater than the half-life of a composition prepared in the absence of an amino acid base base, or an amino acid base plus one or more of the additional stabilizing agents described herein, in combination with a zwitterionic agent. For purposes of the present invention, a composition having increased storage stability as a result of being prepared in accordance with the present invention is considered a "stabilized" bARE composition.

Without wishing to be bound by one theory, increased storage stability of the stabilized bARE polypeptide-containing compositions of the invention may also be associated with the inhibitory effects of the amino acid base on deamidation of glutamine and/or asparagine residues within the therapeutically active bARE polypeptide during storage. The effect of a particular amino acid base on deamidation of these residues during storage in a bARE composition can readily be determined by monitoring the amount of bARE polypeptide present in its deamidated form over time. Methods for measuring molecular species, that is, native or deamidated, of a particular bARE polypeptide are generally known in the art. Such methods include chromatographic separation of the molecular species and identification using polypeptide molecular weight standards, such as with RP HPLC.

bARE Protein

As used herein, the term "bARE protein" includes, but is not limited to, proteins, nucleic acids. bARE proteins may be used individually or in combination with other biological molecules.

The term "protein" as used herein encompasses naturally occurring (native), synthetic, and recombinant polypeptides and proteins, and biologically active variants and analogues thereof, as qualified elsewhere herein. The term "protein" also includes polypeptides and peptides which are conjugated to other biological molecules. By "therapeutically active component" is intended the protein or polypeptide which is specifically incorporated into the bARE composition of the present invention to bring about a desired therapeutic response with regard to treatment, prevention, or diagnosis of a disease or condition within a subject when the bARE composition is administered to that subject.

Polypeptides of the invention can be prepared by various means (e.g. recombinant expression, purification from cell culture, chemical synthesis, etc.) and in various forms (e.g. native, fusions, non-glycosylated, lipidated, etc.). They are preferably prepared in substantially pure form (i.e. substantially free from other host cell proteins). The invention also provides a process for producing a polypeptide of the invention, comprising the step of culturing a host cell transformed with nucleic acid of the invention under conditions which induce polypeptide expression.

As used herein, the term "nucleic acid" refers to oligonucleotides and polynucleotides, and includes DNA and RNA. The term "nucleotide sequence (NOI)" is synonymous with the term "polynucleotide" or "nucleic acid". The NOI may be DNA or RNA of genomic or synthetic or of recombinant origin. The NOI may be double-stranded or single-stranded whether representing the sense or antisense strand or combinations thereof. For some applications, preferably, the NOI is DNA. For some applications, preferably, the NOI is prepared by use of recombinant DNA techniques (e.g. recombinant DNA). For some applications, preferably, the NOI is cDNA. For some applications, preferably, the NOI may be the same as the naturally occurring form. The term "nucleic acid" includes DNA and RNA, and also their analogues, such as those containing modified backbones (e.g. phosphorothioates, etc.), and also peptide nucleic acids (PNA), etc. The invention includes nucleic acid comprising sequences complementary to those described above (e.g. for antisense or probing purposes).

Nucleic acid according to the invention can be prepared in many ways (e.g. by chemical synthesis, from genomic or cDNA libraries, from the organism itself, etc.) and can take various forms (e.g. single stranded, double stranded, vectors, probes, etc.). They are preferably prepared in substantially pure form (i.e. substantially free from other proteins or host cell nucleic acids).

Biologically active variants of a bARE protein that serves as a therapeutically active component in the compositions of the invention are also encompassed by the term "bARE protein" as used herein. Such variants should retain the desired biological activity of the native bARE protein such that the composition comprising the variant polypeptide has the same therapeutic effect as the composition comprising the native polypeptide when administered to a subject. That is, the variant polypeptide will serve as a therapeutically active component in the composition in a manner similar to that observed for the native bARE protein.

Variants may include but are not limited to situations where the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of polypeptide used herein so long as the activity of the polypeptide is not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy activity do not remove the polypeptide sequence from the definition of polypeptide of interest as used herein.

The art provides substantial guidance regarding the preparation and use of polypeptide variants. In preparing the polypeptide variants, one of skill in the art can readily determine which modifications to the native protein nucleotide or amino acid sequence will result in a variant that is suitable for use as a therapeutically active component of a pharmaceutical composition of the present invention and whose aggregate formation is decreased by the presence of an amino acid base and an acid substantially free of its salt form, the salt form of the acid, or a mixture of the acid and its salt form, as described herein. By way of example, methods are available in the art for determining whether a variant polypeptide retains the desired biological activity, and hence serves as a therapeutically active component in the composition. Biological activity can be measured using assays specifically designed for measuring activity of the native polypeptide or protein, including assays described in the present invention. Additionally, antibodies raised against a biologically active native polypeptide can be tested for their ability to bind to the variant polypeptide, where effective binding is indicative of a polypeptide having a conformation similar to that of the native polypeptide.

Suitable biologically active variants of a native or naturally occurring polypeptide of interest can be fragments, analogues, and derivatives of that polypeptide. By "fragment" is intended a polypeptide consisting of only apart of the intact polypeptide sequence and structure, and can be a C-terminal deletion or N-terminal deletion of the native polypeptide.

By "analogue" is intended an analogue of either the native polypeptide or of a fragment of the native polypeptide, where the analogue comprises a native polypeptide sequence and structure having one or more amino acid substitutions, insertions, or deletions. "Muteins", such as those described herein, and peptides having one or more peptoids (peptide mimics) are also encompassed by the term analogue (see, for example, PCT International Publication No. WO 91/04282).

By "derivative" is intended any suitable modification of the native polypeptide of interest, of a fragment of the native polypeptide, or of their respective analogues, such as glycosylation, phosphorylation, or other addition of foreign moieties, so long as the desired biological activity of the native polypeptide is retained. Methods for making polypeptide fragments, analogues, and derivatives are generally available in the art. For example, amino acid sequence variants of the polypeptide can be prepared by mutations in the cloned DNA sequence encoding the native polypeptide of interest.

Methods for mutagenesis and nucleotide sequence alterations are well known in the art. See, for example, Walker and Gaastra, eds. (1983) Techniques in Molecular Biology (MacMillan Publishing Company, New York); Kunkel (1985) Proc. Natl. Acad. Sci. USA 82: 488-492; Kunkel et al. (1987) Methods Enzymol. 154: 367-382; Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), herein incorporated by reference.

Conservative substitutions, such as exchanging one amino acid with another having similar properties, may be preferred. Examples of conservative substitutions include, but are not limited to, Gly to Ala, Val to Ile to Leu, Asp to Glu, Lys to Arg, Asn to Gln, and Phe to Trp to Tyr. In constructing variants of the polypeptide of interest, modifications are made such that variants continue to possess the desired activity. Obviously, any mutations made in the DNA encoding the variant polypeptide must not place the sequence out of reading frame and preferably will not create complementary regions that could produce secondary mRNA structure. See EP Patent Application Publication No. 75,444.

Biologically active variants of a polypeptide of interest will generally have at least 70%, preferably at least 80%, more preferably about 90% to 95% or more, and most preferably about 98% or more amino acid sequence identity to the amino acid sequence of the reference polypeptide molecule, which serves as the basis for comparison. A biologically active variant of a native polypeptide of interest may differ from the native polypeptide by as few as 1-15 amino acids, as few as 1-10, such as 6-10, as few as 5, as few as 4,3,2, or even 1 amino acid residue.

Proteins (including protein antigens) as used in the invention may have homology and/or sequence identity with naturally occurring forms. Similarly coding sequences capable of expressing such proteins will generally have homology and/or sequence identity with naturally occurring sequences. Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence.

In general, the term "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

For purposes of optimal alignment of the two sequences, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least twenty (20) contiguous amino acid residues, and may be 30, 40, 50, 100, or more residues. Corrections for increased sequence identity associated with inclusion of gaps in the variant's amino acid sequence can be made by assigning gap penalties. Methods of sequence alignment are well known in the art for both amino acid sequences and for the nucleotide sequences encoding amino acid sequences.

Thus, the determination of percent identity between any two sequences can be accomplished using a mathematical algorithm. One preferred, non-limiting example of a mathematical algorithm utilized for the comparison of sequences is the algorithm of Myers and Miller (1988) CABIOS 4:11-17. Such an algorithm is utilized in the ALIGN program (version 2.0), which is part of the GCG sequence alignment software package. A PAM120 weight residue table, a gap length penalty of 12, and a gap penalty of 4 can be used with the ALIGN program when comparing amino acid sequences. Another preferred, nonlimiting example of a mathematical algorithm for use in comparing two sequences is the algorithm of Karlin and Altschul (1990) Proc. Natl. Acad. Sci. USA 87: 2264, modified as in Karlin and Altschul (1993) Proc. Natl.Acad. Sci. USA 90: 5873-5877. Such an algorithm is incorporated into the NBLAST and XBLAST programs of Altschul et al. (1990) J. Mol. Biol. 215: 403. BLAST nucleotide searches can be performed with the NBLAST program, score=100, wordlength=12, to obtain nucleotide sequences homologous to a nucleotide sequence encoding the polypeptide of interest. BLAST protein searches can be performed with the XBLAST program, score=50, wordlength=3, to obtain amino acid sequences homologous to the polypeptide of interest. To obtain gapped alignments for comparison purposes, Gapped BLAST can be utilized as described in Altschul et al. 1997) Nucleic Acids Res. 25: 3389. Alternatively, PSI-Blast can be used to perform an iterated search that detects distant relationships between molecules. See Altschul et al. (1997) supra When utilizing BLAST, Gapped BLAST, and PSI-Blast programs, the default parameters of the respective programs (e.g., XBLAST and NBLAST) can be used.

See http://www.ncbi.nlm.nih.gov. Also see the ALIGN program (Dayhoff(1978) in Atlas of protein Sequence and Structure 5: Suppl. 3 (National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

An approximate alignment for nucleic acid sequences is also provided by the local homology algorithm of Smith and Waterman, Advances in Applied Mathematics 2: 482-489 (1981). This algorithm can be applied to amino acid sequences by using the scoring matrix developed by Dayhoff, Atlas of Protein Sequences and Structure, M. O. Dayhoff ed., 5 suppl. 3: 353-358, National Biomedical ResearchFoundation, Washington, D.C., USA, and normalized by Gribskov, Nucl. AcidsRes. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm. gov/cgi-bin/BLAST.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) ComputerApplic. Biol. Sci. 4:11-17.

The precise chemical structure of a polypeptide depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of polypeptides as used herein.

Alternatively, homology can be determined by hybridization of polynucleotides under conditions which form stable duplexes between homologous regions, followed by digestion with single-stranded-specific nuclease (s), and size determination of the digested fragments. Two DNA, or two polypeptide sequences are "substantially homologous" to each other when the sequences exhibit at least about 80%-85%, preferably at least about 90%, and most preferably at least about 95%-98% sequence identity over a defined length of the molecules, as determined using the methods above.

As used herein, substantially homologous or homologous also refers to sequences showing complete identity to the specified DNA or polypeptide sequence. DNA sequences that are substantially homologous or homologous can be identified in a Southern hybridization experiment under, for example, stringent conditions, as defined for that particular system. For example, stringent hybridization conditions can include 50% formamide, 5× Denhardt's Solution, 5×SSC, 0.1% SDS and 100 pg/ml denatured salmon sperm DNA and the washing conditions can include 2×SSC, 0.1% SDS at 37 C followed by 1×SSC, 0.1% SDS at 68 C. Defining appropriate hybridization conditions is within the skill of the art.

Preferably the degree of identity is preferably greater than 50% (eg. 65%. 80%. 90%. or more) and include mutants and allelic variants. Sequence identity between the proteins is preferably determined by the Smith-Waterman homology search algorithm as implemented in the MPSRCH program (Oxford. Molecular). using an affine gap search with parameters gap open penalty=12 and gap extension penalty=1.

AB5 Proteins

In a preferred embodiment of the present invention, the bARE biological molecule is an immunogen.

As used herein, the term "immunogen" refers to any compound capable of eliciting a cellular and/or humoral immune response when in contact with a cell, and includes, without limitation, immunogenic compositions such as vaccines and compositions comprising immunogens. Preferably, an antibody response and a T cell response are elicited. Such immunogens would be expected to be useful in prophylactic and therapeutic applications as well as for research applications including the generation of antibodies.

It is well known in the art that cholera toxin (CT) and the related *E. Coli* heat labile enterotoxins (LT), which are secretion products of their respective enterotoxic bacterial strains, are potent immunogens and exhibit strong toxicity when administered systemically, orally, or mucosally. In addition, it is well known that CT and LT can provide adjuvant effects for antigen when administered via the intramuscular or oral routes. The two toxins are extremely similar molecules, and are at least about 70-80% homologous at the amino acid level. The relative importance of the A and B subunits for adjuvanticity is controversial. There is speculation in the field that the toxic activity of the A subunit can modulate the adjuvant effects associated with the B subunit. Some studies demonstrate that mutations in the A subunit abrogate adjuvant activity while others show that A subunit mutations that block ADP-ribosylase activity have no effect on adjuvanticity. Other reports show varying levels of adjuvant effects for purified B subunits or recombinant B subunit preparations. It is likely that the A and B subunits have separate functions that independently contribute to adjuvanticity. These functions are ADP-ribosylase activity and receptor triggering activity, respectively.

In a preferred embodiment, the bARE protein is an AB5 protein.

In one preferred embodiment, the bARE composition comprises a modified AB5 protein as the therapeutically active agent.

Preferably the modified AB5 protein has a modified enterotoxin subunit coding region.

Preferably the modified AB5 protein has a modified enterotoxin A subunit coding region.

Preferably the modified A subunit is modified such that the A subunit coding region is modified to disrupt or inactivate the ADP-ribosyl transferase activity in the expressed product (see, for example, WO 03/004055).

As is well known, the toxicity of the cholera toxin (CT) and LT toxin resides in the A subunit. Preferably the modification of the A subunit is a site-directed mutagenesis of key active site residues which removes the toxic enzymatic activity whilst retaining immunogenicity. In a further preferred embodiment, the bARE protein is a mutant AB5 protein.

A number of mutants of CT and its homologue, LT, comprising point mutations in the A subunit are known in the art. By way of example WO 92/19265 disclose mutations in the CTA subunit at Arg-7, Asp-9, Arg-11, His-44, His-70 and Glu-112. WO 93/13202 relates to immunogenic detoxified CT and LT proteins having substitutions at one or more of amino acids Val-53, Ser-63, Val-97, Tyr-104 or Pro-106. WO 95/17211 discloses an LT mutant with a Lys-7 mutation (LT-K7). WO 96/06627 discloses an LT mutant where arginine at position 192 is substituted with glycine (mLT R192G). The mutations may be combined. For example, the CT or LT mutation may have two or more mutations.

In a particularly preferred embodiment, the AB5 protein is a detoxified mutant A subunit of *E coli* heat labile toxin (LT) selected from one or more of the group consisting of an LT with a serine (S) to lysine (K) substitution at position 63 in the A subunit (LTK63) and an alanine (A) to arginine® substitution at position 72 in the A subunit (LTR72).

In an even more preferred embodiment, the biological molecule is LKT63.

Methods for the design and production of mutants of CT, LT and CT and LT homologues, such as, for example, site-directed mutagenesis of DNA encoding the wild type toxins, are known in the art. By way of example, suitable methods for preparing and using detoxified ADP-ribosylating toxins as mucosal adjuvants is described in WO 95/17211 and as parenteral adjuvants in WO 98/42375 as well as WO 93/13202, WO 92/19265, the disclosures of which is incorporated herein by reference.

The use of ADP-ribosylating toxins and detoxified derivatives thereof, particularly LT-K63 and LT-R72, as adjuvants can be found in the following references each of which is specifically incorporated by reference herein in their entirety (Beignon, et al. Infection and Immunity (2002) 70(6):3012-3019; Pizza, et al., Vaccine (2001) 19:2534-2541; Pizza, et al., Int. J. Med. Microbiol (2000) 290(4-5):455-461; Scharton-Kersten et al. Infection and Immunity (2000) 68(9): 5306-5313; Ryan et al. Infection and Immunity (1999) 67(12):6270-6280; Partidos et al. Immunol. Lett. (1999) 67(3):209-216; Peppoloni et al. Vaccines (2003) 2(2):285-293; and Pine et al J. Control Release (2002) 85(1-3):263-270). Numerical reference for amino acid substitutions is preferably based on the alignments of the A and B subunits of ADP-ribosylating toxins set forth in Domenighini et al., Mol. Microbiol (1995) 15(6):1165-1167, specifically incorporated herein by reference in its entirety.

Whilst the mucosal adjuvant activity of CT and LT is well described for numerous experimental and antigens administered by the oral, intranasal and intra-rectal routes, the possible toxicity and resulting diarrhoea associated with the A subunit activity using these routes of administration has limited their use in human vaccines. On the other hand, workers in the field have demonstrated that topical (such as epicutaneous or transcutaneous administration without perforation of the skin) application of CT etc does not appear to result in the side effects that occur with its oral, intranasal and parenteral uses. By way of example, workers in the field have shown that when ADP-ribosylating exotoxins, such as cholera toxin (CT), heat-labile enterotoxin from *E coli* (LT), *Pseudomonas* exotoxin (ETA), pertussis toxin (PT) when applied epicutaneously, were able to pass through the skin and induce an immune response. In addition, CT, LT, ETA and PT were shown to act as adjuvants to induce an immune response to antigens co-administered on the skin (see, for example, WO 98/20734, WO 99/43350, WO 00/61184 and WO 02/064162). In addition to LT, LT mutants (LTR 192G, LTR72 and LTK63) were also shown to behave as strong adjuvants for transcutaneous immunisation (Scharton-Kersten et al (2000) Infect and Immunity 68: 5306-5313.

It is known in the art that the enterotoxin B subunit can act as an immunomodulator (see for example, WO 97/02045 and U.S.20010036917), an adjuvant (see for example WO 99/58145), and as a carrier (see for example, WO 03/000899).

Immunogenic compositions (e.g., vaccines) in accordance with the present invention may be use in a method of treating a human subject to prevent or mitigate a bacterial infection by administration of the immunogenic composition to the human subject.

Adjuvants

The compositions and/or the bARE protein of the present invention may be administered in conjunction with other immunoregulatory agents. In particular, the compositions of the present invention may be administered with an adjuvant. The inclusion of an adjuvant and in particular, a genetic adjuvant may be useful in further enhancing or modulating the CMI response. An adjuvant may enhance the CMI response by enhancing the immunogenicity of a co-administered antigen in an immunized subject, as well inducing a Th1-like immune response against the co-administered antigen which is beneficial in an immunogenic composition product.

An immune response and particularly a CMI response may be refined, by the addition of adjuvants to combinations of antigens or nucleotide sequences encoding combinations of antigens which lead to particularly effective compositions for eliciting a long lived and sustained enhanced CMI response.

As used herein, the term "adjuvant" refers to any material or composition capable of specifically or non-specifically altering, enhancing, directing, redirecting, potentiating or initiating an antigen-specific immune response.

The term "adjuvant" includes but is not limited to a bacterial ADP-ribosylating exotoxin, a biologically active factor, immunomodulatory molecule, biological response modifier or immunostimulatory molecule such as a cytokine, an interleukin, a chemokine or a ligand or an epitope (such as a helper T cell epitope) and optimally combinations thereof which, when administered with an antigen, antigen composition or nucleotide sequence encoding such antigens enhances or potentiates or modulates the CMI response relative to the CMI response generated upon administration of the antigen or combination of antigens alone. The adjuvant may be any adjuvant known in the art which is appropriate for human or animal use.

Immunomodulatory molecules such as cytokines (TNF-alpha, IL-6, GM-CSF, and IL-2), and co-stimulatory and accessory molecules (B7-1, B7-2) may be used as adjuvants in a variety of combinations. In one embodiment GM-CSF is not administered to subject before, in or after the administration regimen. Simultaneous production of an immunomodulatory molecule and an antigen of interest at the site of expression of the antigen of interest may enhance the generation of specific effectors which may help to enhance the CMI response. The degree of enhancement of the CMI response may be dependent upon the specific immunostimulatory molecules and/or adjuvants used because different immunostimulatory molecules may elicit different mechanisms for enhancing and/or modulating the CMI response. By way of example, the different effector mechanisms/immunomodulatory molecules include but are not limited to augmentation of help signal (IL-2), recruitment of professional APC (GM-CSF), increase in T cell frequency (IL-2), effect on antigen processing pathway and MHC expression (IFN-gamma and TNF-alpha) and diversion of immune response away from the Th1 response and towards a Th2 response (LTB) (see WO 97/02045). Umethylated CpG containing oligonucleotides (see WO96/02555) are also preferential inducers of a Th1 response and are suitable for use in the present invention.

Without being bound by theory, the inclusion of an adjuvant is advantageous because the adjuvant may help to enhance the CMI response to the expressed antigen by diverting the Th2 response to a Th1 response and/or specific effector associated mechanisms to an expressed epitope with the consequent generation and maintenance of an enhanced CMI response (see, for example, the teachings in WO 97/02045).

The inclusion of an adjuvant with an antigen or nucleotide sequence encoding the antigen is also advantageous because it may result in a lower dose or fewer doses of the antigen/antigenic combination being necessary to achieve the desired CMI response in the subject to which the antigen or nucleotide sequence encoding the antigen is administered, or it may result in a qualitatively and/or quantitatively different immune response in the subject. The effectiveness of an adjuvant can be determined by administering the adjuvant with the antigen in parallel with the antigen alone to animals and comparing antibody and/or cellular-mediated immunity in the two groups using standard assays such as radioimmunoassay, ELISAs, CD8+ T-cell assays, and the like, all well known in the art. Typically, the adjuvant is a separate moiety from the antigen, although a single molecule (such for example, CTB or an analogue thereof, such as LTB) can have both adjuvant and antigen properties.

As used herein, the term "genetic adjuvant" refers to an adjuvant encoded by a nucleotide sequence and which, when administered with the antigen enhances the CMI response relative to the CMI response generated upon administration of the antigen alone.

Bacterial ADP-ribosylating toxins and detoxified derivatives thereof may be used as adjuvants in the invention. Preferably, the protein is derived from E. Coli (i.e., E. Coli heat labile enterotoxin "LT), cholera ("CT"), or pertussis ("PT").

In one preferred embodiment, the genetic adjuvant is a bacterial ADP-ribosylating exotoxin.

As explained above, ADP-ribosylating bacterial toxins are a family of related bacterial exotoxins and include diphtheria toxin (DT), pertussis toxin (PT), cholera toxin (CT), the E. Coli heat-labile toxins (LT1 and LT2), Pseudomonas endotoxin A, Pseudomonas exotoxin S, B. cereus exoenzyme, B. sphaericus toxin, C. botulinum C2 and C3 toxins, C. limosum exoenzyme, as well as toxins from C. perfringens, C. spiriforma and C. difficile, Staphylococcus aureus EDIN, and ADP-ribosylating bacterial toxin mutants such as $CRM_{197}$, a non-toxic diphtheria toxin mutant (see, e.g., Bixler et al. (1989) Adv. Exp. Med. Biol. 251:175; and Constantino et al. (1992) Vaccine). Most ADP-ribosylating bacterial toxins are organized as an A:B multimer, wherein the A subunit contains the ADP-ribosyltransferase activity, and the B subunit acts as the binding moiety. Preferred ADP-ribosylating bacterial toxins for use in the compositions of the present invention include cholera toxin and the E. Coli heat-labile toxins.

Cholera toxin (CT) and the related E. Coli heat labile enterotoxins (LT) are secretion products of their respective enterotoxic bacterial strains that are potent immunogens and exhibit strong toxicity when administered systemically, orally, or mucosally. Both CT and LT are known to provide adjuvant effects for antigen when administered via the intramuscular or oral routes. These adjuvant effects have been observed at doses below that required for toxicity. The two toxins are extremely similar molecules, and are at least about 70-80% homologous at the amino acid level.

Preferably the genetic adjuvant is cholera toxin (CT), enterotoxigenic E. Coli heat-labile toxin (LT), or a derivative, subunit, or fragment of CT or LT which retains adjuvanticity. In an even more preferred embodiment, the genetic adjuvant is LT. In another preferred embodiment, the genetic adjuvant may be CTB or LTB.

Preferably the entertoxin is a non-toxic enterotoxin.

The use of detoxified ADP-ribosylating toxins as mucosal adjuvants is described in WO 95/17211 and as parenteral adjuvants in WO 98/42375. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LTR192G. The use of ADP-ribosylating toxins and detoxified derivaties thereof, particularly LT-K63 and LT-R72, as adjuvants can be found in the following references each of which is specifically incorporated by reference herein in their entirety (Beignon, et al. Infection and Immunity (2002) 70(6):3012-3019; Pizza, et al., Vaccine (2001) 19:2534-2541; Pizza, et al., Int. J. Med. Microbiol (2000) 290(4-5):455-461; Scharton-Kersten et al. Infection and Immunity (2000) 68(9): 5306-5313; Ryan et al. Infection and Immunity (1999) 67(12):6270-6280; Partidos et al. Immunol. Lett. (1999) 67(3):209-216; Peppoloni et al. Vaccines (2003) 2(2):285-293; and Pine et al J. Control Release (2002) 85(1-3):263-270). Numerical reference for amino acid substitutions is preferably based on the alignments of the A and B subunits of ADP-ribosylating toxins set forth in Domenighini et al., Mol. Microbiol (1995) 15(6): 1165-1167, specifically incorporated herein by reference in its entirety.

By way of further example, at least one of the entertoxin subunit coding regions may be genetically modified to detoxify the subunit peptide encoded thereby, for example wherein the truncated A subunit coding region has been genetically modified to disrupt or inactivate ADP-ribosyl transferase activity in the subunit peptide expression product (see, for example, WO 03/004055).

Thus, these results demonstrate that this genetic adjuvant is particularly desirable where an even more enhanced CMI response is desired. Other desirable genetic adjuvants include but are not limited to nucleotide sequences encoding IL-10, IL-12, IL-13, the interferons (IFNs) (for example, IFN-alpha, IFN-ss, and IFN-gamma), and preferred combinations thereof. Still other such biologically active factors that enhance the CMI response may be readily selected by one of skill in the art, and a suitable plasmid vector containing same constructed by known techniques.

Thus, compositions (e.g., vaccines) of the invention may be administered in conjunction with other immunoregulatory agents. In particular, compositions will usually include an adjuvant. Adjuvants for use with the invention include, but are not limited to, one or more of the following set forth below:

A. Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of *Vaccine Design* . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds talking any suitable form (e.g. gel, crystalline, amorphous, etc.), and with adsorption to the salt(s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose.

B. Oil-Emulsions

Oil-emulsion compositions suitable for use as adjuvants in the invention include squalene-water emulsions, such as MF59 (5% Squalene, 0.5% Tween 80, and 0.5% Span 85, formulated into submicron particles using a microfluidizer). See WO90/14837. See also, Podda, "The adjuvanted influenza vaccines with novel adjuvants: experience with the MF59-adjuvanted vaccine", Vaccine (2001) 19: 2673-2680; Frey et al., "Comparison of the safety, tolerability, and immunogenicity of a MF59-adjuvanted influenza vaccine and a non-adjuvanted influenza vaccine in non-elderly adults", Vaccine (2003) 21:4234-4237. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyethylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE), for example, the submicron oil-in-water emulsion known as "MF59" (International Publication No. WO90/14837; U.S. Pat. Nos. 6,299,884 and 6,451,325, incorporated herein by reference in their entireties; and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 µg/dose, more preferably 0-250 µg/dose and most preferably, 0-100 µg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 µg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325, incorporated herein by reference in their entireties.

Complete Freund's adjuvant (CFA) and incomplete Freund's adjuvant (IFA) may also be used as adjuvants in the invention.

C. Saponin Formulations

Saponin formulations, may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-LC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexs (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of additional detergent. See WO00/07621.

A review of the development of saponin based adjuvants can be found at Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.

D. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., "Chimeric Recombinant Hepatitis E Virus-Like Particles as an Oral Vaccine Vehicle Presenting Foreign Epitopes", Virology (2002) 293:273-280; Lenz et al., "Papillomarivurs-Like Particles Induce Acute Activation of Dendritic Cells", Journal of Immunology (2001) 5246-5355; Pinto, et al., "Cellular Immune Responses to Human Papillomavirus (HPV)-16 L1 Healthy Volunteers Immunized with Recombinant HPV-16 L1 Virus-Like Particles", Journal of Infectious Diseases (2003) 188:327-338; and Gerber et al., "Human Papillomavrisu Virus-Like Particles Are Efficient Oral Immunogens when Coadministered with *Escherichia coli* Heat-Labile Entertoxin Mutant R192G or CpG", Journal of Virology (2001) 75(10):4752-4760. Virosomes are discussed further in, for example, Gluck et al., "New Technology Platforms in the Development of Vaccines for the Future", Vaccine (2002) 20:B10-B16. Immunopotentiating reconstituted influenza virosomes (IRIV) are used as the subunit antigen delivery system in the intranasal trivalent INFLEXAL™ product {Mischler & Metcalfe (2002) Vaccine 20 Suppl 5:B17-23} and the INFLUVAC PLUS™ product.

E. Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0.689 454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

(2) Lipid A Derivatives

Lipid A derivatives include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", Vaccine (2003) 21:2485-2491; and Pajak, et al., "The Adjuvant OM-174 induces both the migration and maturation of murine dendritic cells in vivo", Vaccine (2003) 21:836-842.

(3) Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. Nos. 6,207,646; 6,239,116 and 6,429,199.

The CpG sequence may be directed to TLR9, such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068; Krieg, "From A to Z on CpG", TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., "Secondary structures in CpG oligonucleotides affect immunostimulatory activity", BBRC (2003) 306:948-953; Kandimalla, et al., "Toll-like receptor 9: modulation of recognition and cytokine induction by novel synthetic GpG DNAs", Biochemical Society Transactions (2003) 31(part 3):664-658; Bhagat et al., "CpG penta- and hexadeoxyribonucleotides as potent immunomodulatory agents" BBRC (2003) 300:853-861 and WO03/035836.

(4) ADP-ribosylating Toxins and Detoxified Derivatives Thereof.

As described above, bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references, each of which is specifically incorporated by reference herein in their entirety: Beignon, et al., "The LTR72 Mutant of Heat-Labile Enterotoxin of *Escherichia coli* Enahnces the Ability of Peptide Antigens to Elicit CD4+ T Cells and Secrete Gamma Interferon after Coapplication onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol (2000) 290(4-5):455-461; Scharton-Kersten et al., "Transcutaneous Immunization with Bacterial ADP-Ribosylating Exotoxins, Subunits and Unrelated Adjuvants", Infection and Immunity (2000) 68(9): 5306-5313; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" Infection and Immunity (1999) 67(12): 6270-6280; Partidos et al., "Heat-labile enterotoxin of *Escherichia coli* and its site-directed mutant LTK63 enhance the proliferative and cytotoxic T-cell responses to intranasally co-immunized synthetic peptides", Immunol. Lett. (1999)

67(3):209-216; Peppoloni et al., "Mutants of the *Escherichia coli* heat-labile enterotoxin as safe and strong adjuvants for intranasal delivery of vaccines", Vaccines (2003) 2(2):285-293; and Pine et al., (2002) "Intranasal immunization with influenza vaccine and a detoxified mutant of heat labile enterotoxin from *Escherichia coli* (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol (1995) 15(6): 1165-1167, specifically incorporated herein by reference in its entirety.

F. Bioadhesives and Mucoadhesives

Bioadhesives and mucoadhesives may also be used as adjuvants in the invention. Suitable bioadhesives include esterified hyaluronic acid microspheres (Singh et al. (2001) *J. Cont. Rele.* 70:267-276) or mucoadhesives such as cross-linked derivatives of poly(acrylic acid), polyvinyl alcohol, polyvinyl pyrollidone, polysaccharides and carboxymethyl-cellulose. Chitosan and derivatives thereof may also be used as adjuvants in the invention. E.g. WO99/27960.

G. Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. Nos. 6,090,406, 5,916,588, and EP 0 626 169.

I. Polyoxyethylene Ether and Polyoxyethylene Ester Formulations

Adjuvants suitable for use in the invention include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

K. Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinolone Compounds

Examples of imidazoquinolone compounds suitable for use adjuvants in the invention include Imiquamod and its homologues, described further in Stanley, "Imiquimod and the imidazoquinolones: mechanism of action and therapeutic potential" Clin Exp Dermatol (2002) 27(7):571-577 and Jones, "Resiquimod 3M", Curr Opin Investig Drugs (2003) 4(2):214-218.

The invention may also comprise combinations of aspects of one or more of the adjuvants identified above. For example, the following adjuvant compositions may be used in the invention:

(1) a saponin and an oil-in-water emulsion (WO99/11241);
(2) a saponin (e.g., QS21)+a non-toxic LPS derivative (e.g. 3dCMPL) (see WO94/00153);
(3) a saponin (e.g., QS21)+a non-toxic LPS derivative (e.g. 3dMPL)+a cholesterol;
(4) a saponin (e.g. QS21)+3dMPL+IL-12 (optionally+a sterol) (WO98/57659);
(5) combinations of 3dMPL with, for example, QS21 and/or oil-in-water emulsions (See European patent applications 0835318, 0735898 and 0761231);
(6) SAF, containing 10% Squalane, 0.4% Tween 80, 5% pluronic-block polymer L121, and thr-MDP, either microfluidized into a submicron emulsion or vortexed to generate a larger particle size emulsion;
(7) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™);
(8) one or more mineral salts (such as an aluminum salt)+a non-toxic derivative of LPS (such as 3dPML); and/or
(9) one or more mineral salts (such as an aluminum salt)+an immunostimulatory oligonucleotide (such as a nucleotide sequence including a CpG motif).

M. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

Aluminum salts and MF59 are preferred adjuvants for use with injectable influenza vaccines. Bacterial toxins and bioadhesives are preferred adjuvants for use with mucosally-delivered vaccines, such as nasal vaccines.

Preferably the compositions of the present invention are administered with alum and/or CpG sequences.

Formulations

The compositions of the invention may be prepared in various forms. For example, the compositions may be prepared as injectables, such as liquid solutions. Solid forms suitable for solution in, or suspension in, liquid vehicles prior to injection can also be prepared (e.g. a lyophilised composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Compositions of the invention are preferably immunogenic compositions, and are more preferably vaccine compositions. The pH of the composition is preferably between 6 and 8, preferably about 7. The pH may be maintained by the use of a buffer. The composition may be sterile and/or pyrogen-free. The composition may be isotonic with respect to humans.

Preferably the bARE composition comprises one or more antigens.

An "antigen" refers to any agent, generally a macromolecule, which can elicit an immunological response in an individual. The term may be used to refer to an individual macromolecule or to a homogeneous or heterogeneous population of antigenic macromolecules. As used herein, the term "antigen" is generally used to refer to a protein molecule or portion thereof which comprises one or more epitopes. For purposes of the present invention, antigens can be obtained or derived from any known virus, bacteria, parasite or fungal pathogen. The term also intends any of the various tumor-specific antigens and antigens associated with autoimmune diseases.

Furthermore, for purposes of the present invention, an "antigen" includes a protein having modifications, such as deletions, additions and substitutions (generally conservative in nature) to the native sequence, so long as the protein maintains sufficient immunogenicity. These modifications may be deliberate, for example through site-directed mutagenesis, or may be accidental, such as through mutations of hosts which produce the antigens.

In various aspects of the invention, the antigen contains one or more T cell epitopes. A "T cell epitope" refers generally to those features of a peptide structure which are capable of inducing a T cell response. In this regard, it is accepted in the art that T cell epitopes comprise linear peptide determinants that assume extended conformations within the peptide-binding cleft of MHC molecules, (Unanue et al. (1987) Science 236: 551-557). As used herein, a T cell epitope is generally a peptide having at least about 3-5 amino acid residues, and preferably at least 5-10 or more amino acid residues. The ability of a particular antigen to stimulate a cell-mediated immunological response may be determined by a number of well-known assays, such as by lymphoproliferation (lymphocyte activation) assays, CTL cytotoxic cell assays, or by assaying for T-lymphocytes specific for the antigen in a sensitized subject. See, e.g., Erickson et al. (1993) J. Immunol. 151: 4189-4199; and Doe et al. (1994) Eur. J. Immunol. 24: 2369-2376.

In other aspects of the invention, the antigen contains one or more B cell epitopes. A "B cell epitope" generally refers to the site on an antigen to which a specific antibody molecule binds. The identification of epitopes which are able to elicit an antibody response is readily accomplished using techniques well known in the art. See, e.g., Geysen et al. (1984) Proc. Natl. Acad. Sci. USA 81 3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al. (1986) Molecular Immunology 23: 709-715 (technique for identifying peptides with high affinity for a given antibody).

The antigen of interest will preferably be associated with a pathogen, such as a viral, bacterial or parasitic pathogen, or the antigen may be a tumor-specific antigen. The antigen may be a full length protein. Alternatively, the antigen may just consist essentially of a B-cell epitope or a T-cell epitope of an antigen.

Tumor-specific antigens include, but are not limited to, any of the various MAGEs (melanoma associated antigen E), including MAGE 1, MAGE 2, MAGE 3 (HLA-A1 peptide), MAGE 4, etc.; any of the various tyrosinases (HLA-A2 peptide); mutant ras; mutant p53; and p97 melanoma antigen. Other tumor-specific antigens include the Ras peptide and p53 peptide associated with advanced cancers, the HPV 16/18 and E6/E7 antigens associated with cervical cancers, MUC1-KLH antigen associated with breast carcinoma, CEA (carcinoembryonic antigen) associated with colorectal cancer, gp100 or MART1 antigens associated with melanoma, and the PSA antigen associated with prostate cancer. The p53 gene sequence is known (see e.g., Harris et al. (1986) Mol. Cell. Biol. 6: 4650-4656) and is deposited with GenBank under Accession No. M14694.

Suitable viral antigens include, but are not limited to, polynucleotide sequences encoding antigens from the influenza family of viruses (see for example, the influenza sequence database at http://www.flu.lanl.gov/review/annual.thml), from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV). By way of example, the viral genomic sequence of HBV is known, as are methods for obtaining antigen-encoding sequences therefrom. See, e.g., Ganem et al. (1987) Annu. Rev. Biochem. 56: 651-693; Hollinger, F. B. (1990) Hepatitis B virus, vol. II, pp. 21712235, in Fields et al. (eds), Virologv, 2nd ed, Raven Press, New York, N.Y.; and Valenzuela et al. (1980) The nucleotide Sequence of the Hepatitis B viral Genome and the Identification of the Major Viral Genes, pp. 57-70, in Fields et al. (eds), Animal Virus Genetics, Academic Press, New York, N.Y.). The HBV genome encodes several viral proteins, including the large, middle and major surface antigen polypeptides, the X-gene polypeptide, and the core polypeptide. See, e.g., Yokosuka et al. (1986) N. Engl. J. Med. 315: 1187-1192; Imazeki et al. (1987) Hepatology 7: 753-757; Kaneko et al. (1988) J. Virol. 62: 3979-3984; and Ou et al. (1990) J. Virol. 64: 4578-4581. In like manner, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 and E2. See, eg., Houghton et al. (1991) Hepatology 14: 381-388. The sequences encoding these HBV and HCV proteins, as well as antigenic fragments thereof, will find use in the present methods. Similarly, the coding sequence for the 8-antigen from HDV is known (see, e.g., U.S. Pat. No. 5,378,814).

In like manner, sequences encoding a wide variety of protein antigens from the herpesvirus family can be used in the present invention, including antigens derived from herpes simplex virus (HSV) types 1 and 2, such as HSV-1 and HSV-2 glycoproteins gB, gD and gH; antigens from varicella zoster virus (VZV), Epstein Barr virus (EBV) and cytomegalovirus (CMV) including CMV gB and gH; and antigens from other human herpesviruses such as HHV6 and HHV7. (See, e.g. Chee et al. (1990) Cytomegaloviruses (J. K. McDougall, ed., Springer-Verlag, pp. 125169; McGeoch et al. (1988) J. Gen. Virol. 69: 1531-1574; U.S. Pat. No. 5,171,568; Baer et al. (1984) Nature 310: 207-211; and Davison et al. (1986) J. Gen. Virol. 67:1759-1816.)HIV antigens, such as the gp120 sequences for a multitude of HIV-1 and HIV-2 isolates, including members of the various genetic subtypes of HIV, are known and reported (see, e.g., Myers et al., Los Alamos Database, Los Alamos National Laboratory, Los Alamos, N. Mex. (1992); and Modrow et al. (1987) J. Virol. 61: 570-578) and antigens derived from any of these isolates will find use in the present methods.

Furthermore, the invention is equally applicable to other immunogenic moieties derived from any of the various HIV isolates, including any of the various envelope pro Reoviridae; Birnaviridae; Rhabodoviridae (e.g., rabies virus, etc.); Filoviridae; Paramyxoviridae (e.g., mumps virus, measles virus, respiratory syncytial virus, etc.); Bunyaviridae; Arenaviridae; Retroviradae (e.g., HTLV-I; HTLV-11; HIV-1 (also known as HTLV-III, LAV, ARV, hTLR, etc.)), including but not limited to antigens from the isolates HIV, HIV, HIVv, HIV, HIV-); HIV-1, HIV-1, HIV-2, among others. See, e.g. g. Virology, 3rd Edition (W. K. Joklik ed. 1988); Fundamental Virology, 2nd Edition (B. N. Fields and D. M. Knipe, eds. 1991), for a description of these and other viruses.

Sequences encoding suitable bacterial and parasitic antigens are obtained or derived from known causative agents responsible for diseases such as Diptheria, Pertussis, Tetanus, Tuberculosis, Bacterial or Fungal Pneumonia, Cholera, Typhoid, Plague, Shigellosis or Salmonellosis, Legionaire's Disease, Lyme Disease, Leprosy, Malaria, Hookworm, Onchocerciasis, Schistosomiasis, Trypamasomialsis, Lesmaniasis, *Giardia*, Amoebiasis, Filariasis, *Borelia*, and Trichinosis. Still further antigens can be obtained or derived from unconventional viruses or virus-like agents such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

Both the sequence for the minimal promoter and the coding sequence of interest can be obtained and/or prepared using known methods. For example, substantially pure antigen preparations can be obtained using standard molecular biological tools. That is, polynucleotide sequences coding for the above-described antigens can be obtained using recombinant methods, such as by screening cDNA and genomic libraries from cells expressing the gene, or by deriving the gene from a vector known to include the same. Furthermore, the desired gene or promoter sequence can be isolated directly from cells and tissues containing the same, using standard techniques, such as phenol extraction and PCR of cDNA or genomic DNA. See, e.g., Sambrook et al., supra, for a description of techniques used to obtain and isolate DNA. Polynucleotide sequences can also be produced synthetically, rather than cloned.

Yet another convenient method for isolating specific nucleic acid molecules is by the polymerase chain reaction (PCR). Mullis et al. (1987) Methods Enzymol. 155: 335-350. This technique uses DNA polymerase, usually a thermostable DNA polymerase, to replicate a desired region of DNA. The region of DNA to be replicated is identified by oligonucleotides of specified sequence complementary to opposite ends and opposite strands of the desired DNA to prime the replication reaction. The product of the first round of replication is itself a template for subsequent replication, thus repeated successive cycles of replication result in geometric amplification of the DNA fragment delimited by the primer pair used.

Antigens in the composition will typically be present at a concentration of at least 1 μg/ml each. In general, the concentration of any given antigen will be sufficient to elicit an immune response against that antigen. As an alternative to using protein antigens in the composition of the invention, nucleic acid encoding the antigen may be used Robinson & Torres (1997) *Seminars in Immunology* 9:271-283; Donnelly et al. (1997) *Annu Rev Immunol* 15:617-648; Scott-Taylor & Dalgleish (2000) *Expert Opin Investig Drugs* 9:471-480; Apostolopoulos & Plebanski (2000) *Curr Opin Mol Ther* 2:441-447; Ilan (1999) *Curr Opin Mol Ther* 1:116-120; Dubensky et al. (2000) *Mol Med* 6:723-732; Robinson & Pertmer (2000) *Adv Virus Res* 55:1-74; Donnelly et al. (2000) *Am J Respir Crit Care Med* 162(4 Pt 2):S190-193 and Davis (1999) *Mt. Sinai J. Med.* 66:84-90. Protein components of the compositions of the invention may thus be replaced by nucleic acid (preferably DNA e.g. in the form of a plasmid) that encodes the protein.

Compositions of the present invention are preferably prepared by premixing the stabilizing and buffering agents, and any other excipients prior to incorporation of the polypeptide of interest. Any additional excipients that may be added to further stabilize the compositions of the present invention must not adversely affect the stabilizing effects of the primary stabilizing agent, i.e., an amino acid base, in combination with the buffering agent, i.e., an acid substantially free of its salt form, the salt form of the acid, or a mixture of the acid and its salt form, as used to obtain the novel compositions disclosed herein. Following addition of a preferred amount of an amino acid base to achieve decreased aggregate formation of a polypeptide of interest, pH of the liquid composition is adjusted using the buffering agent, preferably within a range disclosed herein, more preferably to the pH optimum for the polypeptide of interest. Although pH can be adjusted following addition of the polypeptide of interest into the composition, preferably it is adjusted prior to addition of this polypeptide, as this can reduce the risk of denaturation the polypeptide.

Appropriate mechanical devices are then used for achieving a proper mix of constituents.

The bARE compositions of the present invention encompass liquid compositions and dried forms thereof. For purposes of the present invention, the term "liquid" with regard to pharmaceutical compositions or formulations is intended to include the term "aqueous", and includes liquid formulations that are frozen. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11: 12-20), or air drying (Carpenter and Crowe (1988) Cryobiology 25:459-470; and Roser (1991) Biopharm. 4:47-53).

By "aqueous" is intended a composition prepared with, containing, or dissolved in water, including mixtures wherein water is the predominating substance in the mixture. A predominating substance is present in a greater quantity than another component of the mixture. By "nonaqueous" is intended a composition prepared with, containing, or dissolved in a substance other than water or mixtures wherein water is not the predominating substance in the mixture. By "solution" is intended a homogeneous preparation of two or more substances, which may be solids, liquids, gases, or intercombinations thereof.

The term "lyophilize" with regard to bARE protein formulations is intended to refer to rapid freeze drying under reduced pressure of a plurality of vials, each containing a unit dose of the bARE protein formulation of the present invention therein. Lyophilizers, which perform the above-described lyophilization, are commercially available and readily operable by those skilled in the art. In one embodiment of the present invention, the liquid composition is prepared as a lyophilized composition.

The bARE protein compositions of the present invention are "stabilized" compositions. By "stabilized" is intended the compositions retain the bARE polypeptide in its substantially multimeric state during storage, and hence the therapeutic effectiveness of this bARE polypeptide is not compromised due to aggregate formation or dissociation into subunit forms. By "during storage" is intended a composition or formulation once prepared, is not immediately administered to a subject. Rather, following preparation, it is packaged for storage, either in a liquid form, in a frozen state, or in a dried form for later reconstitution into a liquid form or other form suitable for administration to a subject. Preferably, compositions of the invention are stored directly in their liquid form to take full advantage of the convenience of having storage stability in the liquid form, ease of administration without reconstitution, and ability to supply the formulation in prefilled, ready-to-use syringes or as multidose preparations if the formulation is compatible with bacteriostatic agents. The stabilized bARE compositions of the invention preferably have a shelf-life of at least about 6 months, 12 months, 18 months, more preferably at least 20 months, still more preferably at least about 22 months, most preferably at least about 24 months when stored at 2-8° C.

The stabilized composition comprising the bARE protein may be formulated in a unit dosage and may be in an injectable or infusible form such as a solution. Furthermore, it can be stored frozen or prepared in the dried form, such as a lyophilized powder, which can be reconstituted into the liquid solution before administration by any of various methods including oral or parenteral routes of administration.

Preferably it is stored in the liquid formulation to take advantage of the increased storage stability achieved in accordance with the methods of the present invention as outlined below. The stabilized composition is preferably sterilized by membrane filtration and is stored in unit-dose or multi-dose containers such as sealed vials or ampules. Additional methods for formulating a composition generally known in the art may be used to further enhance storage stability of the liquid compositions disclosed herein provided they do not adversely affect the beneficial effects of the preferred stabilizing and buffering agents disclosed in the methods of the invention. A thorough discussion of formulation and selection of pharmaceutically acceptable carriers, stabilizers, etc. can be found in Remington's Pharmaceutical Sciences (1990) (18'ed. Mack Pub. Co., Eaton, Pa.), herein incorporated by reference.

The composition of the invention will typically, in addition to the components mentioned above, comprise one or more 'pharmaceutically or immunologically acceptable carriers', which includes, for example, any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. The compositions may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in Gennaro (2000) *Remington: The Science and Practice of Pharmacy.* 20th ed., ISBN: 0683306472.

The bARE proteins of the present invention be formulated into a pharmaceutical composition or an immunotherapeutic composition or a vaccine composition. Such formulations comprise biological molecules, such as a bARE protein combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (for eg, a powder or granules) form for reconstitution with a suitable vehicle (e.g., sterile pyrogen-free water) prior to parenteral administration of the reconstituted composition. The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Administration

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral (e.g. tablet, spray), vaginal, topical, transdermal {e.g. see WO99/27961) or transcutaneous {e.g. WO02/074244 and WO02/064162 intranasal {e.g. see WO03/028760) ocular, aural, pulmonary or other mucosal administration. The invention may be used to elicit systemic and/or mucosal immunity.

The compositions of the present invention may be administered, either alone or as part of a composition, via a variety of different routes. Certain routes may be favoured for certain compositions, as resulting in the generation of a more effective immune response, prefereably a cell mediated immune (CMI) response, or as being less likely to induce side effects, or as being easier for administration.

By way of example, the compositions of the present invention may be administered via a systemic route or a mucosal route or a transdermal route or it may be administered directly into a specific tissue. As used herein, the term "systemic administration" includes but is not limited to any parenteral routes of administration. In particular, parenteral administration includes but is not limited to subcutaneous, intraperitoneal, intravenous, intraarterial, intramuscular, or intrasternal injection, intravenous, intraarterial, or kidney dialytic infusion techniques. Preferably, the systemic, parenteral administration is intramuscular injection.

In one preferred embodiment of the method, the compositions of the present invention are administered via a transdermal route. In this regard, and without being bound by theory, it is believed that transdermal administration of a composition may be preferred because it more efficiently activates the cell mediated immune (CMI) arm of the immune system.

The term "transdermal" delivery intends intradermal (e.g., into the dermis or epidermis), transdermal (e.g., "percutaneous") and transmucosal administration, i.e., delivery by passage of an agent into or through skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc.,(1987); and *Transdermal Delivery of Drugs*, Vols. 1-3, Kydonieus and Berner (eds.), CRC Press, (1987). Thus, the term encompasses delivery of an agent using a particle delivery device (e.g., a needleless syringe) such as those described in U.S. Pat. No. 5,630,796, as well as delivery using particle-mediated delivery devices such as those described in U.S. Pat. No. 5,865,796.

As used herein, the term "mucosal administration" includes but is not limited to oral, intranasal, intravaginal, intrarectal, intratracheal, intestinal and ophthalmic administration.

Mucosal routes, particularly intranasal, intratracheal, and ophthalmic are preferred for protection against natural exposure to environmental pathogens such as RSV, flu virus and cold viruses or to allergens such as grass and ragweed pollens and house dust mites.

The enhancement of the immune response, preferably the CMI response will enhance the protective effect against a subsequently encountered target antigen such as an allergen or microbial agent.

In another preferred embodiment of the present invention, the compositions of the present invention may be administered to cells which have been isolated from the host subject. In this preferred embodiment, preferably the composition is administered to professional antigen presenting cells (APCs), such as dendritic cells. APCs may be derived from a host subject and modified ex vivo to express an antigen of interest and then transferred back into the host subject to induce an enhanced CMI response. Dendritic cells are believed to be the most potent APCs for stimulating enhanced CMI responses because the expressed epitopes of the antigen of interest must be acquired, processed and presented by professional APCs to T cells (both Th1 and Th2 helper cells as well as CD8+ T-cells) in order to induce an enhanced CMI response.

Particle Administration

Particle-mediated methods for delivering the compositions of the present invention are known in the art. Thus, once prepared and suitably purified, the above-described antigens or NOI encoding same can be coated onto core carrier particles using a variety of techniques known in the art. Carrier particles are selected from materials which have a suitable density in the range of particle sizes typically used for intracellular delivery from a gene gun device. The optimum carrier particle size will, of course, depend on the diameter of the target cells.

By "core carrier"" is meant a carrier on which a guest antigen or guest nucleic acid (e.g., DNA, RNA) is coated in order to impart a defined particle size as well as a sufficiently high density to achieve the momentum required for cell membrane penetration, such that the guest molecule can be delivered using particle-mediated techniques (see, e.g., U.S. Pat. No. 5,100,792). Core carriers typically include materials such as tungsten, gold, platinum, ferrite, polystyrene and latex. See e.g., *Particle Bombardment Technology for Gene Transfer*, (1994) Yang, N. ed., Oxford University Press, New York, N.Y. pages 10-11. Tungsten and gold particles are preferred. Tungsten particles are readily available in average sizes of 0.5 to 2.0 microns in diameter. Gold particles or microcrystalline gold (e.g., gold powder A1570, available from Engelhard Corp., East Newark, N.J.) will also find use with the present invention. Gold particles provide uniformity in size (available from Alpha Chemicals in particle sizes of 1-3 microns, or available from Degussa, South Plainfield, N.J. in a range of particle sizes including 0.95 microns). Microcrystalline gold provides a diverse particle size distribution, typically in the range of 0.5-5 microns. However, the irregular surface area of microcrystalline gold provides for highly efficient coating with nucleic acids. A number of methods are known and have been described for coating or precipitating NOIs onto gold or tungsten particles. Most such methods generally combine a predetermined amount of gold or tungsten with plasmid DNA, CaCl2 and spermidine. The resulting solution is vortexed continually during the coating procedure to ensure uniformity of the reaction mixture. After precipitation of the NOI, the coated particles can be transferred to suitable membranes and allowed to dry prior to use, coated onto surfaces of a sample module or cassette, or loaded into a delivery cassette for use in particular gene gun instruments.

The particle compositions or coated particles are administered to the individual in a manner compatible with the dosage formulation, and in an amount that will be effective for the purposes of the invention. The amount of the composition to be delivered (e.g., about 0.1 mg to 1 mg, more preferably 1 to 50 ug of the antigen or allergen, depends on the individual to be tested. The exact amount necessary will vary depending on the age and general condition of the individual to be treated, and an appropriate effective amount can be readily determined by one of skill in the art upon reading the instant specification.

Host Mammalian Subject

As used herein, the term "host mammalian subject" means any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species, since the immune systems of all of these vertebrates operate similarly. If a mammal, the subject will preferably be a human, but may also be a domestic livestock, laboratory subject or pet animal.

The mammal is preferably a human. Where the immunogenic composition (e.g., vaccine) is for prophylactic use, the human is preferably a child (e.g. a toddler or infant) or a teenager; where the vaccine is for therapeutic use, the human is preferably a teenager or an adult. An immunogenic composition (e.g., vaccine) intended for children may also be administered to adults e.g. to assess safety, dosage, immunogenicity, etc.

Prevent and/or Treat

The invention also provides the compositions of the invention for use as medicaments (eg. as immunogenic compositions such as vaccines) or as diagnostic reagents. It also provides the use of the compositions in the manufacture of: (i) a medicament for treating or preventing an immunological disorder. The invention also provides a method of treating a patient, comprising administering to the patient a therapeutically effective amount of a composition according to the invention.

The invention also provides the use of the compositions of the invention in the manufacture of a medicament for raising or modulating or enhancing an immune response in a mammal. The medicament is preferably an immunogenic composition such as a vaccine and to the preparation of such compositions to prevent and/or treat an immunological disorder. It is to be appreciated that all references herein to treatment include curative, palliative and prophylactic treatment.

As used herein, the term "immune response" refers to the development in a host mammalian subject of a humoral and/or a cellular immune response against an antigen. As used herein, the term "humoral immune response" refers to an immune response mediated by antibody molecules. The antibodies generated by humoral immunity are primarily effective against extracellular infectious agents.

As used herein, the term "cell mediated immune (CMI) response" is one mediated by T-lymphocytes and/or other white blood cells. The CMI immune mechanisms are generally more effective against intracellular infections and disease because the CMI mechanisms prime T cells in a way that, when an antigen appears at a later date, memory T cells are activated to result in a CM response that destroys target cells that have the corresponding antigen or a portion thereof on their cell surfaces, and thereby the infecting pathogen. The CMI response is focused on the destruction of the source of infection mediated by either effector cells that destroy infected cells of the host by direct cell-to-cell contact and/or by the release of molecules, such as cytokines, that possess anti-viral activity. Thus the CMI response, which is characterised by a specific T lymphocyte cellular response, is crucial to produce resistance to diseases caused by cancer, viruses, pathogenic and other intracellular microorganisms.

The administration of bARE composition of the present invention may be for either "prophylactic" or "therapeutic" purpose. As used herein, the term "therapeutic" or "treatment" includes any of following: the prevention of infection or reinfection; the reduction or mitigation or elimination of symptoms; and the reduction or complete elimination of a pathogen. Treatment may be effected prophylactically (prior to infection) or therapeutically (following infection).

Prophylaxis or therapy includes but is not limited to eliciting an effective immune response, preferably a CMI immune response and/or alleviating, reducing, curing or at least partially arresting symptoms and/or complications resulting from a T cell mediated immune disorder. When provided prophylactically, the bARE composition of the present invention is typically provided in advance of any symptom. The prophylactic administration of the bARE composition of the present invention is to prevent or ameliorate any subsequent infection or disease. When provided therapeutically, the composition of the present invention is typically provided at (or shortly after) the onset of a symptom of infection or disease to attenuate, for example, an actual symptom. Thus the composition of the present invention may be provided either prior to the anticipated exposure to a disease causing agent or disease state or after the initiation of an infection or disease.

Whether prophylactic or therapeutic administration (either alone or as part of a composition) is the more appropriate will usually depend upon the nature of the disease. By way of example, the composition of the present invention could be used in immunotherapy protocols to actively inducing immunity by vaccination. This latter form of treatment is advantageous because the immunity is prolonged. On the other hand a composition will preferably, though not necessarily be used prophylactically to induce an effective CMI response, against subsequently encountered antigens or portions thereof (such as epitopes) related to the target antigen.

The bARE composition dose administrated to a host subject, in the context of the present invention, is usually in an amount sufficient to effect a beneficial prophylactic or therapeutic immune response, preferably a CMI response, in the subject over time.

The invention also provides a method for raising an immune response in a mammal comprising the step of administering an effective amount of a composition of the invention. The immune response is preferably protective and preferably involves antibodies and/or cell-mediated immunity. The method may raise a booster response.

As used herein, the term ""prophylactically or therapeutically effective dose" means a dose in an amount sufficient to elicit an enhanced immune response, preferably a CMI response to one or more antigens or epitopes, when administered, for example, as part of a bARE composition and/or to alleviate, reduce, cure or at least partially arrest symptoms and/or complications from a T cell mediated immune disorder.

Immunogenic compositions as described herein comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The compositions of the present invention can be evaluated in in vitro and in vivo animal models prior to host, e.g., human, administration.

Dosage

Prophylaxis or therapy can be accomplished by a single direct administration at a single time point or multiple time points. Administration can also be delivered to a single or to multiple sites. Some routes of administration, such as mucosal administration via ophthalmic drops may require a higher dose. Those skilled in the art can adjust the dosage and concentration to suit the particular route of delivery.

In one embodiment, dosage treatment can be a single dose schedule or a multiple dose schedule. Multiple doses may be used in a primary immunisation schedule and/or in a booster immunisation schedule. In a multiple dose schedule, the various doses may be given by the same or different routes such as, but not limited to a parenteral prime and mucosal boost or a mucosal prime and parenteral boost.

Mutant AB5 Molecules

The stabilized bARE proteins and stabilised $AB_5$ proteins in accordance with the present invention may be used for preventing or treatment of infections and/or disorders in humans. Mutant $AB_5$ bacterial toxins, such as LTK63 may also be used for preventing or treatment of infections and/or disorders in humans. In particular, stabilized LTK63 is useful as a non-toxic mucosal adjuvant in admixture with a second antigen. The preparation of LTK63 mutants and the formulation of these mutants into vaccines as mucosal adjuvants is described in detail in Applicant's prior publications and patent applications, including Tierney et al., J Infect Dis 188 (2003) 753-8; and Baudner et al., Vaccine 21 (2003) 3837-3844; and International Patent Application Nos. WO 93/13202 and WO 97/02348 of Biocine SpA (now Chiron SpA), the disclosures are incorporated by reference herein in their entirety and for all purposes.

Given the disclosure provided in the present application and the prior referenced applications, the method of preparation of vaccine formulations incorporating appropriate stabilized $AB_5$ proteins in accordance with the present invention, in particular genetically detoxified $AB_5$ bacterial toxins, such as LTK63, will be readily apparent to one of skill in the art.

Thus, in certain aspects, the invention provides immunogenic compositions comprising a stabilized $AB_5$ class protein, in particular where the $AB_5$ class protein is a genetically detoxified immunogenic bacterial toxin, such as LTK63. In certain embodiments, the immunogenic composition is a human vaccine. The stabilized $AB_5$ class protein may be the antigenic agent of the composition, or an adjuvant for another antigenic agent of the composition. In one specific embodiment, the stabilized $AB_5$ class protein is a mucosal adjuvant.

Disease States

The compositions of the present invention may be used to prevent and/or treat disorders such as but not limited to: pneumonia, cardiovascular diseases, atherosclerosis, bronchitis, pharyngitis, laryngitis, sinusitis, obstructive lung diseases, asthma, chronic obstructive pulmonary disease, reactive arhritis, otitis media, abdominal aortic aneurysm, erythema nodosum, Reiter syndrome, sarcoidosis, Alzheimer's disease, multiple sclerosis, lymphogranuloma venereum, ocular trachoma, pelvic inflammatory disease, inclusion conjunctivitis, genital trachoma, infant pneumonitis, incipient trachoma, keratitis, papillary hypertrophy, corneal infiltration, vulvovaginitis, mucopurulent rhinitis, salpingitis, cervicitis, cervical follicles, prostatitis, proctitis, urethritis, lymphogranule inguinale, climatic bubo, tropical bubo, and/oresthiomene.

Kits

Also included in the invention is a kit comprising the bARE composition of the present invention. The kit may also include an adjuvant, preferably a genetic adjuvant is administered with or as part of the bARE composition and instructions for administering the biological molecule. Other preferred components of the kit include an applicator for administering the bARE composition. As used herein, the term "applicator" refers to any device including but not limited to a hypodermic syringe, gene gun, particle acceleration device, nebulizer, dropper, bronchoscope, suppository, impregnated or coated vaginally-insertable material such as a tampon, douche preparation, solution for vaginal irrigation, retention enema preparation, suppository, or solution for rectal or colonic irrigation for applying the bARE composition either systemically or mucosally or transdermally to the host subject.

The kit may further include a second component comprising one or more of the following: instructions, syringe or other delivery device, adjuvant, or pharmaceutically acceptable formulating solution. The invention also provides a delivery device pre-filled with the bARE compositions of the invention.

EXAMPLES

The materials and associated techniques and apparatuses of the present invention will now be described with reference to several embodiments. Important properties and characteristics of the described embodiments are illustrated in the structures in the text. While the invention will be described in conjunction with these embodiments, it should be understood that the invention it is not intended to be limited to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Example 1

Separation of $AB_5$ and $B_5$ Forms of LTK63 in GF-HPLC

LTK63, an oligomeric protein of about 82 KDa, is a non-toxic mutant of LT (heat-labile enterotoxin), obtained by site specific mutagenesis on subunit A that retains the structural organization of the native molecule. LTK63 subunit A is composed by a single polypeptidic chain of 240 aminoacids, with a MW of 27 KDa. Subunit B is a pentamer formed by 5 identical monomers of 103 amino acids each, with a MW of 55 KDa. Both subunits contain high percent of positive charged amino acids (subunit A IP=6.3; subunit $B_5$, IP=9.1; integral $AB_5$ IP=8.5).

Analytical techniques conventionally used to characterize the LTK63 protein (electrophoresis, immunoblotting, mass spectrometry and amino acid analysis) cannot distinguish the integral $AB_5$ form of the molecule from the dissociated A or $B_5$ subunit forms. Conventional GF-HPLC systems do not permit a good separation of the $AB_5$ and $B_5$ peaks because of their extremely close retention times. A novel GF-HPLC system allows an effective separation.

A comparative example follows:

Conventional GF-HPLC Analysis on TSK G3000SWxl

Instrument: Alliance 2695 Waters

Buffer: KPi 100 nM+$Na_2SO_4$ 100 mM pH 7,2

Flow: 0,5 ml/min

Detection: PDA 996® 214 and 280 mm

Column: TSK G3000SWxl Tosoh

Material: silica gel

Surface mod: residual —OH groups

Particle size: 5 μm

Porosity: 250 A

Samples of LTK63 ($AB_5$ protein) in three different known conventional buffers (PBS, 0.25% CHAPS and citrate) were run on this chromatographic system. The difference in retention times (RT) of the $AB_5$ and $B_5$ forms using this system is minimum and the peaks are not well resolved, making it difficult to determine $B_5$ subunit form content in LTK63 samples.

Referring to FIG. 1A, it can be seen that at time zero (immediately following sample preparation), there is a single peak in the chromatogram presumed to represent integral AB$_5$. Superimposition of the respective chromatograms for the three samples showed RT and peak profiles are almost identical. Referring to FIG. 1B, after five days, a second peak, presumably corresponding to the B$_5$ form and evidencing some dissociation of the AB5 protein, appears shifted to the right. However, the separation is mimimal and does not permit a quantitative determination of the extent of dissociation of the AB$_5$ molecule.

New GF-HPLC analysis on Ultrahydrogel 250
Instrument: Alliance 2695 Waters
Buffer: KPi 100 nM+Na$_2$SO$_4$ 100 mM pH 7,2
Flow: 0,5 ml/min
Detection: PDA 996® 214 and 280 nm
Column: Ultrahydrogel 250 Waters
Material: hydroxilated polymetacrylate
Surface mod: residual —COOH groups
Particle size; 6 μm
Porosity: 250 A FIG. 1C depicts the chromatogram of the same five day old samples repeated on the new chromatographic system, in accordance with the present invention, clearly showing two well-resolved peaks representative of the B$_5$ (left peak) and AB$_5$ (right peak) forms, respectively. Substantial degradation of the sample is seen for all three of the conventional buffers, in particular the citrate buffer.

Figure 1D:
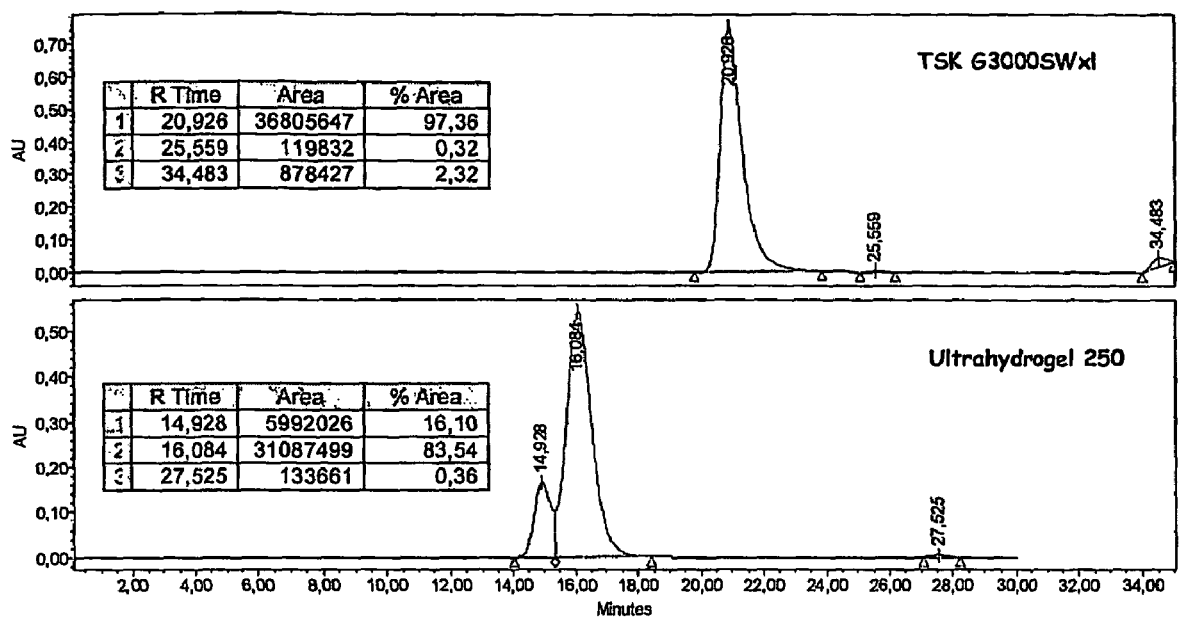
FIG. 1D compares values of Area and Area % obtained for the same LTK63 sample when run on the 2 different columns, which are "old" GF-HPLC analysis on TSK G3000SWxl and "New" GF-HPLC analysis on Ultrahydrogel 250 under the same analytical conditions.
Figures 2A, 2B, 2C, 2D:
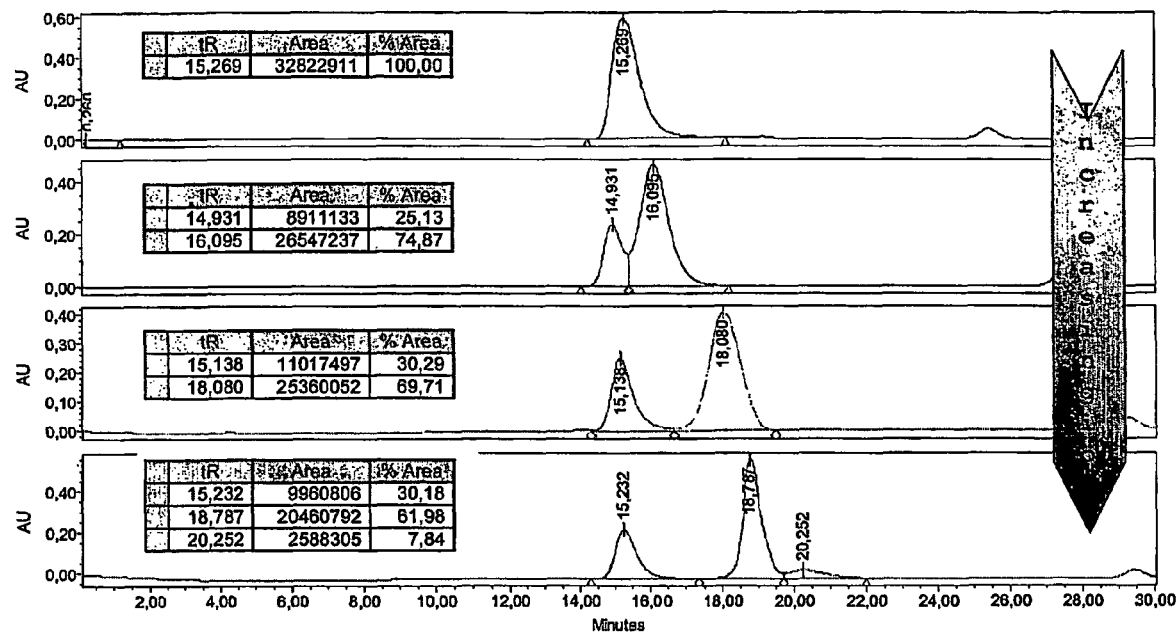
FIGS. 2A-D depict chromatograms which illustrate the effect of ionic strength on selectivity of $AB_5$ and $B_5$ forms in a chromatographic system in accordance with the present invention.

FIG. 1D provides a comparison of LTK63 sample run on TSK G3000SWxl and Ultrahydrogel 250 and SDS-PAGE. It appears that the peak with the smaller retention time (RT) using the Ultrahydrogel 250 column is the B5 subunit peak. This resolution suggests either that the separation mechanism is not purely a Gel Filtration mechanism or that the relative dimensions of the molecules are not proportional to their molecular weight (MW). FIG. 1D also provides a comparison of the values of Area and Area % obtained for the same LTK63 sample using the different columns under the same analytical conditions. The Area % for the LTK63 sample separated on the Ultrahydrogel 250 column is 16% B5:83% AB5 which is an Integrity Ratio of about 1:5 for B5:AB5.

Example 2

Optimizing Elution Conditions

Table 1 shows the composition of four buffers used to elute a partially dissociated AB$_5$ sample (containing both AB$_5$ and B$_5$ forms) from the Ultrahydrogel column separation system described in Example 1.

peak remains substantially unchanged with changing ionic strength.

Figure 3:
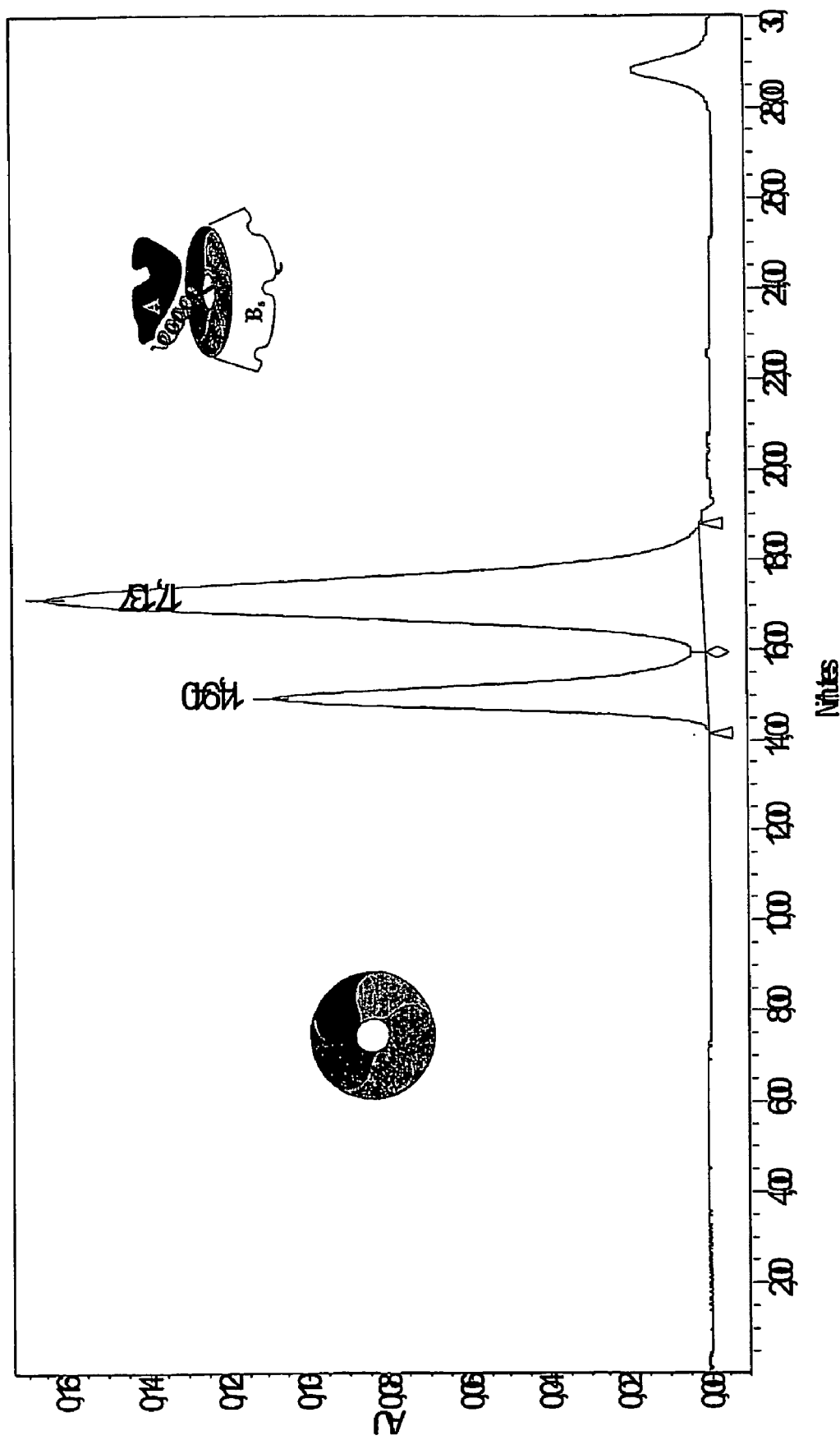
FIG. 3 illustrates the chromatographic profile of a partially dissociated LTK63 sample on a chromatographic system in accordance with the present invention using the following elution buffer: KPi 200 mM+$Na_2SO_4$ 100 mM; pH 7.2.

FIG. 3 illustrates the chromatographic profile of the LTK63 sample in the following elution buffer: KPi 200 mM+Na$_2$SO$_4$ 100 mM; pH 7.2. This buffer provides an ideal AB$_5$/B$_5$ separation in this chromatographic system.

Example 3

Attributing AB$_5$ and B$_5$ Peaks

Fractionation and SDS-PAGE

Figure 4:
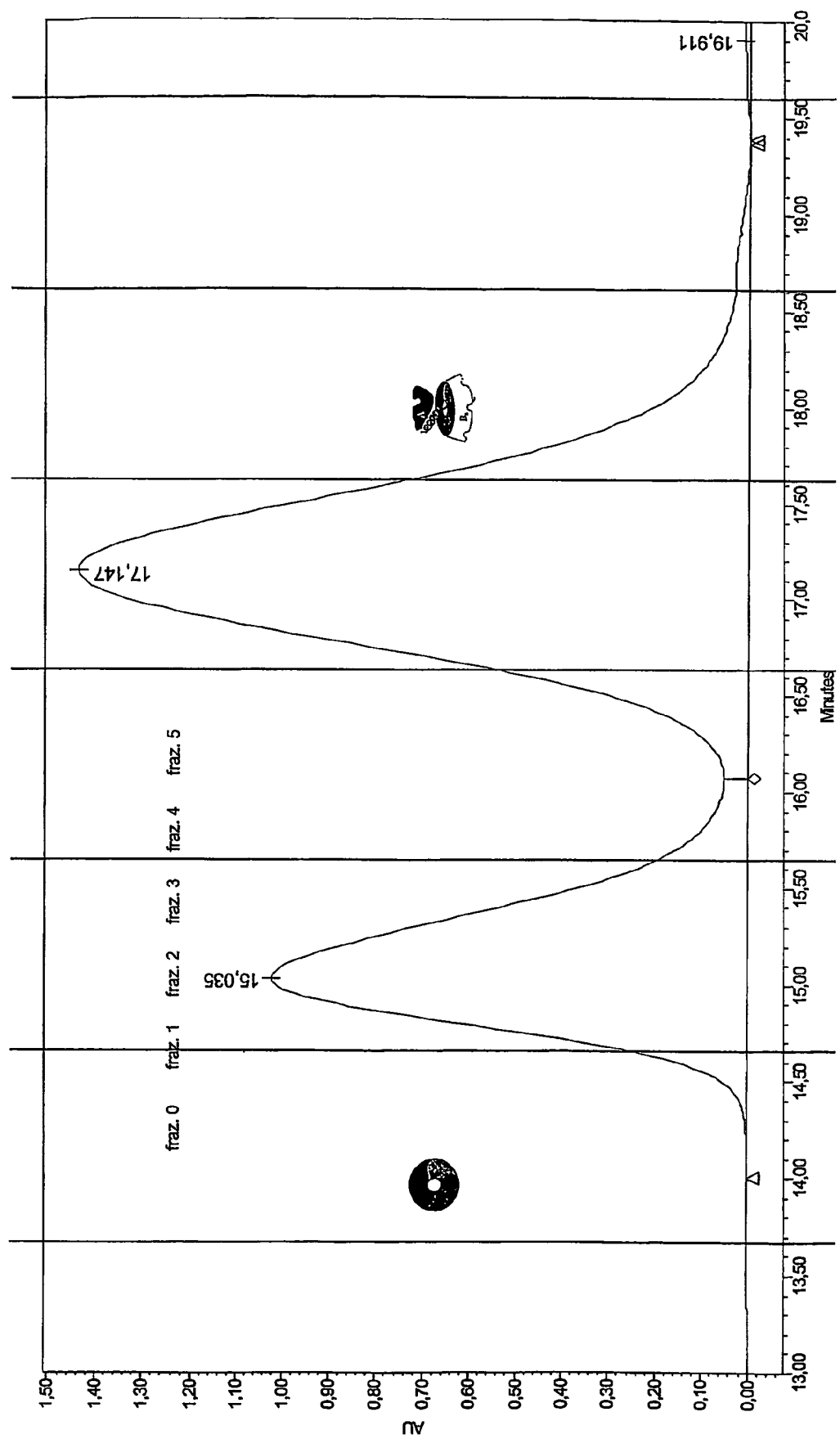
FIG. 4 illustrates the chromatogram of a partially dissociated LTK63 sample on a chromatographic system in accordance with the present invention. In particular.
Figure 5A:
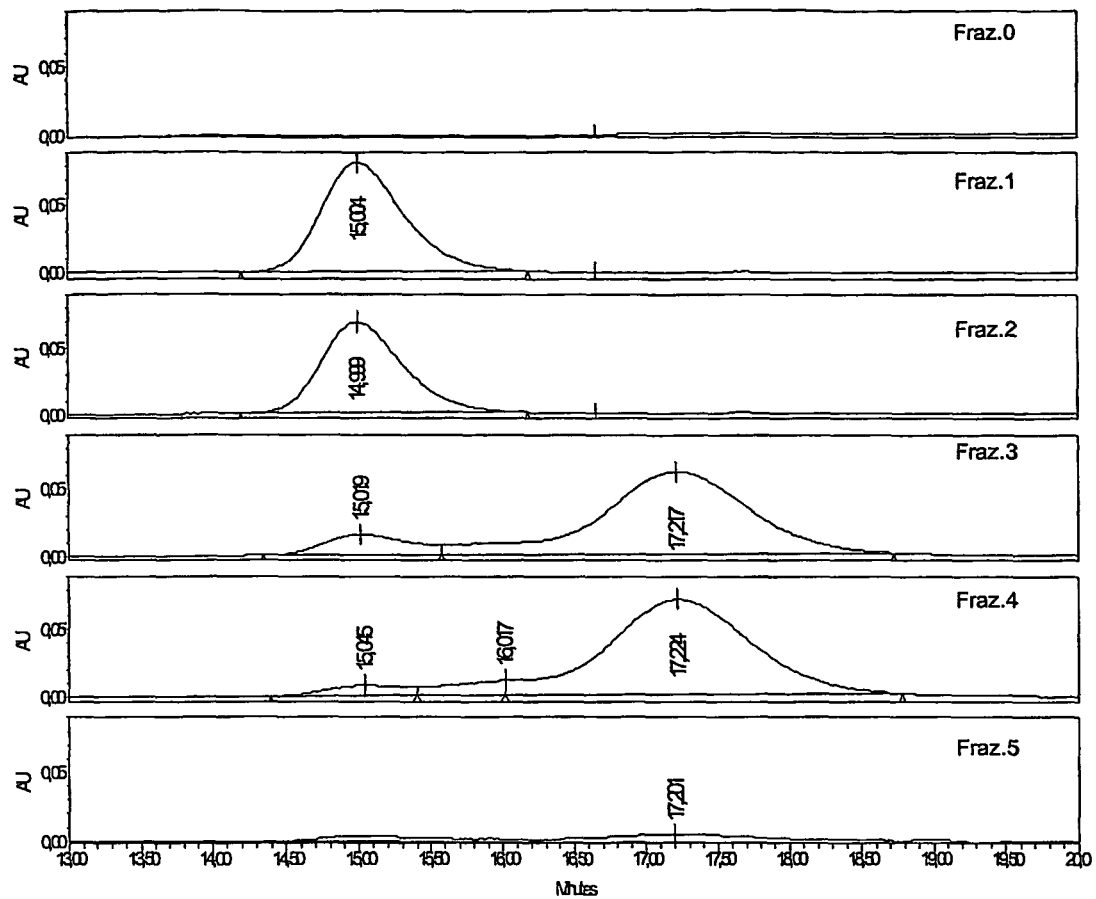
FIGS. 5A and 5B, respectively, show the chromatograms and SDS-PAGE autoradiograms of fractions of the LTK63 sample whose separation is shown in FIG. 4 to verify the attribution of peaks obtained in the GF-HPLC separations to the $AB_5$ and $B_5$ forms of the protein.
Figure 5B:
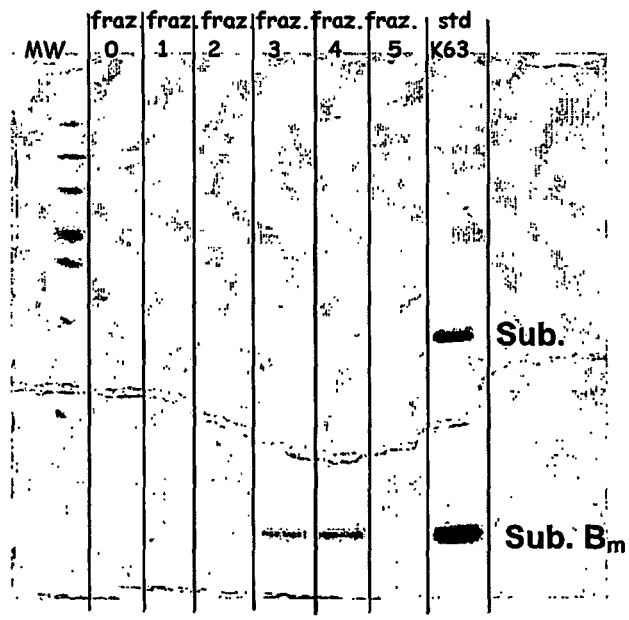

To verify the attribution of peaks obtained in the GF-HPLC separations in accordance with the present invention to the AB$_5$ and B$_5$ forms of the protein, a partially dissociated LTK63 sample was separated as shown in the chromatogram of FIG. 4. The sample was fractionated for further investigation. For fractionation, the sample was injected three times on the new chromatographic system described in Example 1 and six fractions of 500 μl volume were collected for each run from 13.8 to 19.8 minutes. The same fractions of each run were then pooled to obtain a final volume of 1.5 ml/fraction. Fractions 0-5 were then re-injected on the HPLC system and analyzed by SDS-PAGE. The results are shown in FIGS. 5A and 5B, which show the chromatograms and SDS-PAGE profiles, respectively, of fractions of the LTK63 sample whose separation is shown in FIG. 4. The peak with the lower retention time (RT), present in fractions 1 and 2, contains only B$_5$, while peak with the higher RT, present in fractions 3 and 4 migrates in SDS-PAGE as 2 distinct bands of A and B$_m$, representing AB$_5$.

Dimensional Characterization: Apparent Molecular Weight

Figures 5C, 5D:
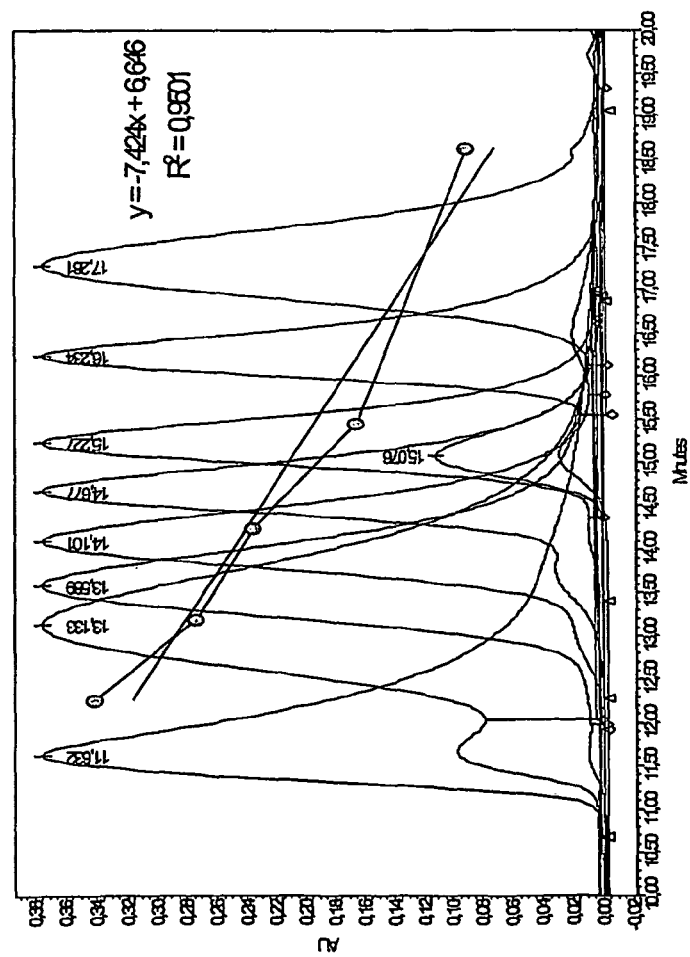
FIGS. 5C and 5D provide a calibaration curve of the Ultrahydrogel column which was made with standard proteins of known MW. The corresponding R2 was 0.95.

A calibration curve of the Ultrahydrogel column was made with standard proteins of known MW. The corresponding R$^2$ was 0.95 (FIG. 5C).

Peak's retention time of CRM197 refrerence protein on the curve gave an apparent MW of 57 KDa (56,9 theoretical); B$_5$ apparent MW on the same curve resulted 65 KDa (55 theoretical). AB$_5$ MW resulted 9,6 KDa (82 kDa theoretical), confirming that separation mechanisms other than Gel Filtration act in this case (see FIG. 5D).

Dimensional Characterization: Light Scattering Analysis

Further characterization of the GF-HPLC peaks was obtained by the use of an online Light Scattering (MALLS)

TABLE 1

| Sample Name | Date Aquired | Eluent | Injection Volume | Channel | Dilution |
|---|---|---|---|---|---|
| 1. PBS 5gg agotazione | Sep. 04, 2003 9.55.19 | KPi 50 mM + Na2SO4 50 mM ph 7.2 | 100.00 | 214 nm | 4.00 |
| 2. PBS 5gg agotazione | Aug. 04, 2003 13.53.06 | KPi 100 mM + Na2SO4 100 mM ph 7.2 | 100.00 | 214 nm | 4.00 |
| 3. PBS 5gg agotazione | Sep. 04, 2003 15.07.11 | KPi 250 mM + Na2SO4 100 mM ph 7.2 | 100.00 | 214 nm | 4.00 |
| 4. PBS 5gg agotazione | Oct. 04, 2003 9.51.42 | KPi 200 mM + Na2SO4 200 mM ph 7.2 | 100.00 | 214 nm | 4.00 |

Figure 5E:
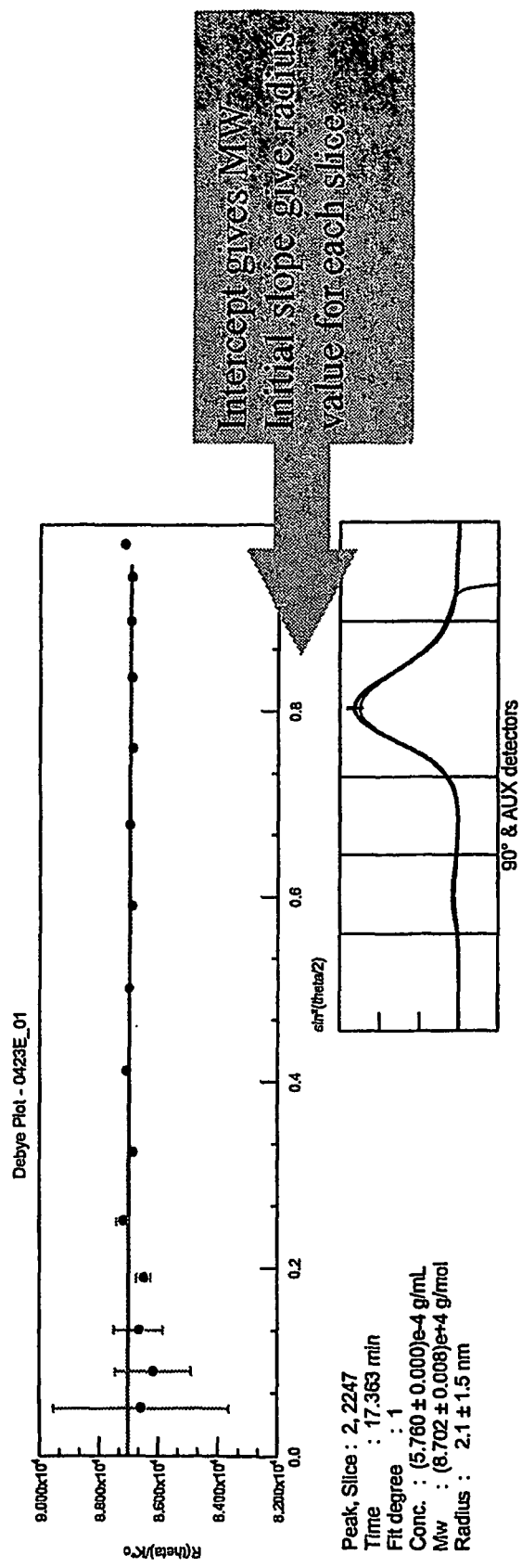
FIG. 5E provides a Debye plot relative to Light Scattering (LS) analysis of the AB5 peak. The intercept gives the MW while the initial slope gives the radius value for each slice.

FIGS. 2A-D depict chromatograms which illustrate the effect of ionic strength on selectivity of AB$_5$ and B$_5$ forms in the system. Higher ionic strength causes a greater net separation of the two peaks, until partial degradation of AB$_5$ when saline concentration reaches 200 mM. The AB$_5$ peak is more affected by ionic strength variation, while the RT of the B$_5$ detector coupled to GF-HPLC: 18 angle Dawn EOS Wyatt (see FIG. 5E). The intercept gives MW. The initial slope gives radius value for each slice.

Table 2, below, groups MALLS data for three different LTK63 samples and for BSA used as control. The following parameters are indicated: absolute MW in Daltons; peak poly-dispersion (value of 1 for mono-dispersed molecules=proteins); gyration radius in nm (measure of molecular dimension; sens. lower limit=10 nm); percent next to each value indicates instrument variability.

In all the samples, the peak with the higher RT ($AB_5$) shows a smaller value of gyration radius in comparison with $B_5$. A possible explanation of this unusual chromatographic behavior of $AB_5$ molecule is that, despite its heavier MW, its conformation is more compact than $B_5$ alone. The results are quite similar for all the LTK63 samples: two mono-dispersed peaks are present, with a MW of about 57 and 85 KDa in accord with the expected values for $B_5$ and $AB_5$, respectively.

indicated that separation mechanisms other than Gel Filtration were acting least for the elution of the $AB_5$ protein.

Thirdly, dimensional characterisation using on-line Light Scattering (MALLS) were carried out to check if absolute MW results were in accord with theoretical values for $AB_5$ and $B_5$ subunit.

The results indicated that peaks were composed of homogenous material. However, dimensional values suggest that $AB_5$ was in a more compact conformation than the $B_5$ subunit alone. The dimensional characterisation obtained using LC-ESI-MS also provided additional evidence of peak attribution.

TABLE 2

| sample | peak | $Mw_{theor}$ | $MW_{exp}$ | % | Polydisp. MwMn | % | Rz | % |
|---|---|---|---|---|---|---|---|---|
| BSA | monomer | 66.800 | 65.970 | 0.3 | 1.000 | 0.5 | 6.5 | 5 |
| K63 in 20 mM phosphate | $AB_5$ | 82.000 | 85.450 | 0.3 | 1.001 | 0.4 | 5.1 | 5 |
| K63 in 0.05% chaps | $AB_5$ | 82.000 | 85.300 | 0.3 | 1.001 | 0.5 | 6.5 | 6 |
| K63 in 0.25% chaps | $AB_5$ | 82.000 | 85.470 | 0.3 | 1.000 | 0.4 | 4.3 | 5 |
| K63 in 20 mM phosphate | $B_5$ | 55.000 | 58.030 | 0.4 | 1.000 | 0.6 | 16.5 | 3 |
| K63 in 0.05% chaps | $B_5$ | 55.000 | 57.030 | 0.4 | 1.000 | 0.6 | 15.2 | 5 |
| K63 in 0.25% chaps | $B_5$ | 55.000 | 57.530 | 0.5 | 1.000 | 0.6 | 19.9 | 5 |

Dimensional Characterization: LC-ESI-MS

Native LTK63 and 3 samples obtained by GF-HPLC fractionation were analysed on LC-ESI-MS to confirm peak attribution. The details of the instrument used are as follows:
Instrument: Alliance 2695 Waters
Detection: PDA 996 Waters
MS ZQ 4000 Micromass
RP column: Jupiter Phenomenex C4
300 Å

Figure 5F:
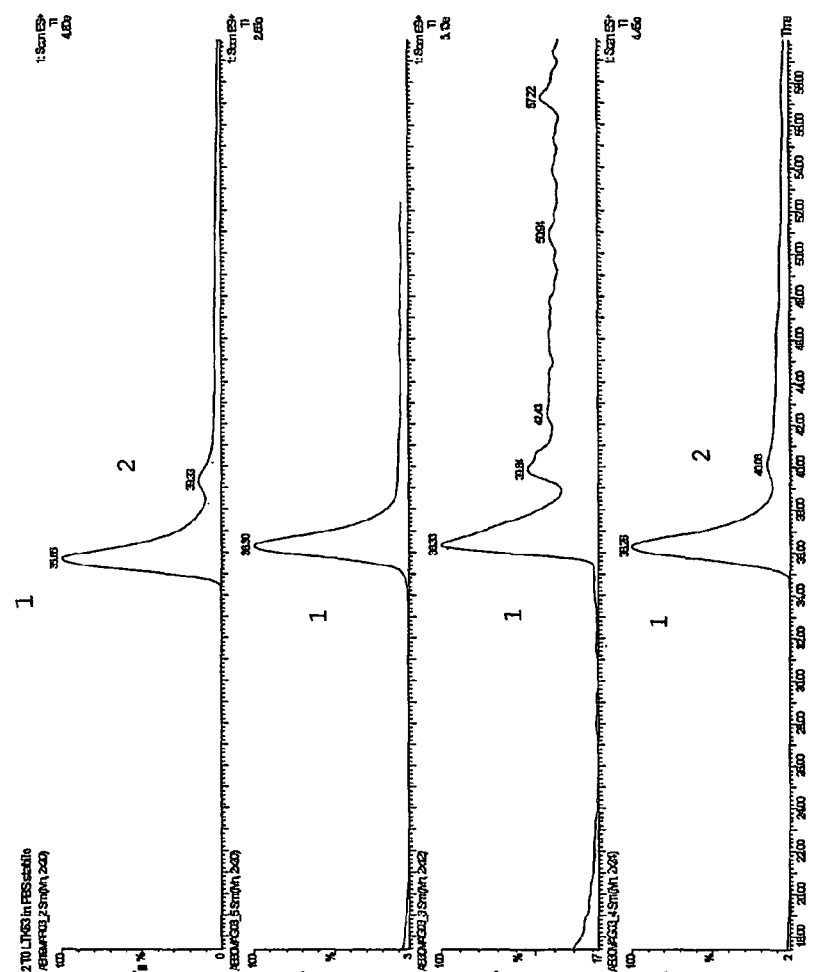
FIG. 5F(a) and FIG. 5F(b) shows an analysis of native LTK63 and three samples obtained by GF-HPLC fractionation on LC-ESI-MS to confirm peak attribution.
Figure 5F:
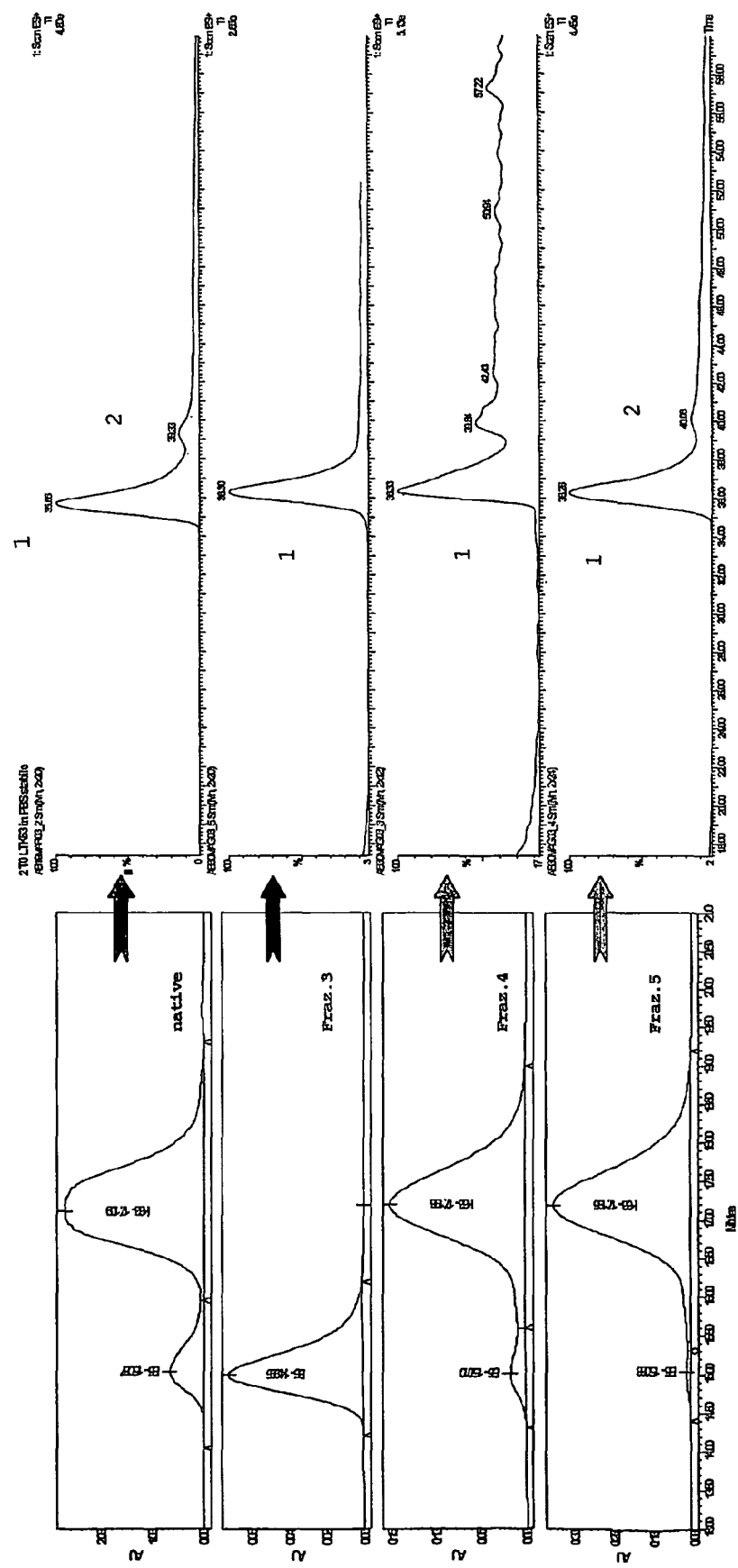
Figure 5G:
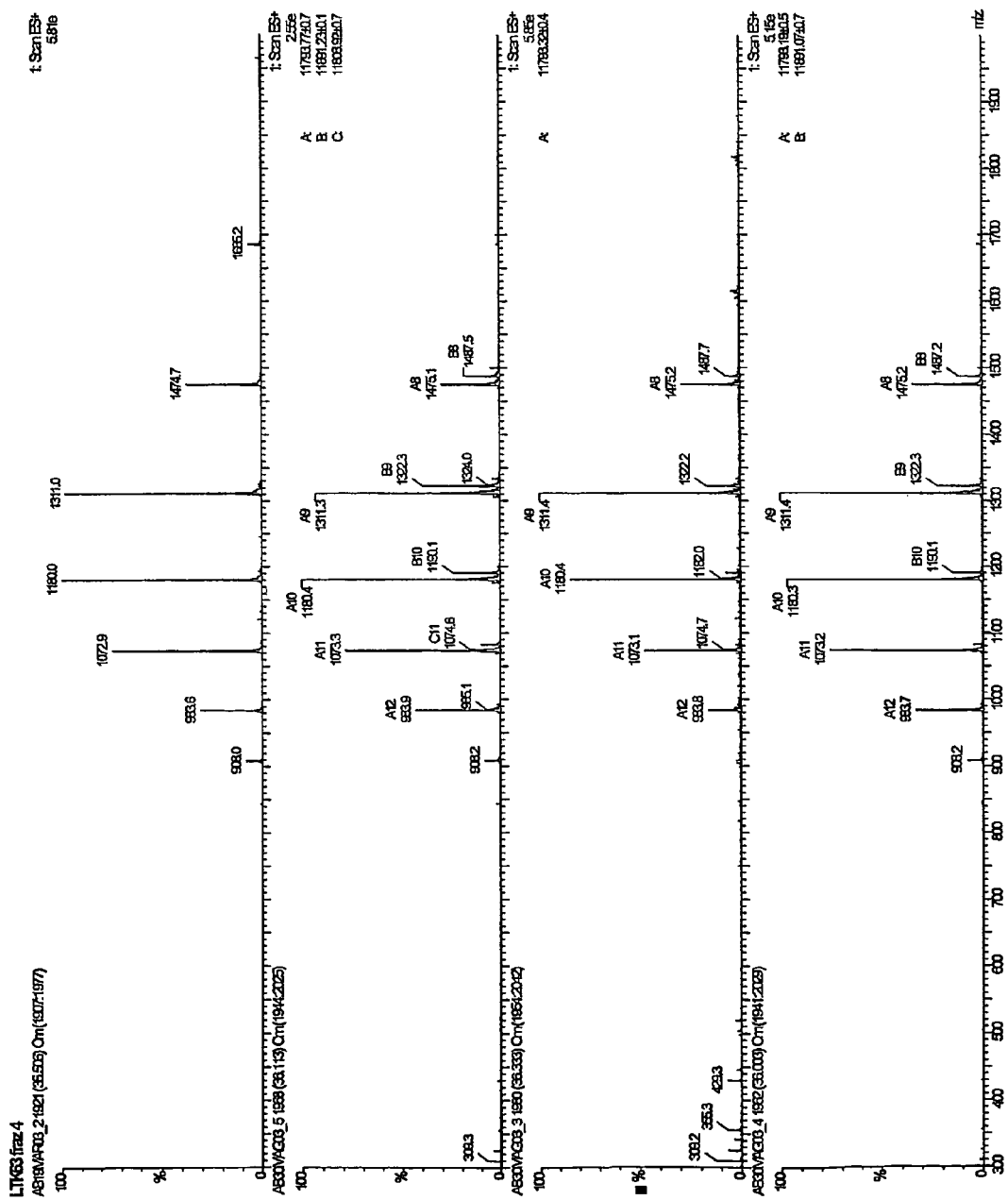
FIG. 5G shows an MS spectrum of peak 1.
Figure 16:
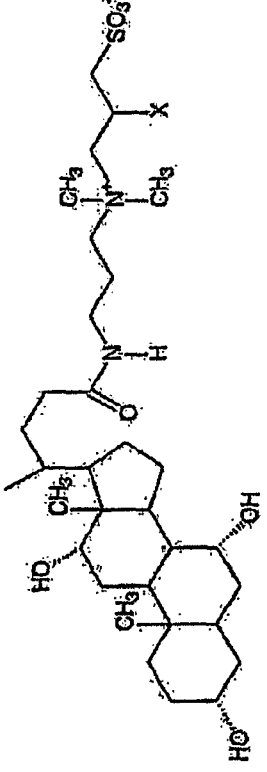
FIG. 16 provides the structure of zwitterionic detergents such as CHAPS and CHAPSO.

FIG. 5F(b) shows that Peak 1 with a MW of about 11.793 Da corresponding to the B monomer was present in native LTK63 and in all fractions. FIG. 5F(b) also shows that Peak 2 with a MW of 27.855/66Da corresponding to subunit A was present in the native LTK63 fraction and in fraction 5.

Summary of Results from Examples 1-3

(Comparative Examples Between Old and New HPLC Technique)

A novel GF-HPLC method was developed which is an important contribution to the art because the functional integrity of an bARE protein, such as an AB5 protein, can be evaluated without a loss of its integral multimer structure.

The functional stability of a bARE protein, such as an AB5 protein, may be determined in terms of non-dissociated and dissociated forms of the AB5 protein; and The impact of candidate stabilising agents on the functional stability of the bARE protein may be determined. In particular the impact of physical stabilising agents on the functional stability of a bARE protein, such as an AB5 protein can be determined. and possibility of its stabilization.

As the Examples demonstrate, elution conditions using the GF-HPLC method were optimised and the effect of ionic strength on the elution buffer was investigated, as ionic strength appeared to influence the retention time of the $AB_5$ protein on the column.

The peaks eluted from the GF-HPLC column were characterised in a number of ways: First of all, peak attribution was verified by both fractioning and SDS-PAGE analysis in order to identify the eluted $B_5$ and $AB_5$ peaks.

Secondly, dimensional characterisation was carried out using apparent Molecular Weight (MW) determination which Example 4

Application of the Novel Analytical Method (GF-HPLC) of the Present Invention in Screens for Stabilising Agents Prior to the development of the analytical method of the present invention and the identification of stabilising agents and their effects on the physical and/or functional stability of a bARE protein, stability problems were observed during the long term storage of a purified concentrated bulk of a bARE protein, such as the mutant LT K63 protein in different buffers and at different storage temperature.

By way of example, LT K63 bulk stored at 4° C. in PBS at a protein concentration of 2.8 mg/ml after 1 month showed the formation of several "crystals" on the bottle wall.

There was also evidence of LT K63 precipitation at a protein concentration of 1-1.5 mg/ml after 5 months of storage at 2-8° C. in Phosphate Buffer Saline (PBS) pH 7.4. The SDS-PAGE analysis of precipitated samples indicate precipitation of the whole AB5 protein.

LT K63 bulk stored at −20° C. in PBS doesn't show precipitation but in HPLC analysis the appearance of the $B_5$ complex was observed which suggested that the $AB_5$ protein was dissociating into A and $B_5$ subunit forms. In addition, the application of the novel GF-HPLC analytical method of the present invention indicated that there was evidence of loss of LT K63 integrity as detected by HPLC, after 10 months of storage at −20° C. in PBS+5% sucrose at a a protein concentration of 1.2 mg/ml.

Addition of 5% sucrose to PBS seemed to protect LT K63 by dissociation in freeze/thawing cycles. However, in the long term storage at −20° C. of LT K63 in PBS plus 5% sucrose protein dissociation occurred again.

Accordingly, one of the objects of the present invention was to provide an improved storage bARE composition, in particular an improved AB5 storage composition, to stabilize the Purified Concentrated Bulk of LT K63 at 2-8° C. to a protein concentration range of between 1 mg/ml-4 mg/ml.

Methodology

A first attempt to stabilize LT K63 avoiding precipitation/crystallization was performed at 4° C. with variation of sev eral parameters affecting protein stability. Various buffers, such as acetate, citrate, phospate and Tris buffers were chosen. The NaCl concentration was varied in the range of 0-0.5M; the pH was varied in the range of 5.5-7.5; and various additives such as sugars, detergents, chelators and aminoacids were used. Protein concentration was maintained in the range 0.8-1.2 mg/ml in all the storage buffers used. The experiments were performed in static conditions and by shaking the samples in a rotor agitator at 4° C. The shaking experiments were set up to stress the storage conditions and to accelerate the precipitation of LT K63.

Screening Results 4 (a)

TABLE 3

| BUFFER | precipitation shaken | precipitation static |
|---|---|---|
| PBS | Yes | Yes |
| PBS + galactose 0.1 mM | Yes | no |
| PBS + trealose 5% | Yes | Yes |
| PBS + CHAPS 0.25% | no | no |
| PBS + amino caproic acid 5% | Yes | Yes |
| Pi 20 mM pH 7.4 | Yes | Yes |
| Pi 50 mM, NaCl 0.3 M, galactose 0.2M p | Yes | Yes |
| Pi 20 mM pH 7.4 + L-Arginine 0.4M | no | no |
| Acetate 50 mM, NaCl 300 mM pH 5.5 | Yes | Yes |
| Citric Acid 50 mM pH 6.5 | Yes | no |
| Tris 50 mM, 1 mM EDTA pH 7.5 | Yes | Yes |
| Tris 50 mM, 1 mM EDTA, 200 mM NaCl | Yes | no |
| NaCl 500 mM pH 5.8 | Yes | no |

An analysis of the Results in Table 3 indicated that precipitation of shaken samples occurs in a few days whereas under static conditions, precipitation takes several months. Two additives, CHAPS and L-Arginine were chosen that prevented precipitation of LT K63 precipitation both under static and shaken conditions.

Screening Results 4(b)

Analysis by SDS-PAGE of the pellets (not shown) and the supernatants (see FIG. 6) at 1 and 6 days of shaking has been performed. Unlike static samples, in shaking conditions a partial dissociation of $AB_5$, dependent on storage buffers, occurs and the supernatant is enriched of B monomer ($B_m$) or an oligomeric form of B subunit ($B_x$).

Example 5

The SDS-PAGE results of Example 4(b) indicated that under shaking conditions, LT K63 protein is unstable and the A and B subunits dissociate. The effect of two storage buffers, CHAPS and L-Arginine on the stability of the LTK63 protein was examined. Two storage buffers were chosen: 20 mM phospate pH 7.4 and CHAPS and 20 mM phospate pH 7.4 and L-Arginine.

Results 5 (a)

FIG. 7 shows that: Both under static and in shaking conditions, increasing protein concentration up to 1.5-2.0 mg/ml affects LT K63 precipitation; On the other hand, CHAPS concentration in the range 0.05%-0.5% doesn't affect significantly the LT K63 behaviour; and the SDS-PAGE of CHAPS precipitated samples did not show an LT K63 dissociation both in static and in shaking conditions.

Summary of Results 5 (a)

For protein concentration higher than 1.5 mg/ml, the inclusion of CHAPS does not appear to have a protective effect on LT K63 precipitation. However, the inclusion of CHAPS appears to protect the $AB_5$ protein from dissociation into its subunit form.

Results 5(b)

FIG. 8 shows that under static conditions, increasing protein concentration up to 17 mg/ml did not influence protein precipitation whereas under shaking conditions, LT K63 precipitation occurs even at concentrations of 2.0 mg/ml; L-arginine concentration in the range 50 mM-400 mM doesn't affect significantly the LT K63 precipitation; while SDS-PAGE of L-Arginine precipitated samples under shaking conditions seemed to indicate an LT K63 dissociation.

Summary of Results 5(b)

L-Arginine was able to prevent protein precipitation up to very high protein concentration but L-Arginine appears to have an effect on LT K63 dissociation.

Example 6

Comparative analysis of L-Arginine shaken samples after 30 days of shaking using Old HPLC method and New HPLC method.

Results 6

An analysis of FIGS. 9(*a*) and 9(*b*) shows that the old HPLC method (FIG. 9(*a*) fails to discriminate between the native multimeric AB5 protein and its dissociated B5 subunit form whereas the new HPLC method permits not only a resolution of the AB5 and B5 forms but also a quantitation of the relative amounts of the dissociated and non-dissociated forms using different concentrations of Arginine (0.2M, 0.3M and 0.4M) by calculating the percent area under the peaks obtained using the analytical method of the present invention.

Summary of Results 6

The extent of LT K63 dissociation determines the appearance of the $B_5$ subunit form which occurs even in non-precipitated samples and seems to be dependent on L-Arginine concentration.

Example 7

The dependence of LT K63 dissociation on L-Arginine concentration was studied using the novel HPLC analytical method of the present invention under static samples at different LT K63 concentrations (1.3 mg/ml and 4.0 mg/ml).

Results 7

An analysis of FIGS. 10(*a*) and 10(*b*) indicates that: $B_5$ increase occurs even in static samples and is dependent on L-Arginine concentration. The slope of linear regression analysis indicated that the extent of dissociation of the AB5 protein was not dependent on the AB5 protein concentration.

Example 8

Methodology

The CHAPS effect on LT K63 dissociation under static conditions was evaluated using the novel HPLC method of the present invention. An analysis of FIGS. 11(*a*) and 11(*b*) indicated that the inclusion of CHAPS does not have a dissociating effect on LT K63 (FIG. 11(*a*)); and that the $B_5$ increase in L-Arginine treated samples was partially inhibited by addition of 0.05% CHAPS (FIG. 11(*b*)).

Overall Summary of Results 4-8

LT K63 instability is dependent on two different phenomena: crystallization/precipitation and dissociation. Two additives, CHAPS and L-Arginine were selected to synergistically stabilize the LT K63 protein. Although CHAPS is unable to prevent LT K63 precipitation at high LT K63 concentration (about 2 mg/ml), no dissociating effect has been observed. L-Arginine prevents protein precipitation at a very high LT K63 concentration (about 17 mg/ml) but L-Arginine may have an effect on $AB_5$ dissociation.

As regards the combination of CHAPS+L-Arginine as a stabilising additive, the inclusion of CHAPS partially inhibits the $B_5$ subunit formation in L-Arginine samples and when included in combination with L-Arginine, the expected increase in $B_5$ levels over a period of 12 months was around 1.5%. On the basis of these observations the use of a combination of CHAPS and L-Arginine appears to provide a synergistic effect in terms of preventing both LTK63 precipitation and dissociation over time. In particular, stability experiments to determine the optimal L-arginine (100-200 mM) and CHAPS (0.05-0.25%) concentration, when used in combination, have shown that positive results in terms of stability were obtained after 3 months irrespective of additive concentration.

Example 9

Effect of L-Arginine and CHAPS on LTK 63 Stability at a Protein Concentration of 1.3 mg/ml Over a Period of Time LTK 63, at a protein concentration of 1.3 mg/ml was maintained at 2-8° C. in storage buffer containing different concentration of L-arginine and CHAPS in order to check the effect of these two stabilizers on protein dissociation and precipitation. The B5 percentage in the samples was measured by HPLC analysis for up to 8 months of storage.

Results 9

Table 4(a) and FIG. 12 shows the effect of L-Arginine (50 mM-400 mM) and CHAPS (0.25%) on LTK 63 stability at a protein concentration of 1.3 mg/ml over a period of time. Protein precipitation (ppt) was observed in the control sample and the shaken sample after 118 days which is about 4 months. No precipitation was observed in any of the static samples after 118 days. However, precipitation was observed in two of the five static samples after 246 days, which is about 8-9 months.

A linear fitting of the time course of B5 percentage was plotted.

TABLE 4(b)

| Buffer | Linear Fitting | |
|---|---|---|
| phosphate 20 mM, pH 7.4 | y = −0.0033x + 2.8087 | R2 = 0.291 |
| phosphate 20 mM, pH 7.4 + 50 mM arginina STATIC | y = 0.0025x + 2.7218 | R2 = 0.2749 |
| phosphate 20 mM, pH 7.4 + 100 mM arginina STATIC | y = 0.0054x + 2.8192 | R2 = 0.9181 |
| phosphate 20 mM, pH 7.4 + 200 mM arginina STATIC | y = 0.0065x + 3.0439 | R2 = 0.9708 |
| phosphate 20 mM, pH 7.4 + 400 mM arginina STATIC | y = 0.0092x + 3.5354 | R2 = 0.9718 |
| phosphate 20 mM, pH 7.4 + CHAPS 0.25% STATIC | y = −0.0022x + 2.3684 | R2 = 0.3759 |
| phosphate 20 mM, pH 7.4 + CHAPS 0.25% SHAKEN | y = −0.0049x + 2.3334 | R2 = 0.3239 |

Example 10

Methodology

The effect of CHAPS (0.05%) and L-Arginine (50 mM-400 mM) on protein dissociation and precipitation was examined over time (0, 2, 5, 12, 27, 55, 118 and 256 days).

LTK 63, at a protein concentration of 4.0 mg/ml was maintained at 2-8° C. in a storage buffer containing different concentration of L-Arginine and the combination L-Arginine+CHAPS. In only one sample was protein precipitation (ppt) observed after 246 days. The B5 percentage in the samples was measured by HPLC analysis for up to 8 months of storage. The time course of B5 percentage was performed and a linear fitting was plotted (Tables 5(a), 5(b) and FIG. 13).

TABLE 4(a)

| | % $B_{5\ 214\ nm}$ | | | | | | | |
|---|---|---|---|---|---|---|---|---|
| Buffer | 0 day | 1 day | 6 days | 13 days | 27 days | 55 days | 118 days | 246 days |
| Phosphate 20 mM, pH 7.4 | 2.90 | 2.80 | 2.83 | 2.56 | 2.79 | 2.64 | ppt | |
| Phosphate 20 mM, pH 7.4 + 50 mM arginina STATIC | 2.99 | 2.56 | 2.82 | 2.50 | 2.87 | 2.82 | 3.04 | ppt |
| Phosphate 20 mM, pH 7.4 + 100 mM arginina STATIC | 3.03 | 2.86 | 2.94 | 2.69 | 2.94 | 3.08 | 3.29 | 4.26 |
| Phosphate 20 mM, pH 7.4 + 200 mM arginina STATIC | 3.12 | 3.13 | 3.09 | 2.92 | 3.3 | 3.36 | 3.79 | 4.65 |
| Phosphate 20 mM, pH 7.4 + 400 mM arginina STATIC | 3.64 | 3.58 | 3.53 | 3.40 | 3.80 | 4.11 | 4.80 | 5.71 |
| Phosphate 20 mM, pH 7.4 + CHAPS 0.25% STATIC | 2.61 | 2.31 | 2.33 | 2.30 | 2.18 | 2.20 | 2.17 | ppt |
| Phosphate 20 mM, pH 7.4 + CHAPS 0.25% SHAKEN | 2.61 | 2.21 | 2.23 | 2.20 | 2.12 | 2.13 | ppt | |

TABLE 5(a)

| Buffer | % B5 214 nm | | | | | | | |
|---|---|---|---|---|---|---|---|---|
| | 0 day | 2 days | 5 days | 12 days | 27 days | 55 days | 118 days | 246 days |
| phosphate 20 mM, pH 7.4 + 50 mM arginina STATIC | 3.57 | 2.65 | 3.24 | 2.95 | 3.54 | 3.40 | 3.53 | ppt |
| phosphate 20 mM, pH 7.4 + 100 mM arginina STATIC | 3.51 | 2.68 | 3.27 | 2.92 | 3.6 | 3.41 | 3.76 | 3.94 |
| phosphate 20 mM, pH 7.4 + 200 mM arginina STATIC | 3.65 | 2.73 | 3.12 | 3.16 | 3.79 | 3.67 | 3.94 | 4.21 |
| phosphate 20 mM, pH 7.4 + 400 mM arginina STATIC | 3.93 | 3.27 | 3.9 | 3.64 | 4.36 | 4.42 | 4.89 | 5.80 |
| phosphate 20 mM, pH 7.4 + 200 mM arginina + CHAPS 0.05% STATIC | 2.72 | 2.78 | 2.78 | 2.74 | 2.91 | 2.98 | 3.15 | 3.41 |

TABLE 5(b)

| Buffer | Linear Fitting | |
|---|---|---|
| fosfato + 50 mM arginina ST | y = 0.0037x + 3.1542 | R2 = 0.1999 |
| fosfato + 100 mM arginina ST | y = 0.0035x + 3.1827 | R2 = 0.5089 |
| fosfato + 200 mM arginina ST | y = 0.0043x + 3.2841 | R2 = 0.565 |
| fosfato + 400 mM arginina ST | y = 0.0087x + 3.7714 | R2 = 0.8792 |
| fosfato + 200 mM arginina + CHAPS 0.05% ST | y = 0.0027x + 2.7739 | R2 = 0.9544 |

Discussion of Results 9 and Results 10

The effect of L-Arginine on LTK 63 stability was confirmed in the sense that L-Arginine protects against protein precipitation. When an L-Arginine concentration higher than 50 mM was included, protection against LTK63 precipitation was obtained for up to 8 months of LTK 63 storage (Tables 4 and 5). On the other hand, L-Arginine has a slight dissociating effect on LTK 63 (see FIGS. 12 and 13). The slopes comparison of the linear fittings obtained by the time course of B5 percentage shows that the dissociation is dependent on L-Arginine concentration: That is, the higher the L-Arginine concentration the faster the dissociation (see Tables 4 and 5). However, the dissociating effect is tolerable, as the increase in B5 percentage only ranges from between about 0.1% to about 0.27% per month. The effect of CHAPS on LTK 63 dissociation was also confirmed (Tables 4(b) and 5(b)), although CHAPS does not completely protect against protein precipitation (see Table 4(a)). The LTK 63 concentration appears to have a minor influence on protein dissociation and/or precipitation.

Example 11

Effect of Storage Conditions on LTK63 Stability in L-arginine+CHAPS Containing Buffers LTK 63, at a protein concentration of 2.0 mg/ml was maintained in static and shaken conditions, at 2-8° C. in storage buffer containing 200 mM L-Arginine in combination with different concentration of CHAPS. The B5 percentage in the samples has been measured by HPLC analysis up to 8 months of storage. The time course of B5 percentage has been performed and a linear fitting has been plotted. In several samples precipitation (ppt) of LTK 63 was observed.

TABLE 6(a)

| Buffer | % B5 214 nm | | | | | |
|---|---|---|---|---|---|---|
| | 3 day | 10 days | 24 days | 52 days | 115 days | 243 days |
| phosphate 20 mM, pH 7.4 + 200 mM arginina + CHAPS 0.05% STATIC | 3.28 | 3.4 | 3.49 | 3.56 | 3.81 | 4.31 |
| phosphate 20 mM, pH 7.4 + 200 mM arginina + CHAPS 0.05% SHAKEN | 3.29 | 3.35 | 3.42 | 3.53 | 3.77 | ppt |
| phosphate 20 mM, pH 7.4 + 200 mM arginina + CHAPS 0.25% STATIC | 3.29 | 3.39 | 3.45 | 3.57 | 3.78 | 4.18 |
| phosphate 20 mM, pH 7.4 + 200 mM arginine + CHAPS 0.25% SHAKEN | 3.24 | 3.37 | 3.4 | 3.55 | 3.83 | ppt |

TABLE 6(b)

| Buffer | Linear Fitting | |
|---|---|---|
| phosphate 20 mM, pH 7.4 + 200 mM arginina + CHAPS 0.05% STATIC | y = 0.004x + 3.342 | R2 = 0.9875 |
| phosphate 20 mM, pH 7.4 + 200 mM arginina + CHAPS 0.05% SHAKEN | y = 0.0041x + 3.3033 | R2 = 0.9915 |
| phosphate 20 mM, pH 7.4 + 200 mM arginina + CHAPS 0.25% STATIC | y = 0.0035x + 3.348 | R2 = 0.9852 |
| phosphate 20 mM, pH 7.4 + 200 mM arginina + CHAPS 0.25% SHAKEN | y = 0.0049x + 3.2784 | R2 = 0.9751 |

Discussion of Results 11

LTK 63, even in presence of L-Arginine and CHAPS precipitates on long term shaken storage, that is, after 8 months (see Table 6(a)). However, shaking has no effect on protein dissociation (FIG. 14), the inclusion of CHAPS concentration (in the range 0.05%-0.25%) has no major effect on the protection of LTK 63 against dissociation, as determined by the slopes of linear fittings (Table 6(b)).

Example 12

Comparison of LTK 63 Stability on L-Arginine and L-Arginine+CHAPS Storage Buffers LTK 63, at a protein concentration of 2,0 mg/ml, has been maintained, in static and shaken conditions, at 2-8° C. in storage buffer containing 200 mM L-Arginine alone or in combination with 0.05% CHAPS. The B5 percentage in the samples has been measured by HPLC analysis up to 7 months of storage. The time course of B5 percentage has been plotted and a linear fitting has been performed.

TABLE 7(a)

| Buffer | % $B_{5\ 214\ nm}$ | | | | |
|---|---|---|---|---|---|
| | 3 days | 18 days | 65 days | 209 days | |
| phosphate 20 mM, pH 7.4 + 200 mM arginina STATIC | 6.97 | | 7.02 | 8.08 | diafiltration without CHAPS |
| phosphate 20 mM, pH 7.4 + 200 mM arginina + CHAPS 0.05% STATIC | 5.62 | 5.8 | 5.86 | 6.62 | |
| phosphate 20 mM, pH 7.4 + 200 mM arginina + CHAPS 0.05% SHAKEN | 5.67 | 5.84 | 5.09 | 6.7 | |
| phosphate 20 mM, pH 7.4 + 200 mM arginina + CHAPS 0.05% STATIC | 5.3 | | 6.27 | 7.11 | diafiltration with CHAPS |
| phosphate 20 mM, pH 7.4 + 200 mM arginina + CHAPS 0.05% SHAKEN | 5.35 | 6.09 | 6.34 | 7.29 | |

TABLE 7(b)

| Buffer | Linear Fitting | | |
|---|---|---|---|
| phosphate 20 mM, pH 7.4 + 200 mM arginina STATIC | y = 0.0057x + 6.827 | R2 = 0.935 | diafiltration without CHAPS |
| phosphate 20 mM, pH 7.4 + 200 mM arginina + CHAPS 0.05% STATIC | y = 0.0046x + 5.6321 | R2 = 0.976 | |
| phosphate 20 mM, pH 7.4 + 200 mM arginina + CHAPS 0.05% SHAKEN | y = 0.0051x + 5.4493 | R2 = 0.516 | |
| phosphate 20 mM, pH 7.4 + 200 mM arginina + CHAPS 0.05% STATIC | y = 0.0083x + 5.4634 | R2 = 0.930 | diafiltration with CHAPS |
| phosphate 20 mM, pH 7.4 + 200 mM arginina + CHAPS 0.05% SHAKEN | y = 0.008x + 5.6758 | R2 = 0.885 | |

Discussion of Results 12

The protective effect of CHAPS against protein dissociation is shown by the comparison of the slopes (Table 6(b)). However, the presence of CHAPS during diafiltration step appears to have a negative effect on the dissociation of LTK 63 (Table 6(b)).

Summary of Results from Examples 4-12

Our stability studies demonstrated that LTK 63 purified concentrated bulk showed a long term instability (over a period of not less than one year) in the sense that precipitation at 2-8° C. and dissociation at −20° C. occurred after several months of storage. The inclusion of L-Arginine in the storage buffer at a concentration higher than 50 mM prevented LTK 63 precipitation at a storage temperature in the range of 2-8° C. over a period of 8 months. The dissociation effect resulting from L-Arginine itself appears to be very slight and is dependent on L-Arginine concentration (the increase in B5 percentage ranging between about 0.1% and 0.27% per month). The inclusion of CHAPS does not prevent LTK 63 precipitation over long term storage. However, the inclusion of at least 0.05% CHAPS can reduce the dissociating effect caused by L-Arginine by from about 60-80%, as determined by the regession analysis slope comparison (Tables 5(b) and 7(b)). The protective effect of the CHAPS against LTK 63 dissociation does not appear to be dependent on CHAPS concentration in the range between 0,05 and 0,25%. The combination of the two stabilizers appears to provide a synergistic effect in terms of prevention of protein precipitation (physical stabilization) and protein dissociation (functional stabilization).

Overall Summary

A novel analytical method was developed for analysing a bARE protein sample under non-dissociating conditions which differentiate between integral and dissociated bARE class proteins. This analytical method makes an important contribution to the art because:

(i) the functional integrity of an bARE protein, such as an AB5 protein, can be evaluated without a loss of its integral multimer structure;

(ii) the functional stability of a bARE protein, such as an AB5 protein, may be determined in terms of non-dissociated and dissociated forms of the AB5 protein; and (iii) the impact of candidate stabilising agents on the functional stability of the bARE protein, such as an AB5 protein may be determined. In particular the impact of physical stabilising agents on the functional stability of a bARE protein, such as an AB5 protein can be determined.

The development of such an analytical method is advantageous for the following reasons.

Firstly, up until now, no analytical method was available for evaluating the integrity of a bARE protein without loss of its integral structure. Accordingly, this is the first time that the existence of a substantially integral bARE protein may be determined.

Secondly, this is the first time that a functional stabilising agent for a bARE protein has been identified. As no method was previously available to determining the functional stability of a bARE molecule under non-dissociating conditions which differentiate between integral and dissociated bARE class proteins, no stabilising agent capable of maintaining the functional stability or integrity of a bARE protein could be identified.

Thirdly, this is the first time that selective bARE stabilising agent has been identified. In particular, stabilising agents capable of physically stabilising a bARE protein without affecting the functional stabilisation of the bARE protein are disclosed herein. Likewise, stabilising agents capable of functionally stabilising a bARE protein without affecting the physical stabilisation of the protein are also disclosed.

Compositions comprising a stabilized bARE polypeptide as a therapeutically active component and methods useful in their preparation are provided. The composition is a stabilized bARE composition that includes a bARE protein whose effectiveness as a therapeutically active component may be compromised during storage as a result of aggregation of the bARE polypeptide. Thus the stabilized bARE compositions of the invention comprise, in addition to a bARE protein that may exhibit aggregate formation during storage in a liquid formulation, an amount of an amino acid base sufficient to decrease aggregate formation of the bARE protein during storage, where the amino acid base is an amino acid or a combination of amino acids, where any given amino acid is present either in its free base form or in its salt form. The compositions may further comprise a zwitterionic agent at an effective concentration to impart functional stability to the bARE protein.

The amino acid base serves to stabilize the bARE polypeptide against aggregate formation during storage of the composition, while the inclusion of a zwitterionic agent imparts functional stability in terms of preserving the integrity of the bARE protein. The bARE composition may additionally incorporate other stabilizing agents to further increase stability of the bARE polypeptide. Such bARE compositions are said to be stabilized, as addition of amino acid base in combination with a zwitterionic agent results in the bARE composition having increased storage stability relative to compositions formulated in the absence of the combination of these two components.

Methods for increasing stability of a bARE polypeptide in a composition and for increasing storage stability of such a composition are also provided. The methods comprise incorporating into the composition an amount of an amino acid base sufficient to decrease aggregate formation of the bARE polypeptide during storage of the composition, and a zwitterionic agent. The methods find use in preparation of the compositions of the invention.

All documents cited herein are hereby incorporated by reference in their entirety and for all purposes. Although the foregoing invention has been described in some detail for purposes of clarity of understanding, it will be apparent that certain changes and modifications may be practiced within the scope of the appended claims. It should be noted that there are many alternative ways of implementing both the processes and compositions of the present invention. Accordingly, the present embodiments are to be considered as illustrative and not restrictive, and the invention is not to be limited to the details given herein, but may be modified within the scope and equivalents of the appended claims.

What is claimed is:

1. A composition comprising a soluble, substantially integral bARE class protein, arginine phosphate and 3-(3-Cholamidopropyl)-dimethylammonio-1-propanesulfonate (CHAPS), wherein the bARE class protein is an AB5 cholera toxin (CT) ADP-ribosylating toxin or an AB5 *E. coli* heat labile toxin (LT).

2. The composition according to claim 1, wherein the Arginine phosphate is present in an amount of from about 100 mM to about 400 mM.

3. The composition according to claim 1, wherein the 3-(3-Cholamidopropyl)-dimethylammonio-1-propanesulfonate (CHAPS) is present in an amount of from about 0.05% to about 0.5% by weight per volume (w/v).

4. The composition according to claim 1, wherein the ratio of integral bARE protein to dissociated A and B forms is at least 2:1.

5. The composition according to claim 1, wherein the bARE protein is an LTK63 or LTK 72 protein.

6. A method of stabilizing a soluble, substantially integral bARE class protein which is an AB5 cholera toxin (CT) ADP-ribosylating toxin or an AB5 *E.coli* heat labile toxin (LT) by combining the bARE class protein with arginine phosphate and 3-(3-Cholamidopropyl)-dimethylammonio-1-propanesulfonate (CHAPS).

7. The method according to claim 6, wherein the Arginine or Arginine phosphate is present in an amount of from about 100 mM to about 400 mM.

8. The method according to claim 6, wherein the 3-(3-Cholamidopropyl)-dimethylammonio-1-propanesulfonate (CHAPS) is present in an amount of from about 0.05% to about 0.5% by weight per volume (w/v).

9. The method according to claim 6, wherein the ratio of integral bARE protein to dissociated A and B forms is at least 2:1.

10. The method according to claim 6, wherein the ABS protein is an LTK63 or LTK 72 protein.

11. An immunogenic composition comprising a composition according to claim 1.

12. An immunogenic composition according to claim 11, wherein further comprising an adjuvant, wherein said adjuvant is not the bARE protein.

13. An immunogenic composition according to claim 12, wherein the adjuvant is a mucosal adjuvant.

* * * * *